US008927029B2

(12) United States Patent
Melander et al.

(10) Patent No.: US 8,927,029 B2
(45) Date of Patent: *Jan. 6, 2015

(54) INHIBITION OF BIOFILMS IN PLANTS WITH IMIDAZOLE DERIVATIVES

(71) Applicants: North Carolina State University, Raleigh, NC (US); Thomas W. Lindsey, Jupiter, FL (US)

(72) Inventors: Christian Melander, Raleigh, NC (US); John Cavanagh, Cary, NC (US); David Ritchie, Durham, NC (US); Robert W. Huigens, III, Apex, NC (US); T. Eric Ballard, Charlottesville, VA (US); Justin J. Richards, Durham, NC (US); Thomas W. Lindsey, Jupiter, FL (US); Jonathan S. Lindsey, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/088,926

(22) Filed: Nov. 25, 2013

(65) Prior Publication Data

US 2014/0079808 A1 Mar. 20, 2014

Related U.S. Application Data

(63) Continuation of application No. 13/600,968, filed on Aug. 31, 2012, now Pat. No. 8,618,149, which is a continuation of application No. 12/324,346, filed on Nov. 26, 2008, now Pat. No. 8,278,340.

(60) Provisional application No. 60/990,483, filed on Nov. 27, 2007, provisional application No. 61/037,034, filed on Mar. 17, 2008.

(51) Int. Cl.
| | | |
|---|---|---|
| *A01N 43/60* | (2006.01) | |
| *A01N 43/16* | (2006.01) | |
| *A01N 59/20* | (2006.01) | |
| *A01N 43/54* | (2006.01) | |
| *A01N 43/50* | (2006.01) | |
| *A01N 43/52* | (2006.01) | |
| *A01N 43/80* | (2006.01) | |
| *A01N 43/90* | (2006.01) | |

(52) U.S. Cl.
CPC ............... *A01N 43/50* (2013.01); *A01N 43/52* (2013.01); *A01N 43/80* (2013.01); *A01N 43/90* (2013.01); *A01N 43/16* (2013.01); *A01N 59/20* (2013.01)
USPC ............ 424/638; 514/392; 514/40; 514/394; 504/275; 504/276

(58) Field of Classification Search
None
See application file for complete search history.

(56) References Cited

U.S. PATENT DOCUMENTS

| | | |
|---|---|---|
| 3,575,929 A | 4/1971 | Jones |
| 4,514,382 A | 4/1985 | Gaffar et al. |
| 5,358,960 A | 10/1994 | Ulrich et al. |
| 5,670,055 A | 9/1997 | Yu et al. |
| 5,814,668 A | 9/1998 | Whittemore et al. |
| 5,834,411 A | 11/1998 | Bolkan et al. |
| 6,143,774 A | 11/2000 | Heckmann et al. |
| 7,087,661 B1 | 8/2006 | Alberte et al. |
| 7,132,567 B2 | 11/2006 | Alberte et al. |
| 7,160,879 B2 | 1/2007 | DeSimone et al. |
| 7,906,544 B2 | 3/2011 | Melander et al. |
| 2003/0171421 A1 | 9/2003 | Davies et al. |
| 2003/0194454 A1 | 10/2003 | Bessette et al. |
| 2003/0196215 A1 | 10/2003 | Olivier et al. |
| 2003/0226163 A1 | 12/2003 | Cramer et al. |
| 2003/0229000 A1 | 12/2003 | Merritt et al. |
| 2004/0024037 A1 | 2/2004 | Ryu et al. |
| 2004/0235934 A1 | 11/2004 | Fischer et al. |
| 2004/0249441 A1 | 12/2004 | Miller et al. |
| 2005/0161859 A1 | 7/2005 | Miller et al. |
| 2006/0014285 A1 | 1/2006 | Eldridge et al. |
| 2006/0018945 A1 | 1/2006 | Britigan et al. |
| 2006/0228384 A1 | 10/2006 | Eldridge |
| 2006/0276468 A1 | 12/2006 | Blow |
| 2007/0033671 A1 | 2/2007 | Jiang et al. |
| 2007/0087938 A1 | 4/2007 | Hartfeldt |

(Continued)

FOREIGN PATENT DOCUMENTS

| | | |
|---|---|---|
| WO | WO 2005/012263 A1 | 2/2005 |
| WO | WO 2008/094479 A1 | 8/2008 |

OTHER PUBLICATIONS

Bonner, J. "Antibiotic combinations tackle resistance." Chemistry World, 2007, http://www.rsc.org/chemistryworld/news/2007/april/04040701.asp.*

(Continued)

*Primary Examiner* — Mina Haghighatian
*Assistant Examiner* — Erin Hirt
(74) *Attorney, Agent, or Firm* — Myers Bigel Sibley & Sajovec, P.A.

(57) ABSTRACT

Disclosure is provided for methods of preventing, removing or inhibiting microbial biofilm formation or microbial infection in a plant or plant part thereof, including applying thereto a treatment effective amount of an active compound as described herein, or an agriculturally acceptable salt thereof. Methods of enhancing a microbicide (e.g., including a copper, antibiotic, bacteriophage, etc.) and/or plant defense activator are also provided, including applying an active compound as described herein. Compositions comprising an active compound as described herein in an agriculturally acceptable carrier are also provided, and in some embodiments the compositions further include a microbicide (e.g., including copper, antibiotic, bacteriophage, etc.) and/or plant defense activator.

20 Claims, 2 Drawing Sheets

(56) References Cited

U.S. PATENT DOCUMENTS

2007/0142371 A1 6/2007 Cogan et al.
2007/0185092 A1 8/2007 Zhu et al.
2007/0231291 A1 10/2007 Huang et al.
2008/0181923 A1 7/2008 Melander et al.

OTHER PUBLICATIONS

Walker TS et al. *Pseudomonas aeruginosa*—plant root interactions. Pathogenicity, biofilm formation, and root exudation. Plant Physiology. Jan. 2004; 134: 320-331.
Borkow G and Gabbay J. Copper as a biocidal tool. Current Medicinal Chemistry. 2005; 12: 2163-2175.
Cavalleri B et al. Synthesis and biological activity of some 2-aminoimidazoles. Arzneimittel-Forschung. 1977; 27: 1889-1895.
Shore D. College Profile: Dr. John Cavanagh shows that in scientific collaboration—as in a community of molecules—the product is more powerful than the sum of its parts. Perspectives Online. The Magazine of the College of Agriculture and Life Sciences at NC State. North Carolina State University. Summer 2007: 4 pp.
Fishing for seafood safety. Scope. North Carolina State University College of Physical and Mathematical Sciences. Fall 2007: 11.
Galvin F. Marine inspiration for biofilm break up. Chemical Biology. RCS Publishing. Mar. 5, 2008: 2 pp.
Melander C et al. Evaluation of dihydrooroidin as an antifouling additive in marine paint. International Biodeterioration & Biodegradation. 2009; 53: 529-532.
Stokstad E. Sponging away antibiotic resistance. Findings. The Science Magazine News Blog. Feb. 14, 2009: 1 p.
Lydersen K. Scientists learning to target bacteria where they live. washingtonpost.com. The Washington Post. Mar. 9, 2009; A05: 3 pp.
Taking the Resistance out of drug-resistant infections. PhysOrg.com. Apr. 10, 2009: 2 pp.
Avery S. Slime-fighting molecule may rearm antibiotics. newsobserver.com. The News and Observer. Raleigh, NC. Apr. 22, 2009: 2 pp.
International Search Report and Written Opinion, PCT/US09/02446, mailed Aug. 31, 2009.
Casalinuovo IA et al. Fluconazole resistance in *Candida albicans*: a review of mechanisms, European Review for Medical and Pharmacological Sciences. 2004; 8(2): 69-77.
Rogers SA et al. A 2-aminobenzimidazole that inhibits and disperses gram-positive biofilms through a zinc-dependent mechanism. J. Am. Chem. Soc. 2009; 131(29): 9868-9869.
Richards JJ et al. Amide isosteres of oroidin: assessment of antibiofilm activity and *C. elegans* toxicity. Journal of Medicinal Chemistry. 2009; 52(15): 4582-4585.
Richards JJ and Melander C. Controlling bacterial biofilms. ChemBioChem. Epub ahead of print: Aug. 13, 2009; 9 pp.
International Search Report and Written Opinion, PCT/US09/66979, mailed Feb. 12, 2010.
International Search Report and Written Opinion, PCT/US09/02101, mailed Jul. 13, 2009.
Hoffmann H and Lindel T. Synthesis of the pyrrole-imidazolealkaloids. Synthesis. 2003; 12: 1753-1783.
Kelly SR et al. Effects of Caribbean sponge extracts on bacterial attachment. Aquatic Microbial Ecology. Mar. 13, 2003; 31: 175-182.
Kelly SR et al. Effects of Caribbean sponge secondary metabolites on bacterial colonization. Aquatic Microbial Ecology. Sep. 6, 2005; 40: 191-203.
Ballard TE et al. Synthesis and antibiofilm activity of a second-generation reverse-amide oroidin library: a structure-activity relationship study. Chemistry. 2008; 14(34): 10745-61. Abstract only.
Huigens RW 3rd et al. Control of bacterial biofilms with marine alkaloid derivatives. Molecular BioSystems. 2008; 4: 614-621.
Richards JJ et al. Inhibition and dispersion of *Pseudomonas aeruginosa* biofilms with reverse amide 2-aminoimidazole oroidin analogues. Organic & Biomolecular Chemistry. Apr. 21, 2008; 6(8): 1301-1512.
Richards JJ et al. Effects of N-pyrrole substitution on the anti-biofilm activities of oroidin derivatives against *Acinetobacter baumannii*. Bioorganic & Medicinal Chemistry Letters. 2008; 18: 4325-4327.
Richards JJ and Melander C. Synthesis of a 2-aminoimidazole library for antibiofilm screening utilizing the Sonogashira reaction. J. Org. Chem. 2008; 73(13): 5191-5193.
Richards JJ et al. Inhibition and dispersion of proteobacterial biofilms. Chem. Comm. 2008; 1698-1700.
Richards JJ et al. Synthesis and screening of an oroidin library against *Pseudomonas aeruginosa* biofilms. ChemBioChem. 2008; 9: 1267-1279.
Rogers SA and Melander C. Construction and screening of a 2-aminoimidazole library identifies a small molecule capable of inhibiting and dispersing bacterial biofilms across order, class, and phylum. Angew. Chem. Int. Ed. 2008; 47: 5229-5231.
Ballard TE et al. Antibiofilm activity of a diverse oroidin library generated through reductive acylation. J. Org. Chem. 2009; 74(4): 1755-1758.
Huigens RW 3rd et al. Inhibition of *Acinetobacter baumannii*, *Staphylococcus aureus* and *Pseudomonas aeruginosa* biofilm formation with a class of TAGE-triazole conjugates. Org. Biomol. Chem. 2009; 7: 794-802.
Rogers SA et al. Tandem dispersion and killing of bacteria from a biofilm. Organic & Biomolecular Chemistry. 2009; 7: 603-606.
Foley L. and Büchi G. Biomimetic synthesis of dibromophakellin. J. Am. Chem. Soc. (1982), vol. 104, pp. 1776-1777.
Yamada A. et al. Development of chemical substances regulating biofilm formation. Bull. Chem. Soc. Jpn. (1997), No. 70, pp. 3061-3069.
Mourabit A. A. and Potier P. Sponge's molecular diversity through the ambivalent reactivity of 2-aminoimidazole: a universal chemical pathway to the oroidin-based pyrrole-imidazole alkaloids and their palau'amine congeners. Eur. J. Org. Chem. (2001), pp. 237-243.
Musk Jr. D.J. and Hergenrother P.J. Chemical countermeasures for the control of bacterial biofilms: effective compounds and promising targets. Current Medicinal Chemistry (2006), vol. 13, pp. 2163-2177.
Danhorn T and Fuqua C. Biofilm formation by plant-associated bacteria. Annu. Rev. Microbio. (2007). vol. 61, pp. 401-422.
Huigens III R.W., et al. Inhibition of *Pseudomonas aeruginosa* biofilm formation with bromoageliferin analogues. J. Am. Chem. Soc. (2007), vol. 129, pp. 6966-6967.
International Search Report and Written Opinion for PCT/US08/01045, dated May 9, 2008.
International Search Report and Written Opinion for PCT/US08/13161, dated Jan. 28, 2009.
Nagai W et al. Synthesis of 2-amino-I-histidine and 2-aminohistamine. Journal of Organic Chemistry. Jan. 1, 1973; 88(11): 1971-1974.
Ballard TE et al. Synthesis and antibody activity of a second-generation reverse-amide oroidin library: a structure-activity relationship study. Chem Eur J. Oct. 22, 2008; 14(34): 10745-10761.
Supplementary European Search Report and Search Opinion, EP 08854205.1, mailed May 9, 2014.

* cited by examiner

INHIBITION OF BIOFILMS IN PLANTS WITH IMIDAZOLE DERIVATIVES

RELATED APPLICATIONS

This application is a continuation of and claims priority to U.S. patent application Ser. No. 13/600,968, filed Aug. 31, 2012, now allowed, which is a continuation of U.S. patent application Ser. No. 12/324,346, filed Nov. 26, 2008, now U.S. Pat. No. 8,278,340, which claims the benefit under 35 U.S.C. §119(e) of U.S. Provisional Patent Application Ser. No. 60/990,483, filed Nov. 27, 2007, and U.S. Provisional Application Ser. No. 61/037,034, filed Mar. 17, 2008, the disclosures of each of which are incorporated herein by reference in its entirety.

FIELD OF THE INVENTION

This invention relates to compositions and methods useful for controlling biofilms and microorganisms in plants, particularly vascular plants.

BACKGROUND OF THE INVENTION

New approaches are urgently needed to improve agricultural production, given the steadily growing global population that is predicted to reach 6-9 billion persons by mid-century, the continual strain on existing and finite agricultural lands, and the recent diversion of valuable agricultural land from production of crops to production of biomass for fuels. Here we describe new approaches that may serve to generically increase agricultural production by stemming the adverse effects of microorganisms on plants.

Melander and coworkers recently reported a study wherein they identified novel synthetic compounds that inhibit biofilm formation (Huigens, R. W., III; Richards, J. J.; Parise, G.; Ballard, T. E.; Zeng, W.; Deora, R.; Melander, C. *J. Am. Chem. Soc.* 2007, 129, 6966-6967). Biofilms are communities of microorganisms (primarily bacteria but also can include archaea, protozoa, and algae) anchored to a surface (*Molecular Ecology of Biofilms*; McLean, J. C.; Decho, A. W., Eds, Horizon Scientific Press: Norfolk England, 2002.; see also "Biofilm" in Wikipedia). It is estimated that the majority of all bacteria are present in biofilms rather than in free-swimming (planktonic) form. The inspiration for the Melander paper stemmed in part from recognition that marine natural products that serve as antifouling agents or antifeedants function to inhibit biofilm formation. The marine organisms in particular are marine sponges, which have long been recognized as valuable sources of bioactive compounds (Thakur, N. L.; Muller, W. E. G. *Curr. Sci.* 2004, 86, 1506-1512). Moreover, the authors identified a common structural motif in a variety of such marine natural products, a 2-aminoimidazole, and hypothesized that the imidazole moiety, in conjunction with an annulated ring, constituted the core pharmacophore of the marine product. Synthetic analogues of this core unit proved to exhibit high activity in the inhibition of biofilm formation.

The five main crops on which modern societies depend most heavily include corn, cotton, rice, soybeans, and wheat. All of these crops are affected in a deleterious manner by biofilm formation. In addition, other valuable plants such as those producing fruits and vegetables are similarly affected. Plants grown for biomass stand to increase as a valuable crop, albeit not for food, and also can benefit from protection from biofilm formation. Forestry crops also suffer from biofilms.

SUMMARY OF THE INVENTION

The present invention is a method of preventing, removing or inhibiting microbial biofilm formation or microbial infection in a plant or plant part thereof, comprising applying to the plant or plant part a treatment effective amount of a compound selected from the group consisting of:

a compound of Formula (I):

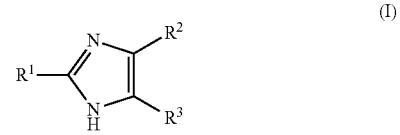

wherein:

$R^1$ and $R^2$ and $R^3$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);

or an agriculturally acceptable salt thereof;

a compound of Formula (I)(a):

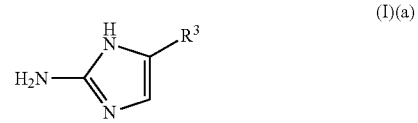

wherein:

$R^3$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide (each group can be optionally substituted);

or an agriculturally acceptable salt thereof;

a compound of Formula (II):

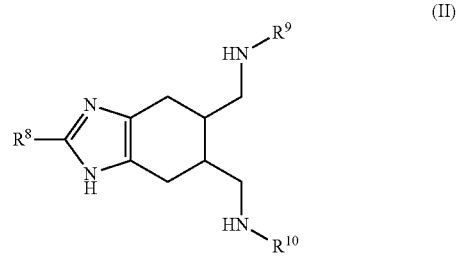

wherein:

$R^8$ is selected from the group consisting of: H, amino, hydroxy, and thiol; and $R^9$ and $R^{10}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);

or an agriculturally acceptable salt thereof;

a compound of Formula (II)(b):

(II)(b)

wherein:
R¹¹ and R¹² are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);
or an agriculturally acceptable salt thereof;
a compound of Formula (II)(c):

(II)(c)

wherein:
R¹³ and R¹⁴ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);
or an agriculturally acceptable salt thereof;
a compound of Formula (III):

(III)

wherein:
R¹⁵, R¹⁶, R¹⁷, R¹⁸, R¹⁹, R²⁰, R²¹ and R²² are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);
or an agriculturally acceptable salt thereof;
a compound of Formula (IV):

(IV)

wherein:
R²³ is selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);
or an agriculturally acceptable salt thereof;
a compound of Formula (V) or Formula (VI):

(V)

(VI)

(each formula can be optionally substituted);
or an agriculturally acceptable salt thereof;
a compound of Formula (X):

Formula (X)

wherein:
R¹ and R² and R³ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted); and
A and B are each independently selected from N, S and O;
or an agriculturally acceptable salt thereof;

a compound of Formula (X)(I)(a):

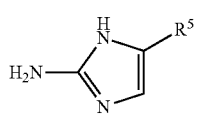

(X)(I)(a)

wherein R⁵ is an alkyl, alkenyl or alkynyl having an amide group substituted thereon (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(a)(1):

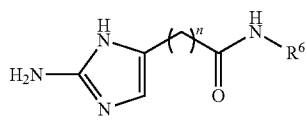

(X)(I)(a)(1)

wherein:
n is 1 to 10 carbons, saturated or unsaturated; and
R⁶ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(a)(2):

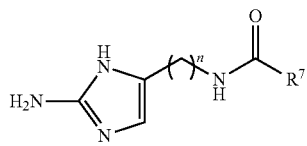

(X)(I)(a)(2)

wherein:
n is 1 to 10 carbons, saturated or unsaturated, substituted or unsubstituted; and
R⁷ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;

a compound of Formula (X)(I)(a)(2)(A):

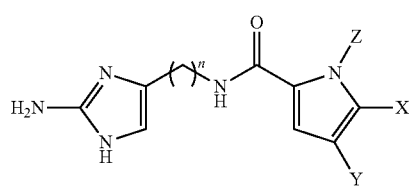

(X)(I)(a)(2)(A)

wherein:
n is 1 to 10 carbons, saturated or unsaturated, substituted or unsubstituted; and X, Y and Z are each independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(b):

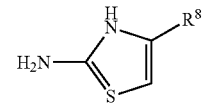

(X)(I)(b)

wherein R⁸ is an alkyl, alkenyl or alkynyl having an amide group substituted thereon (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(b)(1):

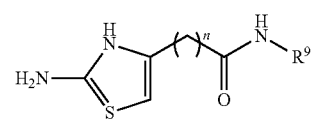

(X)(I)(b)(1)

wherein:
n is 1 to 10 carbons, saturated or unsaturated; and
R⁹ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;

a compound of Formula (X)(I)(b)(2):

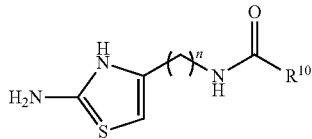

(X)(I)(b)(2)

wherein:
n is 1 to 10 carbons, saturated or unsaturated, substituted or unsubstituted; and
$R^{10}$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(b)(2)(A):

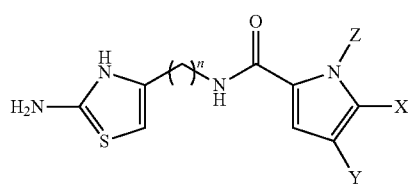

(X)(I)(b)(2)(A)

wherein:
n is 1 to 10 carbons, saturated or unsaturated, substituted or unsubstituted; and X, Y and Z are each independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(c):

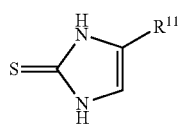

(X)(I)(c)

wherein $R^{11}$ is an alkyl, alkenyl or alkynyl having an amide group substituted thereon (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(c)(1):

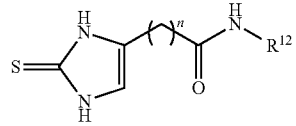

(X)(I)(c)(1)

wherein:
n is 1 to 10 carbons, saturated or unsaturated; and
$R^{12}$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(a)(2):

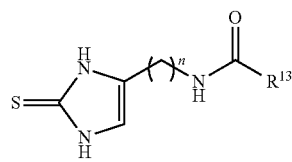

(X)(I)(c)(2)

wherein:
n is 1 to 10 carbons, saturated or unsaturated, substituted or unsubstituted; and
$R^{13}$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(c)(2)(A):

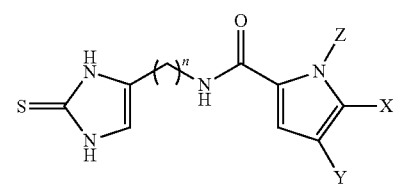

(X)(I)(c)(2)(A)

wherein:

n is 1 to 10 carbons, saturated or unsaturated, substituted or unsubstituted; and X, Y and Z are each independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);

or an agriculturally acceptable salt thereof.

In some embodiments, the plant is a fruit or a vegetable crop plant.

In some embodiments, the plant is a citrus tree, and the compound is applied in an amount effective to treat or control a bacterial disease selected from the group consisting of canker, bacterial spot, Black Pit (fruit), Blast, citrus variegated chlorosis, and Citrus Huanglongbing. In some embodiments, the citrus tree is selected from the group consisting of orange, grapefruit, Mandarin, lemon, lime and Kumquat.

In some embodiments, the plant is a pome fruit, and the compound is applied in an amount effective to treat or control a bacterial disease selected from the group consisting of Fire Blight, Crown Gall, Blister spot and Hairy root. In some embodiments, the pone fruit is selected from the group consisting of apple, pear, quince, Asian pear, and loquats.

In some embodiments, the plant is a *Musa* species such as a banana, and the compound is applied in an amount effective to treat or control *Ralstonia solanacearum*.

In some embodiments, the plant is a cole (Brassicaceae) such as cabbage or broccoli, and the compound is applied in an amount effective to treat or control black rot (*Xanthononas campestris*).

In some embodiments, the plant is a winegrape, and the compound is applied in an amount effective to treat or control for Pierce's disease (*Xylella fastidosa*) or crown gall (*Agrobacterium vitas, A. tumefaciens*).

In some embodiments, the plant is a strone fruit or nut (e.g., peaches, nectarines, plums, almonds, walnuts), and the compound is applied in an amount effective to treat or control bacterial spot and/or blight caused by *Xanthomonas arboricola*; blight caused by *Pseudomonas syringae*); crown gall caused by *Agrobacterium tumefaciens*; phony peach and plum; or almond leaf scorch caused by *Xylella fastidosa*.

In some embodiments, the plant is a landscape and/or shade tree (e.g., oak, maple, birch, etc) for bacterial leaf scorch disease (e.g., cause by *Xylella fastidosa*).

In some embodiments, the plant is a potato, and the compound is applied in an amount effective to treat or control soft rot or black leg (*Erwinia, Pectobacterium*).

In some embodiments, the plant is a pepper plant, and the compound is applied in an amount effective to treat or control a bacterial disease selected from the group consisting of Bacterial Spot, Bacterial wilt, Bacterial canker, and Syringae seedling blight and leaf spot.

In some embodiments, the plant is a tomato plant, and the compound is applied in an amount effective to treat or control a bacterial disease selected from the group consisting of: bacterial canker, bacterial speck, bacterial spot, bacterial stem rot and fruit rot, Bacterial wilt, Pith necrosis, and Syringae leaf spot.

In some embodiments, the plant is a soybean plant, and the compound is applied in an amount effective to treat or control a bacterial disease selected from the group consisting of Bacterial blight, Bacterial pustules, Bacterial wilt, Bacterial crinkle leaf, Bacterial tan spot, and Wildfire.

In some embodiments, the plant is corn, and the compound is applied in an amount effective to treat or control a bacterial disease selected from the group consisting of: Bacterial leaf blight, stalk rot, bacterial stripe, chocolate spot, *holcus* spot all causes by *Pseudomonas* species, Bacterial leaf spot caused by *Xanthomomas* species, Bacterial stalk rot, top rot and Stewart's disease caused by *Erwinia* (Pantoea) species, seed rot-seedling blight caused by *Bacillus* species, Purple leaf sheath caused by *Hemiparasitic* bacteria, Corn stunt caused by *Spriroplasma kunkelii*, Goss's bacterial wilt and blight caused by *Clivibacter michiganensis*.

In some embodiments, the plant is cotton, and the compound is applied in an amount effective to treat or control a bacterial disease selected from the group consisting of Bacterial blight caused by *Xanthomonas* species, and Crown gall caused by *Agrobacterium* species and Lint degradation caused by *Erwinia* species.

In some embodiments, the plant is wheat, and the compound is applied in an amount effective to treat or control a bacterial disease selected from the group consisting of Bacterial leaf blight, bacterial sheath rot and Basal glume rot caused by *Pseudomonas* species, Bacterial mosaic and Spike blight caused by *Clavibacter* species, Black chaff caused by *Xanthomonas* species, and Pink seed caused by *Erwinia* species.

In some embodiments, the plant is rice, and the compound is applied in an amount effective to treat or control a bacterial disease selected from the group consisting of bacterial blight and leaf streak caused by *Xanthomonas* species, Foot rot caused by *Erwinia* species, Grain rot caused by *Burkholderia* species, and Sheath brown rot caused by *Pseudomonas* species.

In some embodiments, the plant is pineapple, and the compound is applied in an amount effective to treat or control a bacterial disease selected from the group consisting of bacterial heart rot, fruit collapse, bacterial fruitlet brown rot, marbled fruit, pink fruit and soft rot caused by *Erwinia* species, and Acetic souring caused by Acetic acid bacteria.

In some embodiments, the microbial biofilm formation or microbial infection is caused by a fungi. In some embodiments, the compound is applied to the plant in an amount effective to treat or control a fungal disease selected from the group consisting of rots, leaf molds, blights, wilts, damping-off, spot, root rot, stem rot, mildew, brown spot, gummosis, melanose, post-bloom fruit drop, scab, *alternaria*, canker, flyspeck, fruit blotch, dieback, downy mildews, ear rots, anthracnose bunts, smut, rust, eyespot and pecky rice.

In some embodiments, the plant is citrus, and the compound is applied in an amount effective to treat or control a fungal disease selected from the group consisting of: *Alternaria* brown spot caused by *Alternaria alternaria*, Brown rot caused by *Phytophtora citricola*, Greasy spot and Greasy spot rind blotch caused by *Mycosphaerella citri*, Melanose caused by *Diaporthe citri, Phytophthora* foot rot, gummosis and root rot caused by *Phytophthora citrophthora, Phytophthora palmivora, Phytophthora syringae* and other *Phytophthora* spp, Post bloom fruit drop caused by *Colletotrichum acutatum*, and Scab caused by *Elsinoe fawcettii*.

In some embodiments, the plant is Pome fruit, and the compound is applied in an amount effective to treat or control a fungal disease selected from the group consisting of: Apple scab caused by *Venturia inaequalis*, Bitter rot caused by *Colletotrichum gloeosporioides, Diplodia* canker caused by *Dilpodia mutila, Phytophthora* crown, collar, root and fruit rot caused by *Phytophthora* spp., Powdery mildew caused by

*Podosphaera leucotricha*, Pacific Coast pear rust, Cedar apple rust, Quince rust caused by *Gymnosporangium* spp., and Flyspeck caused by *Schizothyrium pomi*.

In some embodiments, the plant is Peppers, and the compound is applied in an amount effective to treat or control a fungal disease selected from the group consisting of: Anthracnose caused by *Colletotrichum* spp., Damping-off and root rot caused by *Rhizoctonia solani, Phytophthora* spp., *Fusarium* spp., and *Pythium* spp., *Phytophthora* blight caused by *Phytophthora capsici*, and *Verticillium* wilt caused by *Verticillium albo-atrium*.

In some embodiments, the plant is Tomato, and the compound is applied in an amount effective to treat or control a fungal disease selected from the group consisting of: *Alternaria* stem canker caused by *Alternaria alternaria*, Anthracnose caused by *Colletotrichum* spp., *Fusarium* crown, root rot and wilt caused by *Fusarium oxysporum*, Gray mold caused by *Botrytis cinerea*, Late blight caused by *phytophthora infestans, Pythium* damping-off and fruit rot caused by *Pythium* spp., *Rhizoctonia* damping-off and fruit rot caused by *Rhizoctonia solani, Septoria* leaf spot caused by *Septoria lycopersici, Verticillium* wilt caused by *Verticillium alboatrum*, and White mold caused by *Sclerotinia sclerotiorum*.

In some embodiments, the plant is Soybean, and the compound is applied in an amount effective to treat or control a fungal disease selected from the group consisting of: *Phytophthora* root and stem rot caused by *Phytophthora sojae, Pythium* root rot, damping-off and seed decay caused by *Pythium* spp., Brown stem rot caused by *Phialophora gregata, Rhizoctonia* root and stem rot caused by *Rhizoctonia solani*, Stem canker, pod and stem blight caused by *Diaporthe phaseolorum, Phomopsis* seed decay caused by *Phomopsis longicolla*, Charcoal rot caused by *Macrophomina phaseolina, Sclerotinia* stem rot caused by *Sclerotinia sclerotiorum*, Sudden death syndrome caused by *Fusarium solani*, and Soybean Rust caused by *Phakopsora pachyrhizi*.

In some embodiments, the plant is Grape, and the compound is applied in an amount effective to treat or control a fungal disease selected from the group consisting of: *Alternaria* rot caused by *Alternaria alternaria*, Angular leaf spot caused by *Mycosphaerella angulata, Botrytis* bunch rot and blight caused by *Botrytis cinerea, Diplodia* cane dieback and bunch rot caused by *Diplodia natalensis*, Downy mildew caused by *Plasmopara viticola, Phytophthora* crown and root rot caused by *Phytophthora* spp., Powdery mildew caused by *Uncinula necator*, Ripe rot caused by *Glomerella cingulata, Septoria* leaf spot caused by *Septoria ampelopsidis*, and *Verticillium* wilt caused by *Verticillium dahliae*.

In some embodiments, the plant is Potato, and the compound is applied in an amount effective to treat or control a fungal disease selected from the group consisting of: Brown spot, Black pit and Early blight caused by *Alternaria* spp., *Fusarium* dry rot and wilt caused by *Fusarium* spp., Gangrene caused by *Phoma* spp., Late blight and Pink rot caused by *Phytophthora* spp., *Rhizoctonia* canker and black scurf caused by *Rhizoctonia solani, Rosellinia* black rot caused by *Rosellinia* spp., *Septoria* leaf spot caused by *Septoria lycopersici*, Stem rot caused by *Sclerotium rolfsii, Verticillium* wilt caused by *Verticillium albo-atrum*, and White mold caused by *Sclerotinia sclerotiorum*.

In some embodiments, the plant is Pineapple, and the compound is applied in an amount effective to treat or control a fungal disease selected from the group consisting of: Anthracnose caused by *Colletotrichum ananas*, Butt rot and White leaf spot caused by *Chalara paradoxa*, Leaf spot caused by *Curvularia eragrostidis, Phytophthora* heart rot caused by *Phytophthora cinnamomi* and *Phytophthora parasitica*, Root rot and Seedling blight caused by *Pythium* spp., and Leaking brown ring caused by *Tofflieadis dimenationa*.

In some embodiments, the plant is Cotton, and the compound is applied in an amount effective to treat or control a fungal disease selected from the group consisting of: Anthracnose caused by *Glomerella gossypii*, Boll rot caused by *Colletotrichum gossypii, Fusarium* spp., *Phytophthora* spp., or *Rhizoctonia solani, Fusarium* wilt caused by *Fusarium oxysporum*, Leaf spot caused by *Alternaria* spp., *Cercospora gossypina, Rhizoctonia solani*, and *Stemphylium solani*, Lint contamination caused by *Aspergillus flavus*, Powdery mildew caused by *Leveillula taurica*, Cotton rust caused by *Puccinia schedonnardii*, Southwestern cotton rust caused by *Puccinia cacabata*, Tropical cotton rust caused by *Phakopsora gossypii*, Southern blight caused by *Sclerotium rolfsii*, Seedling disease complex caused by *Colletotrichum gossypii, Fusarium* spp., *Pythium* spp., *Rhizoctonia solani*, or *Thielaviopsis basicola*, Stem canker caused by *Phoma exigua*, and *Verticillium* wilt caused by *Verticillium dahliae*.

In some embodiments, the plant is Corn, and the compound is applied in an amount effective to treat or control a fungal disease selected from the group consisting of: Anthracnose caused by *Colletotrichum graminicola, Aspergillus* ear and kernel rot caused by *Aspergillus flavus*, Banded leaf, sheath spot, root rot and stalk rot caused by *Rhizoctonia solani*, Brown spot, Black spot and Stalk rot caused by *Physoderma maydis, Curvularia* leaf spot caused by *Curvularia clavata, Diplodia* ear rot, stalk rot, seed rot and seedling blight caused by *Dilpodia* spp., Downey mildews caused by *Sclerophthora* spp. or *Peronosclerospora* spp., Ear rots caused by *Alternaria alternaria*, Ergot caused by *Claviceps gigantea, Fusarium* ear, stalk, kernel, root, seed rot, seedling blight caused by *Fusarium* spp., *Cercospora* leaf spot caused by *Cercospora zeae-maydis, Helminthosporium* ear rot caused by *Helminthosporium carbonum, Pythium* root rot and stalk rot caused by *Pythium* spp., *Rhizoctonia* ear rot caused by *Rhizoctonia zeae*, Common corn rust and Southern corn rust caused by *Puccinia* spp., Southern blight caused by *Athelia rolfsii*, Common smut caused by *Ustilago zeae*, Southern corn leaf blight and stalk rot caused by *Cochliobolus heterostrophus*, and storage rots caused by *Aspergillus* spp. and *Penicillium* spp.

In some embodiments, the plant is Rice, and the compound is applied in an amount effective to treat or control a fungal disease selected from the group consisting of: Black kernel caused by *Curvularia lunata*, Blast caused by *Pyricularia oryzae*, Brown spot caused by *Cochliobolus miyabeanus*, Downy mildew caused by *Sclerophthora macrospora*, False smut caused by *Ustilaginoidea virens*, Narrow brown leaf spot caused by *Cercospora janseana*, Pecky rice caused by *Fusarium* spp., *Microdochium oryzae*, or *Sarocladium oryzae*, Root rot caused by *Fusarium* spp, or *Pythium* spp., Seedling blight caused by fungi (e.g., *Cochliobolus miyabeanus, Curvularia* spp., *Fusarium* spp., *Rhizoctonia solani*,

*Sclerotium rolfsii* and *Athelia rolfsii*), Stackburn caused by *Alternaria padwickii*, Stem rot caused by *Magnaporthe salvinii*, Water-mold (seed-rot and seedling disease) caused by *Achlya* spp., *Fusarium* spp., or *Pythium* spp.

In some embodiments, the plant is Wheat, and the compound is applied in an amount effective to treat or control a fungal disease selected from the group consisting of: Alternaria leaf blight caused by *Alternaria triticina*, Anthracnose caused by *Colletotrichum graminicola*, Black head molds caused by *Cladosporium* spp., *Epicoccum* spp., *Sporobolomyces* spp. or *Stemphylium* spp., Common bunt caused by *Tilletia* spp., Crown rot, seedling blight and dryland root rot caused by *Fusarium* spp. or *Gibberella* spp., Downey mildew caused by *Sclerophthora macrospora*, Dwarf bunt caused by *Tilletia controversa*, Ergot caused by *Claviceps purpurea*, Eyespot caused by *Tapesia yallundae*, Leaf rust caused by *Puccinia triticina*, Loose smut caused by *Ustilago tritici*, Microscopia leaf spot caused by *Phaeosphaeria microscopia*, Phoma spot caused by *Phoma* spp., Powdery mildew caused by *Erysiphe graminis*, *Pythium* root rot, Snow rot caused by *Pythium* spp., Rhizoctonia root rot caused by *Rhizoctonia solani*, Scab (head blight) caused by *Fusarium* spp. or *Gibberella* spp., Southern blight caused by *Sclerotium rolfsii*, Speckled snow mold caused by *Typhula* spp., Stem rust caused by *Puccinia graminis*, storage molds caused by *Aspergillus* spp. or *Penicillium* spp., Take-all caused by *Gaeumannomyces graminis*, and Zoosporic root rot caused by *Lagena radicola*.

A further aspect of the present invention is an agricultural composition comprising: (a) an agriculturally acceptable carrier (e.g., an aqueous carrier or a solid particulate carrier); and (b) an antimicrobial or biofilm preventing, removing or inhibiting compound selected from the group consisting of:

a compound of Formula (I):

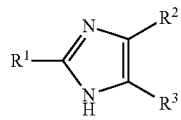

(I)

wherein:

$R^1$ and $R^2$ and $R^3$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);

or an agriculturally acceptable salt thereof;

a compound of Formula (I)(a):

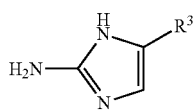

(I)(a)

wherein:

$R^3$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide (each group can be optionally substituted);

or an agriculturally acceptable salt thereof;

a compound of Formula (II):

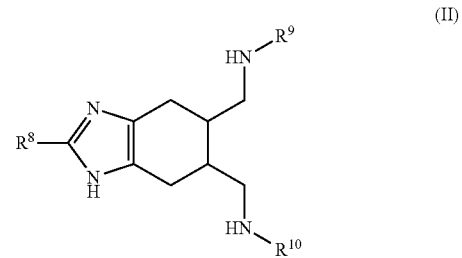

(II)

wherein:

$R^8$ is selected from the group consisting of: H, amino, hydroxy, and thiol; and $R^9$ and $R^{10}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);

or an agriculturally acceptable salt thereof;

a compound of Formula (II)(b):

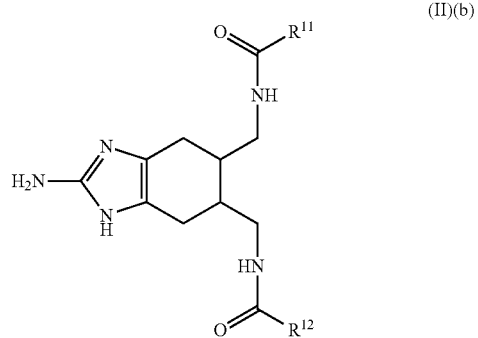

(II)(b)

wherein:

$R^{11}$ and $R^{12}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);

or an agriculturally acceptable salt thereof;

a compound of Formula (II)(c):

(II)(c)

wherein:
R[13] and R[14] are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);
or an agriculturally acceptable salt thereof;
a compound of Formula (III):

(III)

wherein:
R[15], R[16], R[17], R[18], R[19], R[20], R[21] and R[22] are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);
or an agriculturally acceptable salt thereof;
a compound of Formula (IV):

(IV)

wherein:
R[23] is selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);
or an agriculturally acceptable salt thereof;

a compound of Formula (V) or Formula (VI):

(V)

(VI)

(each formula can be optionally substituted);
or an agriculturally acceptable salt thereof;
a compound of Formula (X):

Formula (X)

wherein:
R[1] and R[2] and R[3] are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted); and
A and B are each independently selected from N, S and O;
or an agriculturally acceptable salt thereof;
a compound of Formula (X)(I)(a):

(X)(I)(a)

wherein R[5] is an alkyl, alkenyl or alkynyl having an amide group substituted thereon (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(a)(1):

(X)(I)(a)(1)

wherein:
n is 1 to 10 carbons, saturated or unsaturated; and
R[6] is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);

or an agriculturally acceptable salt thereof;

a compound of Formula (X)(I)(a)(2):

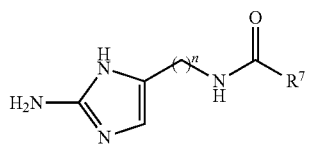

(X)(I)(a)(2)

wherein:

n is 1 to 10 carbons, saturated or unsaturated, substituted or unsubstituted; and $R^7$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);

or an agriculturally acceptable salt thereof;

a compound of Formula (X)(I)(a)(2)(A):

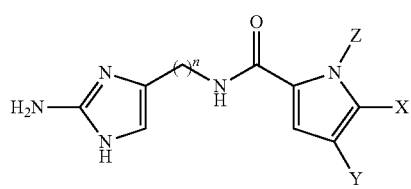

(X)(I)(a)(2)(A)

wherein:

n is 1 to 10 carbons, saturated or unsaturated, substituted or unsubstituted; and X, Y and Z are each independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);

or an agriculturally acceptable salt thereof;

a compound of Formula (X)(I)(b):

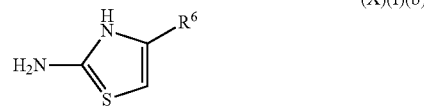

(X)(I)(b)

wherein $R^8$ is an alkyl, alkenyl or alkynyl having an amide group substituted thereon (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);

or an agriculturally acceptable salt thereof;

a compound of Formula (X)(I)(b)(1):

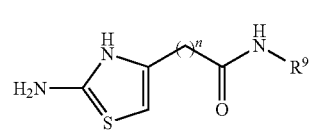

(X)(I)(b)(1)

wherein:

n is 1 to 10 carbons, saturated or unsaturated; and $R^9$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);

or an agriculturally acceptable salt thereof;

a compound of Formula (X)(I)(b)(2):

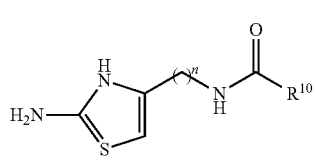

(X)(I)(b)(2)

wherein:

n is 1 to 10 carbons, saturated or unsaturated, substituted or unsubstituted; and $R^{10}$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);

or an agriculturally acceptable salt thereof;

a compound of Formula (X)(I)(b)(2)(A):

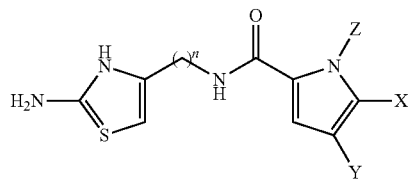

(X)(I)(b)(2)(A)

wherein:
n is 1 to 10 carbons, saturated or unsaturated, substituted or unsubstituted; and X, Y and Z are each independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(c):

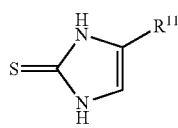

(X)(I)(c)

wherein $R^H$ is an alkyl, alkenyl or alkynyl having an amide group substituted thereon (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(c)(1):

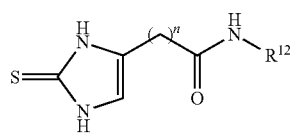

(X)(I)(c)(1)

wherein:
n is 1 to 10 carbons, saturated or unsaturated; and
$R^{12}$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;

a compound of Formula (X)(I)(a)(2):

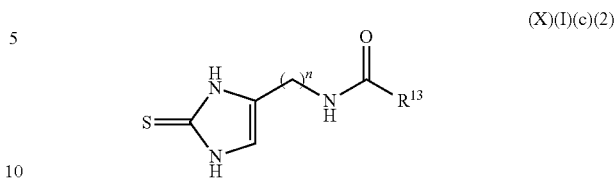

(X)(I)(c)(2)

wherein:
n is 1 to 10 carbons, saturated or unsaturated, substituted or unsubstituted; and
$R^{13}$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(c)(2)(A):

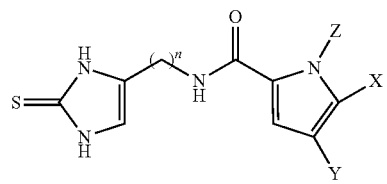

(X)(I)(c)(2)(A)

wherein:
n is 1 to 10 carbons, saturated or unsaturated, substituted or unsubstituted; and X, Y and Z are each independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof.

In some embodiments, the composition further includes a microbicide. In some embodiments, the microbicide comprises copper (e.g., copper hydroxide). In some embodiments, the microbicide comprises an antibiotic or a bacteriophage. In some embodiments, the composition further includes a plant defense activator. In some embodiments, the composition further includes both a plant defense activator and a microbicide. In some embodiments, the compound is a compound of Formula (II)(b)(vi)(trans)(±):

(II)(b)(vi)(trans)(±)

[Structure: 2-amino-4,5,6,7-tetrahydrobenzimidazole with trans bis(methylamide-4,5-dibromopyrrole) substituents]

or an agriculturally acceptable salt thereof.

Further provided are methods of enhancing the effects of a microbicide comprising applying in combination with said microbicide an active compound selected from the group consisting of:

a compound of Formula (I):

(I)

[Structure: imidazole with R¹, R², R³ substituents]

wherein:

R¹ and R² and R³ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);

or an agriculturally acceptable salt thereof;

a compound of Formula (I)(a):

(I)(a)

[Structure: 2-amino imidazole with R³ substituent]

wherein:

$R^3$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide (each group can be optionally substituted);

or an agriculturally acceptable salt thereof;

a compound of Formula (II):

(II)

[Structure: 4,5,6,7-tetrahydrobenzimidazole with R⁸, R⁹, R¹⁰ substituents]

wherein:

$R^8$ is selected from the group consisting of: H, amino, hydroxy, and thiol; and $R^9$ and $R^{10}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);

or an agriculturally acceptable salt thereof;

a compound of Formula (II)(b):

(II)(b)

[Structure: 2-amino-4,5,6,7-tetrahydrobenzimidazole with bis(methylamide-R¹¹/R¹²) substituents]

wherein:

$R^{11}$ and $R^{12}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);

or an agriculturally acceptable salt thereof;

a compound of Formula (II)(c):

(II)(c)

[Structure: 2-amino-4,5,6,7-tetrahydrobenzimidazole with bis(methylsulfonamide-R¹³/R¹⁴) substituents]

wherein:

R[13] and R[14] are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);

or an agriculturally acceptable salt thereof;

a compound of Formula (III):

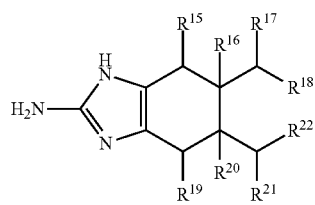

(III)

wherein:

R[15], R[16], R[17], R[18], R[19], R[20], R[21] and R[22] are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);

or an agriculturally acceptable salt thereof;

a compound of Formula (IV):

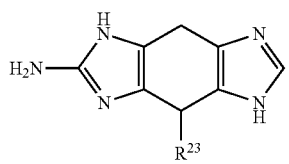

(IV)

wherein:

R[23] is selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);

or an agriculturally acceptable salt thereof;

a compound of Formula (V) or Formula (VI):

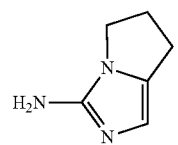

(V)

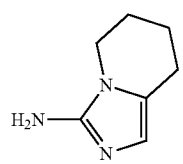

(VI)

(each formula can be optionally substituted);

or an agriculturally acceptable salt thereof;

a compound of Formula (X):

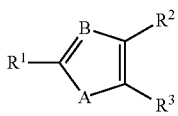

Formula (X)

wherein:

R[1] and R[2] and R[3] are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted); and A and B are each independently selected from N, S and O;

or an agriculturally acceptable salt thereof;

a compound of Formula (X)(I)(a):

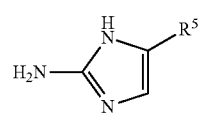

(X)(I)(a)

wherein R[5] is an alkyl, alkenyl or alkynyl having an amide group substituted thereon (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);

or an agriculturally acceptable salt thereof;

a compound of Formula (X)(I)(a)(1):

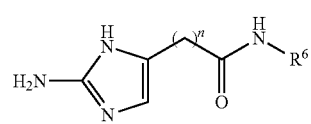

(X)(I)(a)(1)

wherein:

n is 1 to 10 carbons, saturated or unsaturated; and

R[6] is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);

or an agriculturally acceptable salt thereof;

a compound of Formula (X)(I)(a)(2):

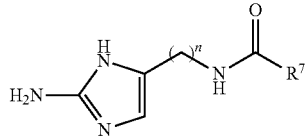

(X)(I)(a)(2)

wherein:
n is 1 to 10 carbons, saturated or unsaturated, substituted or unsubstituted; and
R⁷ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(a)(2)(A):

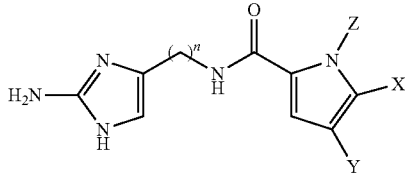

(X)(I)(a)(2)(A)

wherein:
n is 1 to 10 carbons, saturated or unsaturated, substituted or unsubstituted; and X, Y and Z are each independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(b):

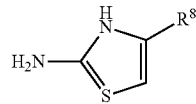

(X)(I)(b)

wherein R⁸ is an alkyl, alkenyl or alkynyl having an amide group substituted thereon (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(b)(1):

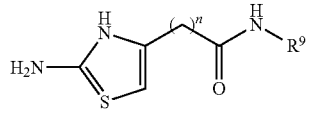

(X)(I)(b)(1)

wherein:
n is 1 to 10 carbons, saturated or unsaturated; and
R⁹ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(b)(2):

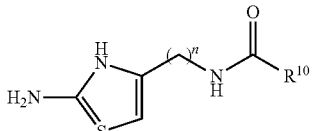

(X)(I)(b)(2)

wherein:
n is 1 to 10 carbons, saturated or unsaturated, substituted or unsubstituted; and
R¹⁰ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(b)(2)(A):

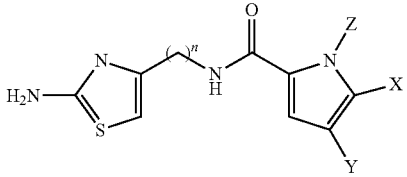

(X)(I)(b)(2)(A)

wherein:
n is 1 to 10 carbons, saturated or unsaturated, substituted or unsubstituted; and X, Y and Z are each independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);

or an agriculturally acceptable salt thereof;

a compound of Formula (X)(I)(c):

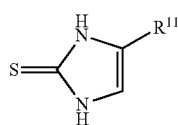

(X)(I)(c)

wherein $R^{11}$ is an alkyl, alkenyl or alkynyl having an amide group substituted thereon (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);

or an agriculturally acceptable salt thereof;

a compound of Formula (X)(I)(c)(1):

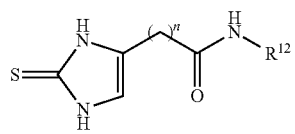

(X)(I)(c)(1)

wherein:

n is 1 to 10 carbons, saturated or unsaturated; and $R^{12}$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);

or an agriculturally acceptable salt thereof;

a compound of Formula (X)(I)(a)(2):

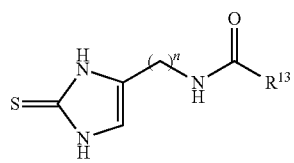

(X)(I)(c)(2)

wherein:

n is 1 to 10 carbons, saturated or unsaturated, substituted or unsubstituted; and $R^{13}$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);

or an agriculturally acceptable salt thereof;

a compound of Formula (X)(I)(c)(2)(A):

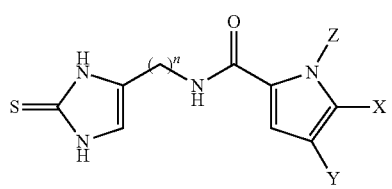

(X)(I)(c)(2)(A)

wherein:

n is 1 to 10 carbons, saturated or unsaturated, substituted or unsubstituted; and X, Y and Z are each independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);

or an agriculturally acceptable salt thereof.

In some embodiments, the microbicide comprises copper (e.g., copper hydroxide). In some embodiments, the microbicide is an antibiotic or a bacteriophage. In some embodiments, the applying step is carried out by applying the active compound and the microbicide simultaneously. In some embodiments, the applying step is carried out by applying the active compound and the microbicide sequentially. In some embodiments, the compound is a compound of Formula (II)(b)(vi)(trans)(±):

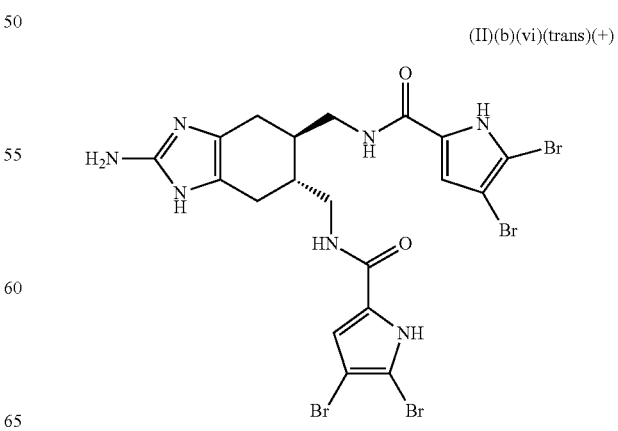

(II)(b)(vi)(trans)(+)

or an agriculturally acceptable salt thereof.

Also provided are methods of enhancing the effects of a plant defense activator comprising applying in combination with said plant defense activator an active compound selected from the group consisting of:

a compound of Formula (I):

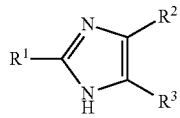

wherein:

$R^1$ and $R^2$ and $R^3$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);

or an agriculturally acceptable salt thereof;

a compound of Formula (I)(a):

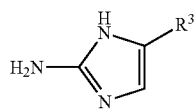

wherein:

$R^3$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide (each group can be optionally substituted);

or an agriculturally acceptable salt thereof;

a compound of Formula (II):

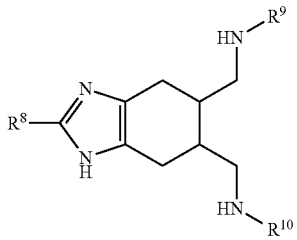

wherein:

$R^8$ is selected from the group consisting of: H, amino, hydroxy, and thiol; and $R^9$ and $R^{10}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);

or an agriculturally acceptable salt thereof;

a compound of Formula (II)(b):

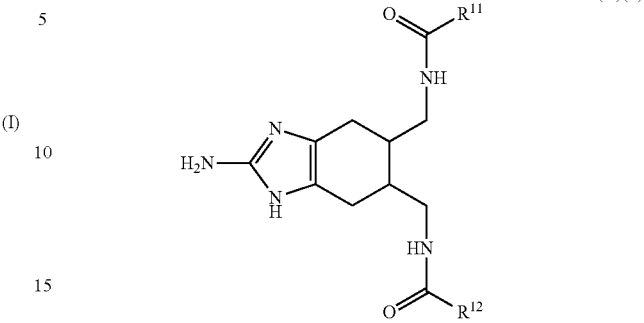

wherein:

$R^{11}$ and $R^{12}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);

or an agriculturally acceptable salt thereof;

a compound of Formula (II)(c):

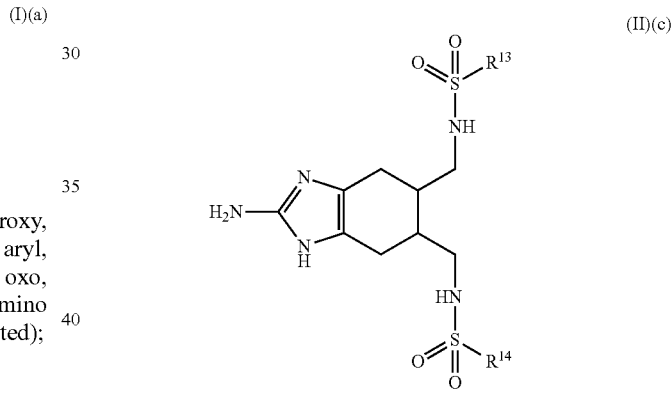

wherein:

$R^{13}$ and $R^{14}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);

or an agriculturally acceptable salt thereof;

a compound of Formula (III):

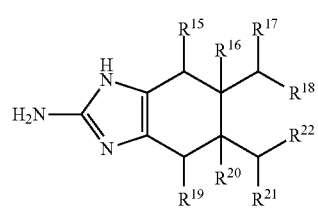

wherein:

$R^{15}$, $R^{16}$, $R^{17}$, $R^{18}$, $R^{19}$, $R^{20}$, $R^{21}$ and $R^{22}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);

or an agriculturally acceptable salt thereof;

a compound of Formula (IV):

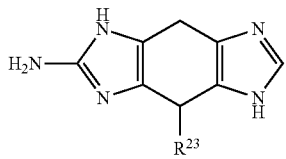

wherein:

$R^{23}$ is selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted);

or an agriculturally acceptable salt thereof;

a compound of Formula (V) or Formula (VI):

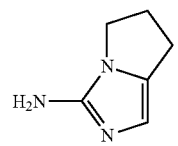

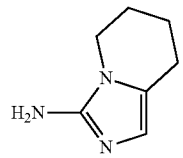

(each formula can be optionally substituted);

or an agriculturally acceptable salt thereof;

a compound of Formula (X):

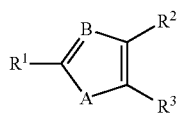

wherein:

$R^1$ and $R^2$ and $R^3$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (each group can be optionally substituted); and A and B are each independently selected from N, S and O;

or an agriculturally acceptable salt thereof;

a compound of Formula (X)(I)(a):

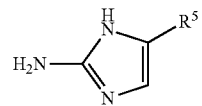

wherein $R^5$ is an alkyl, alkenyl or alkynyl having an amide group substituted thereon (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);

or an agriculturally acceptable salt thereof;

a compound of Formula (X)(I)(a)(1):

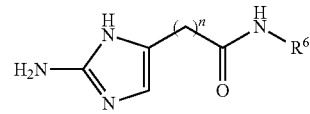

wherein:

n is 1 to 10 carbons, saturated or unsaturated; and $R^6$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);

or an agriculturally acceptable salt thereof;

a compound of Formula (X)(I)(a)(2):

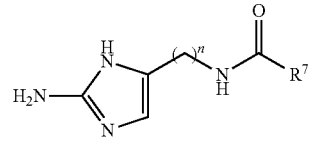

wherein:

n is 1 to 10 carbons, saturated or unsaturated, substituted or unsubstituted; and $R^7$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);

or an agriculturally acceptable salt thereof;

a compound of Formula (X)(I)(a)(2)(A):

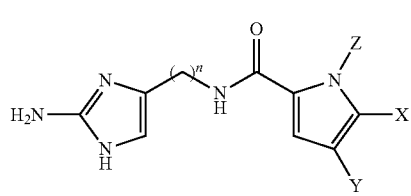

wherein:
n is 1 to 10 carbons, saturated or unsaturated, substituted or unsubstituted; and X, Y and Z are each independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(b):

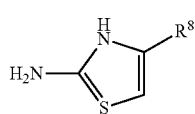

wherein $R^8$ is an alkyl, alkenyl or alkynyl having an amide group substituted thereon (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(b)(1):

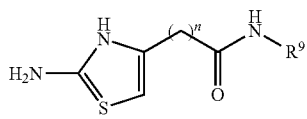

wherein:
n is 1 to 10 carbons, saturated or unsaturated; and
$R^9$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;

a compound of Formula (X)(I)(b)(2):

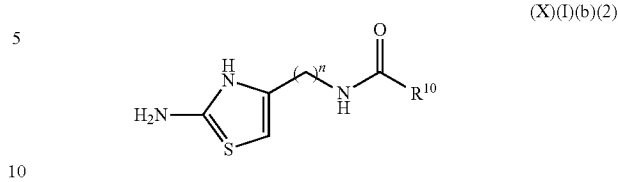

wherein:
n is 1 to 10 carbons, saturated or unsaturated, substituted or unsubstituted; and
$R^{10}$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(b)(2)(A):

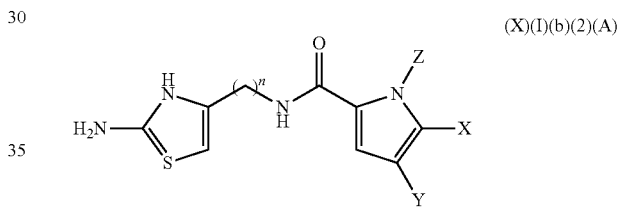

wherein:
n is 1 to 10 carbons, saturated or unsaturated, substituted or unsubstituted; and X, Y and Z are each independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(c):

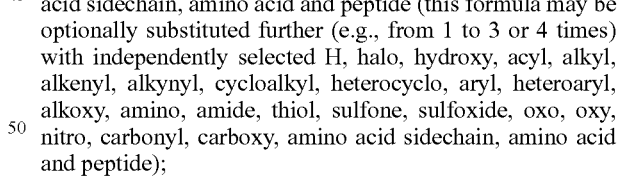

wherein $R^{11}$ is an alkyl, alkenyl or alkynyl having an amide group substituted thereon (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(c)(1):

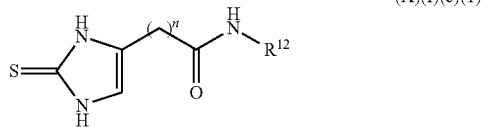

(X)(I)(c)(1)

wherein:
n is 1 to 10 carbons, saturated or unsaturated; and
$R^{12}$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(a)(2):

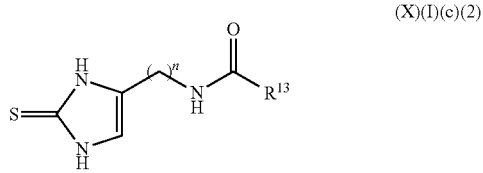

(X)(I)(c)(2)

wherein:
n is 1 to 10 carbons, saturated or unsaturated, substituted or unsubstituted; and
$R^{13}$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof;
a compound of Formula (X)(I)(c)(2)(A):

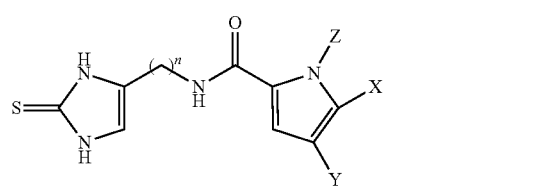

(X)(I)(c)(2)(A)

wherein:
n is 1 to 10 carbons, saturated or unsaturated, substituted or unsubstituted; and X, Y and Z are each independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide (this formula may be optionally substituted further (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide);
or an agriculturally acceptable salt thereof.

In some embodiments, the applying step is carried out by applying the active compound and the microbicide simultaneously. In some embodiments, the applying step is carried out by applying the active compound and the microbicide sequentially. In some embodiments, the compound is a compound of Formula (II)(b)(vi)(trans)(±):

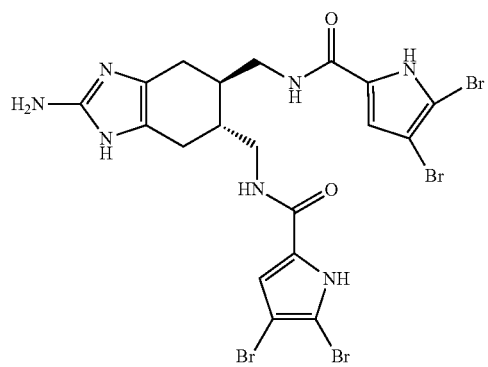

(II)(b)(vi)(trans)(±)

or an agriculturally acceptable salt thereof.

A further aspect of the present invention is an active compound as described herein, for use in treating or preventing a bacterial or fungal infection in a plant or plant part as described above and below.

DETAILED DESCRIPTION OF THE PREFERRED EMBODIMENTS

Figure 1:
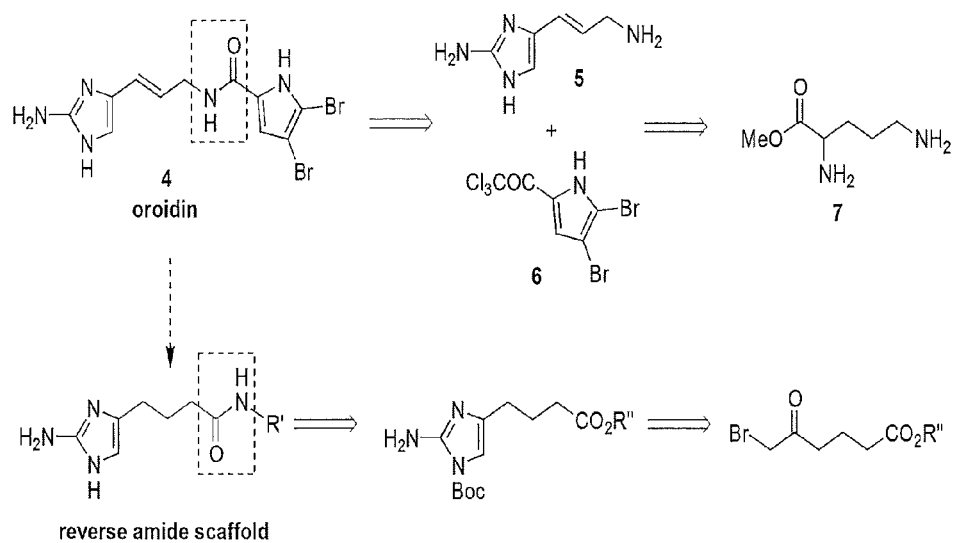
FIG. 1. Retrosynthetic analysis of oroidin and the RA scaffold.

The present invention is further described below. All patent references referred to in this patent application are hereby incorporated by reference in their entirety as if set forth fully herein.

A. Definitions.

"Plant" as used herein includes all members of the plant kingdom, including higher (or "vascular") plants and lower ("non-vascular") plants, and particularly including all plants in the divisions Filicinae, Gymnospermae (or "gymnosperm"), and Angiospermae (or "Angiosperm"). Nonvascular plants of the present invention include, but are not limited to, bryophytes.

A plant of the present invention includes, but is not limited to, a crop plant, a turf grass, an ornamental species, a species grown for timber or pulp, a species grown for biofuels or species grown for pharmaceuticals. Additionally, plants of the present invention include, but are not limited to, tobacco, tomato, potato, sugar beet, pea, carrot, cauliflower, broccoli, soybean, canola, sunflower, alfalfa, cotton, rapeseed, *Arabidopsis*, peach, pepper, apple, chile, peanut, orange, grape, coffee, cassaya, spinach, lettuce, cucumber, wheat, maize, rye, rice, turfgrass, oat, barley, sorghum, millet, sugarcane, or banana.

"Angiosperm" as used herein includes, but is not limited to, plants of the sub-classes Monocotyledoneae (or monocots) and Dicotyledoneae (or dicots).

Monocotyledoneae (or monocots) as used herein includes but is not limited to Amaryllidaceae—the Amaryllis Family, Gramineae (Poaceae)—the Grass Family, Liliaceae—the Lily Family, Orchidaceae—the Orchid Family, Palmae (Aracaceae)—the Palm Family; and Lemnacea—the duckweed family.

Dicotyledoneae (or dicots) as used herein includes but is not limited to Cactacae—the Cactus Family, Compositae (Asteraceae)—the Sunflower Family, Cruciferae (Brassicaceae)—the Mustard Family, Cucurbitaceae—the Gourd Family, Ericaceae—the Heath Family, Euphorbiaceae—the Spurge Family, Lauraceae—the Laurel Family, Leguminosae (Fabaceae)—the Pea Family, Rosaceae—the Rose Family, Rutaceae—the Rue Family, Solanaceae—the Nightshade Family, and Umbelliferae (Apiaceae)—the Carrot family.

Gymnospermae (or "Gymnosperms") as used herein includes but is not limited to conifers.

"Conifer," as used herein, refers to a member of the order Coniferae in the sub-phylum Gymnospermae in the phylum Spermaphyta. Exemplary conifers which may be used in practicing the present invention are the members of the family Pinaceae, which include, for example, loblolly pine (*Pinus taeda*), slash pine (*Pinus elliotii*), longleaf pine (*Pinus palustris*), shortleaf pine (*Pinus echinata*), ponderosa pine (*Pinus ponderosa*), red pine (*Pinus resinosa*), jack pine (*Pinus banksiana*), Eastern white pine (*Pinus strobus*), Western white pine (*Pinus monticola*), sugar pine (*Pinus lambertiana*), lodgepole pine (*Pinus contorta*), Monterey pine (*Pinus radiata*), Afghan pine (*Pinus eldarica*), Scots pine (*Pinus sylvestris*), and Virginia pine (*Pinus virginiana*); Douglas-fir (*Pseudotsuga menziesii*); Western hemlock (*Tsuga canadensis*); Sitka spruce (*Picea glauca*); redwood (*Sequoia sempervirens*); the true firs including silver fir (*Abies amabilis*), grand fir (*Abies grandis*) noble fir (*Abies procera*), white fir (*Abies concolor*), balsam fir (*Abies balsamea*); and the cedars which include Western red cedar (*Thuja plicata*), incense cedar (*Libocedrus decurrens*), Port Orford cedar (*Chamaecyparis lawsoniona*), and Alaska yellow-cedar (*Chamaecyparis nootkatensis*); and Western larch (*Laryx occidentalis*). See, e.g., U.S. Pat. No. 5,122,466 to Stomp et al.

"Duckweed" as used herein includes plants of the genus *Lemna* (*L. aequinoctialis, L. disperma, L. ecuadoriensis, L. gibba, L. japonica, L. minor, L. miniscula, L. obscura, L. perpusilla, L. tenera, L. trisulca, L. turionifera, L. valdiviana*); genus *Spirodela* (*S. intermedia, S. polyrrhiza, S. punctata*); genus *Wolffia* (*Wa. angusta, Wa. arrhiza, Wa. australina, Wa. borealis, Wa. brasiliensis, Wa. columbiana, Wa. elongata, Wa. globosa, Wa. microscopica, Wa. neglecta*) and genus *Wolfiella* (*Wl. caudata, Wl. denticulata, Wl. gladiata, Wl. hyalina, Wl. lingulata, Wl. repunda, Wl. rotunda*, and *Wl. neotropica*). See, e.g., U.S. Pat. No. 7,161,064 to Stomp et al.

Particular examples of plants include but are not limited to all cereal and grain crops, herbs and spices, oil seed crops, sugarcane, vegetable crops, *brassica* vegetables, bulb vegetables, cucurbit vegetables and fruit, leafy vegetables, fruiting vegetables, legume vegetables, root and tuber vegetables, tree, vine and shrub crops, berry crops, citrus (e.g., orange, grapefruit, Mandarin (including Tangerine and Satsuma), lemon, lime, and kumquat), pome fruit (e.g., apple, pear, quince, Asian pear, loquat, etc.), stone fruit (e.g., peach, apricot, prune, plum, cherries, almond, etc.), miscellaneous tree food crops, non-food tree crops, tree nuts, tropical and subtropical trees and fruit, vine crops, pasture grasses, forage legumes, and rangeland, grass seed or sod production, pastures, cotton, corn, soybeans, rice, wheat, greenhouse/shadehouse grown plants, ornamental, plant nurseries, Christmas trees, golf courses and turf, forestry, tobacco, orchids, flowers and roses, foliage crops, algae such as green algae, bryophytes (mosses, liverworts, hornworts), etc. Note that "foliage crops" refers to the types of plants (ferns, etc.) that are typically used in home or commercial settings for decorative purposes; this alone constitutes a very large commercial industry.

"Plant part" as used herein refers to seeds, roots, leaves, shoots, fruits (e.g., apples, pineapples, citrus fruit, etc.), vegetables, tubers, flowers (e.g., cut flowers such as roses, as well as the reproductive parts of plants), petals, stem, trunk, etc., harvested or collected from a plant as described herein. The plant part of a vascular plant may be a non-vascular part, such as a seed or meristem (growing tip of a shoot).

"Applying" as described herein can be carried out directly or indirectly by any suitable technique, including topically applying to the plant or plant part, applying to the media in which the plant or plant part is grown, stored, displayed or maintained (e.g., adding to water in which the stems of cut flowers are placed), etc. Note that the plant may be grown in any suitable media, including but not limited to soil, potting soil, soilless media such as sand and hydroponic media (including solution culture, medium culture, and deep water culture), etc.

"Agricultural composition" as described herein may be in any suitable form, including but not limited to: wettable powders, dry flowables, soluble powders, water dispersibles, liquids, dusts, emulsifiable concentrates, flowables, fumigants, water dispersable granules, liquid concentrates, granules, water soluble packages, wettable powders in water soluble films, emulsions, etc.

"Imidazole" refers to the commonly known structure:

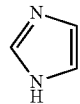

"H" refers to a hydrogen atom. "C" refers to a carbon atom. "N" refers to a nitrogen atom. "O" refers to an oxygen atom. "Halo" refers to F, Cl, Br or I. The term "hydroxy," as used herein, refers to an —OH moiety. "Br" refers to a bromine atom. "Cl" refers to a chlorine atom. "I" refers to an iodine atom. "F" refers to a fluorine atom.

An "acyl group" is intended to mean a —C(O)—R radical, where R is a suitable substituent (for example, an acetyl group, a propionyl group, a butyroyl group, a benzoyl group, or an alkylbenzoyl group).

"Alkyl," as used herein, refers to a straight or branched chain hydrocarbon containing from 1 or 2 to 10 or 20 or more carbon atoms (e.g., C2, C3, C4, C5, C6, C7, C8, C9, C10, C11, C12, C13, C14, C15, etc.). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. In some embodiments, alkyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

The term "optionally substituted" indicates that the specified group is either unsubstituted, or substituted by one or more suitable substituents. A "substituent" is an atom or atoms substituted in place of a hydrogen atom on the parent chain or cycle of an organic molecule, for example, H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Alkenyl," as used herein, refers to a straight or branched chain hydrocarbon containing from 1 or 2 to 10 or 20 or more carbons, and containing at least one carbon-carbon double bond, formed structurally, for example, by the replacement of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like. In some embodiments, alkenyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Alkynyl," as used herein, refers to a straight or branched chain hydrocarbon group containing from 1 or 2 to 10 or 20 or more carbon atoms, and containing at least one carbon-carbon triple bond. Representative examples of alkynyl include, but are not limited, to acetylenyl, 1-propynyl, 2-propynyl, 3-butynyl, 2-pentynyl, 1-butynyl and the like. In some embodiments, alkynyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

The term "cycloalkyl," as used herein, refers to a saturated cyclic hydrocarbon group containing from 3 to 8 carbons or more. Representative examples of cycloalkyl include, cyclopropyl, cyclobutyl, cyclopentyl, cyclohexyl, cycloheptyl, and cyclooctyl. In some embodiments, cycloalkyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Heterocyclo," as used herein, refers to a monocyclic or a bicyclic ring system. Monocyclic heterocycle ring systems are exemplified by any 5 or 6 member ring containing 1, 2, 3, or 4 heteroatoms independently selected from the group consisting of: O, N, and S. The 5 member ring has from 0 to 2 double bonds, and the 6 member ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, sulfoxide, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like.

"Aryl" as used herein refers to a fused ring system having one or more aromatic rings. Representative examples of aryl include, azulenyl, indanyl, indenyl, naphthyl, phenyl, tetrahydronaphthyl, and the like. The aryl groups of this invention can be substituted with 1, 2, 3, 4, or 5 substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, aryloxy, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, —NR'R" (wherein, R' and R" are independently selected from hydrogen, alkyl, alkylcarbonyl, aryl, arylalkyl and formyl), and —C(O)NR'R" (wherein R' and R" are independently selected from hydrogen, alkyl, alkylcarbonyl, aryl, arylalkyl, and formyl).

"Heteroaryl" means a cyclic, aromatic hydrocarbon in which one or more carbon atoms have been replaced with heteroatoms. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzo[b]thienyl. Preferred heteroaryl groups are five and six membered rings and contain from one to three heteroatoms independently selected from the group consisting of: O, N, and S. The heteroaryl group, including each heteroatom, can be unsubstituted or substituted with from 1 to 4 suitable substituents, as chemically feasible. For example, the heteroatom S may be substituted with one or two oxo groups, which may be shown as =O.

"Alkoxy," as used herein, refers to an alkyl group, as defined herein, appended to the parent molecular moiety through an oxy group, as defined herein. Representative examples of alkoxy include, but are not limited to, methoxy, ethoxy, propoxy, 2-propoxy, butoxy, tert-butoxy, pentyloxy, hexyloxy and the like. In some embodiments, alkoxy groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

An "amine" or "amino" group is intended to mean the radical —NH$_2$. "Optionally substituted" amines refers to —NH$_2$ groups wherein none, one or two of the hydrogens is replaced by a suitable substituent as described herein, such as alkyl, alkenyl, alkynyl, cycloalkyl, heterocyclo, aryl, heteroaryl, alkoxy, carbonyl, carboxy, etc. In some embodiments, one or two of the hydrogens are optionally substituted with independently selected, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide. Disubstituted amines may have substituents that are bridging, i.e., form a heterocyclic ring structure that includes the amine nitrogen.

An "amide" as used herein refers to an organic functional group having a carbonyl group (C=O) linked to a nitrogen atom (N), or a compound that contains this group, generally depicted as:

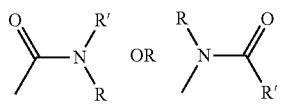

wherein, R and R' can independently be any covalently linked atom or atoms, for example, H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

A "thiol" or "mercapto" refers to an —SH group or to its tautomer =S.

A "sulfone" as used herein refers to a sulfonyl functional group, generally depicted as:

wherein, R can be any covalently linked atom or atoms, for example, H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

A "sulfoxide" as used herein refers to a sulfinyl functional group, generally depicted as:

wherein, R can be any covalently linked atom or atoms, for example, H, halohydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

The term "oxo," as used herein, refers to a =O moiety. The term "oxy," as used herein, refers to a —O— moiety.

"Nitro" refers to the organic compound functional group —NO$_2$.

"Carbonyl" is a functional group having a carbon atom double-bonded to an oxygen atom (—C=O). "Carboxy" as used herein refers to a —COOH functional group, also written as —(C=O)—OH.

"Amino acid sidechain" as used herein refers to any of the 20 commonly known groups associated with naturally occurring amino acids, or any natural or synthetic homologue thereof. An "amino acid" includes the sidechain group and the amino group, alpha-carbon atom, and carboxy groups, as commonly described in the art. Examples of amino acids include glycine, and glycine that is substituted with a suitable substituent as described herein, such as alkyl, alkenyl, alkynyl, cycloalkyl, heterocyclo, aryl, heteroaryl, alkoxy, carbonyl, carboxy, etc., or an agriculturally acceptable salt. For example, "Histidine" is one of the 20 most commonly known amino acids found naturally in proteins. It contains an imidazole side chain substituent. Other examples of naturally occurring amino acids include lysine, arginine, aspartic acid, glutamic acid, asparagine, glutamine, serine, threonine, tyrosine, alanine, valine, leucine, isoleucine, phenylalanine, methionine, cryptophan, and cysteine. Also included in the definitions of "amino acid sidechain" and "amino acid" is proline, which is commonly included in the definition of an amino acid, but is technically an imino acid. As used in this application, both the naturally occurring L-, and the non-natural D-amino acid enantiomers are included. A "peptide" is a linear chain of amino acids covalently linked together, typically through an amide linkage, and contains from 1 or 2 to 10 or 20 or more amino acids, and is also optionally substituted and/or branched.

"Agriculturally acceptable salt" is intended to mean a salt that retains the biological effectiveness of the free acids and bases of a specified compound and that is not biologically or otherwise undesirable. Examples of agriculturally acceptable salts include sulfates, pyrosulfates, bisulfates, sulfites, bisulfates, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methane-sulfonates, propanesulfonates, naphthalene-1-sulfonates, naphthalene-2-sulfonates, and mandelates.

The term "optionally substituted" indicates that the specified group is either unsubstituted, or substituted by one or more suitable substituents. A "substituent" is an atom or atoms substituted in place of a hydrogen atom on the parent chain or cycle of an organic molecule.

B. Active Compounds.

In some of the embodiments provided in the present invention, active compounds are provided. These active compounds are derivatives of imidazole. Active compounds as described herein can be prepared as detailed below or in accordance with known procedures or variations thereof that will be apparent to those skilled in the art. See also U.S. Patent Application Publication No. 2008/0181923, which is incorporated by reference herein.

As will be appreciated by those of skill in the art, the active compounds of the various formulas disclosed herein may contain chiral centers, e.g. asymmetric carbon atoms. Thus, the present invention is concerned with the synthesis of both: (i) racemic mixtures of the active compounds, and (ii) enantiomeric forms of the active compounds. The resolution of racemates into enantiomeric forms can be done in accordance with known procedures in the art. For example, the racemate may be converted with an optically active reagent into a diastereomeric pair, and the diastereomeric pair subsequently separated into the enantiomeric forms.

Geometric isomers of double bonds and the like may also be present in the compounds disclosed herein, and all such stable isomers are included within the present invention unless otherwise specified. Also included in active compounds of the invention are tautomers (e.g., tautomers of imidazole) and rotamers.

Active compounds for carrying out the present invention include compounds of Formula (I):

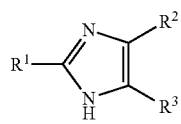

(I)

wherein:

$R^1$ and $R^2$ and $R^3$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or an agriculturally acceptable salt. Each group can be optionally substituted.

In some embodiments of Formula (I), $R^1$ is an amino and $R^2$ is H, depicted as Formula

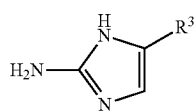

(I)(a)

wherein:

$R^3$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

or an agriculturally acceptable salt. Each group can be optionally substituted.

In some embodiments of Formula (I)(a), $R^3$ comprises an amino acid sidechain. Examples of these embodiments are depicted in Formulas (I)(a)(i)-(I)(a)(ix):

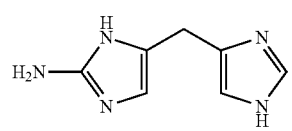

(I)(a)(i)

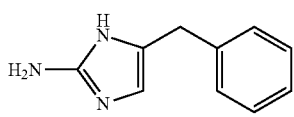

(I)(a)(ii)

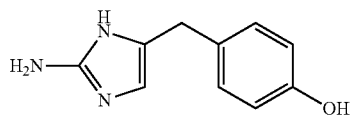

(I)(a)(iii)

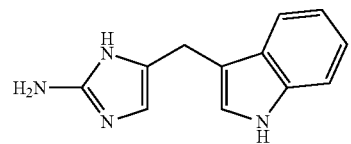

(I)(a)(iv)

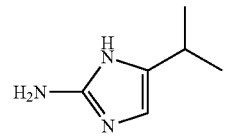

(I)(a)(v)

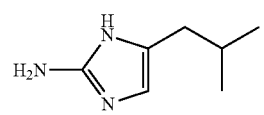

(I)(a)(vi)

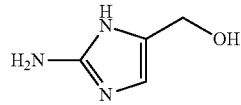

(I)(a)(vii)

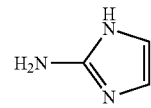

(I)(a)(viii)

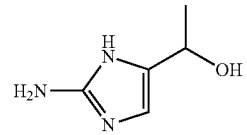

(I)(a)(ix)

In some embodiments of Formula (I)(a), $R^3$ comprises amino alkanes or amino alkenes. Examples of these embodiments are depicted in (I)(a)(xi)-(I)(a)(xiv):

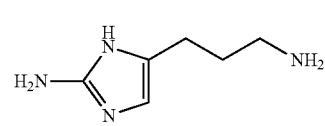

(I)(a)(xi)

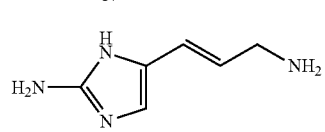

(I)(a)(xii)

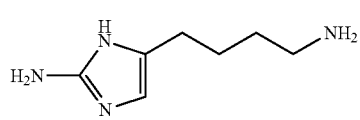

(I)(a)(xiii)

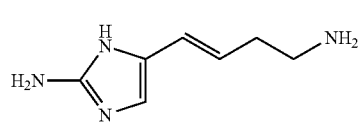

(I)(a)(xiv)

In some embodiments of Formula (I)(a), R³ comprises an alkyl or alkenyl with disubstituted amides. Examples of these embodiments are depicted in Formulas (I)(a)(xv)-(I)(a)(xviii):

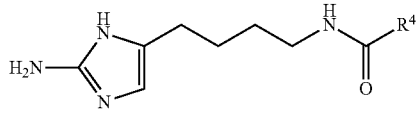
(I)(a)(xv)

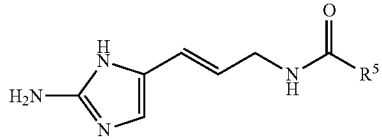
(I)(a)(xvi)

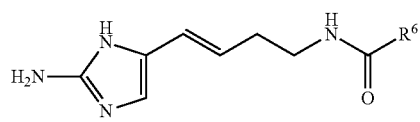
(I)(a)(xvii)

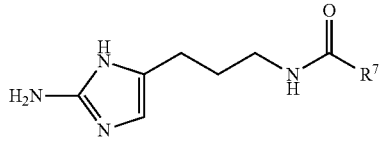
(I)(a)(xviii)

wherein:
R⁴, R⁵, R⁶, and R⁷ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

or an agriculturally acceptable salt. Each group can be optionally substituted.

In some embodiments of Formulas (I)(a)(xv)-(I)(a)(xviii), R⁴, R⁵, R⁶, and R⁷ comprise aryls or heteroaryls. Examples of these embodiments include those aryls and heteroaryls depicted in Formulas (II)(b)(i)-(II)(b)(ix) below for constituents R¹¹ and R¹².

In some embodiments of Formula (I)(a), R³ comprises alkyls with heterocycloalkyls, optionally substituted with further alkyls or alkenyls. Examples of these embodiments are depicted in Formulas (I)(a)(xix)-(I)(a)(xx):

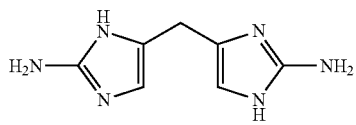
(I)(a)(xix)

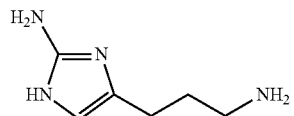
(I)(a)(xx)

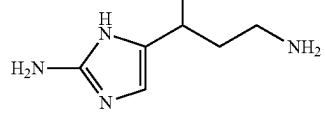

Active compounds for carrying out the present invention include compounds of Formula (II):

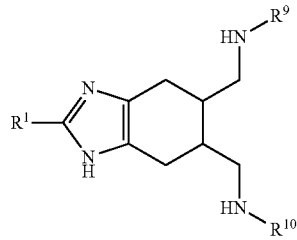
(II)

wherein:
R⁸ is selected from the group consisting of: H, amino, hydroxy, and thiol; and
R⁹ and R¹⁰ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or an agriculturally acceptable salt. Each group can be optionally substituted.

Some embodiments of the active compounds comprise derivatives of 2-aminoimidazole. For example, in some embodiments of Formula (II), R⁸ comprises an amino, R⁹ and R¹⁰ are the same, and R⁹ and R¹⁰ comprise H. Examples of these embodiments are depicted in Formula (II)(a):

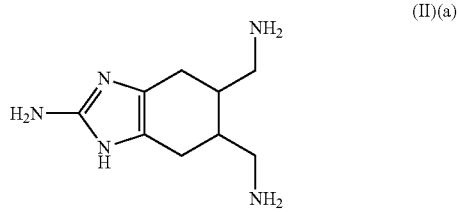
(II)(a)

Examples of certain stereoisomers of Formula (II)(a) include those depicted in Formulas (II)(a)(i)-(II)(a)(ii):

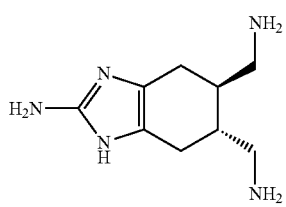
(II)(a)(i)

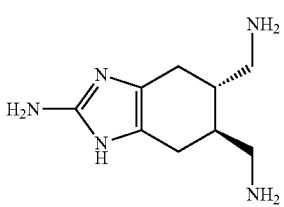
(II)(a)(ii)

The discussion herein is, for simplicity, given without further reference to stereoisomerism. However, as noted above, the active compounds of the various formulas disclosed herein contain chiral centers, e.g. asymmetric carbon atoms. Thus, the present invention is concerned with the synthesis of both: (i) racemic mixtures of the active compounds, and (ii)

enantiomeric forms of the active compounds. A racemic mixture of an active compound having chiral centers may also be depicted by "(±)" as is understood by those of skill in the art.

The resolution of racemates into enantiomeric forms can be done in accordance with known procedures in the art. For example, the racemate may be converted with an optically active reagent into a diastereomeric pair, and the diastereomeric pair subsequently separated into the enantiomeric forms.

In some embodiments of Formula (II), $R^8$ comprises an amino, and $R^9$ and $R^{10}$ comprise carbonyls, generally depicted in Formula (II)(b):

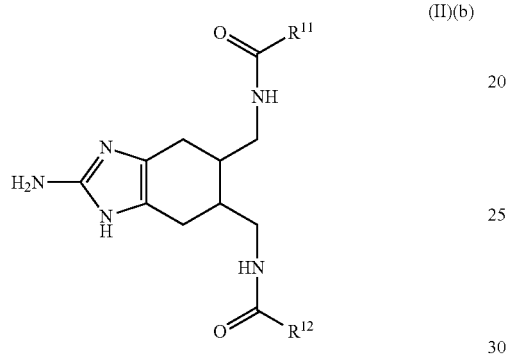

(II)(b)

wherein:

$R^{11}$ and $R^{12}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or an agriculturally acceptable salt. Each group can be optionally substituted.

In some embodiments of Formula (II)(b), $R^{11}$ and $R^{12}$ are the same, and $R^{11}$ and $R^{12}$ comprise aryls or heteroaryls. Examples of these embodiments are depicted in Formulas (II)(b)(i)-(II)(b)(ix):

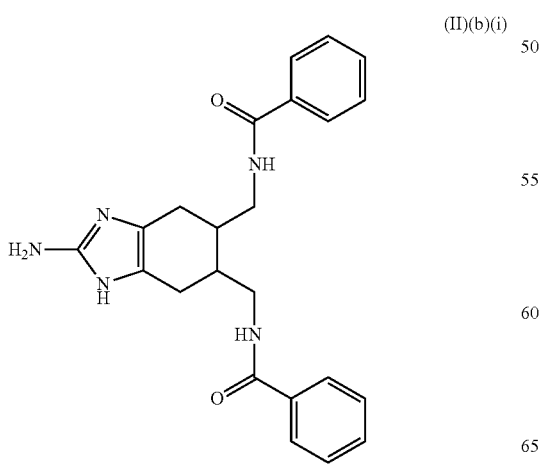

(II)(b)(i)

-continued

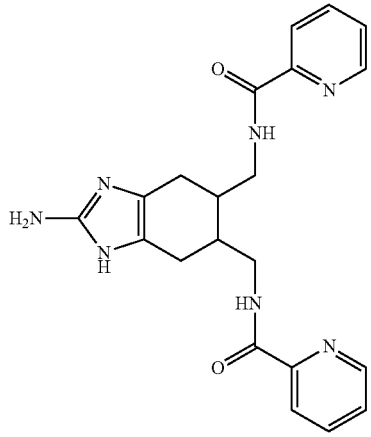

(II)(b)(ii)

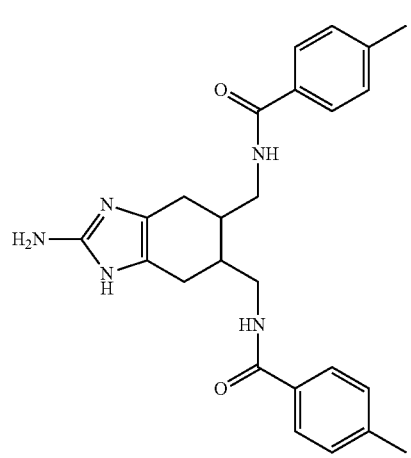

(II)(b)(iii)

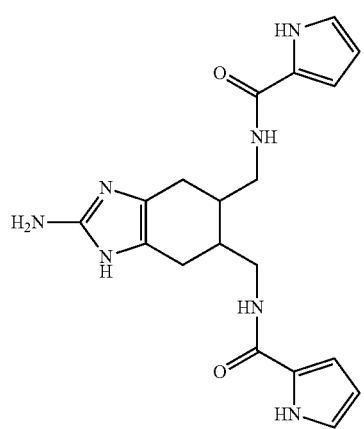

(II)(b)(iv)

(II)(b)(v)
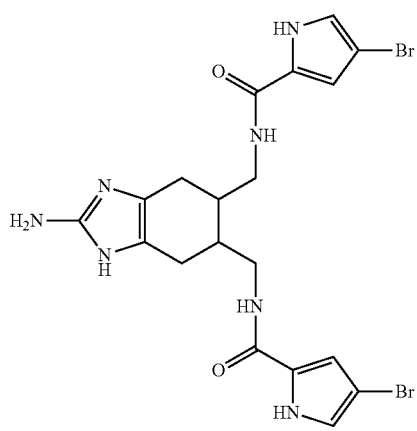
(II)(b)(viii)
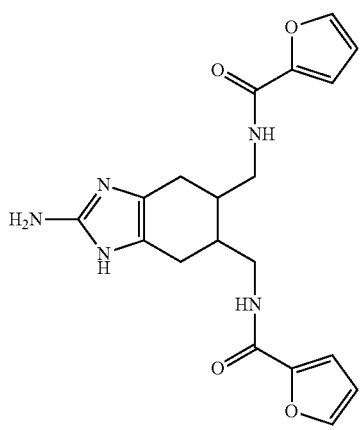
(II)(b)(vi)
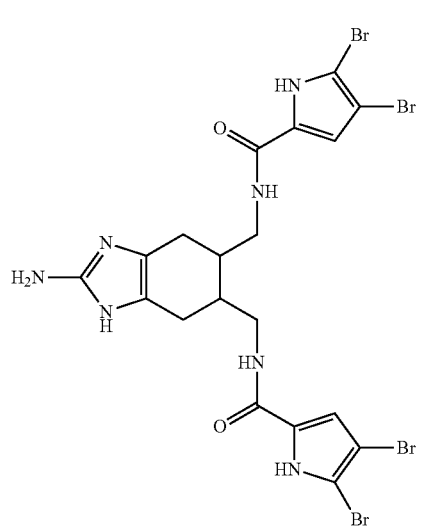
(II)(b)(ix)
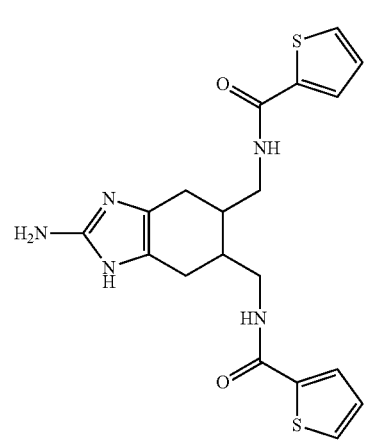
In some embodiments, two asymmetric carbon atoms are in a trans configuration. An example includes Formula (II)(b)(vi)(trans)(±) and Formula (II)(b)(v)(trans)(±):
(II)(b)(vii)
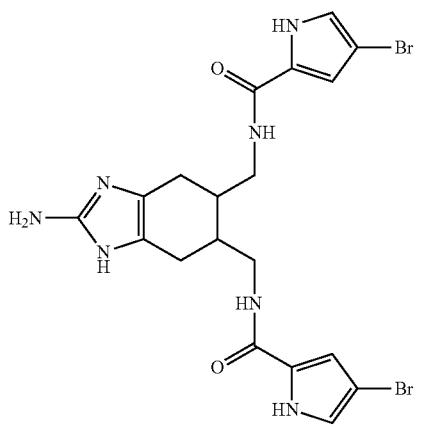
(II)(b)(vi)(trans)(±)
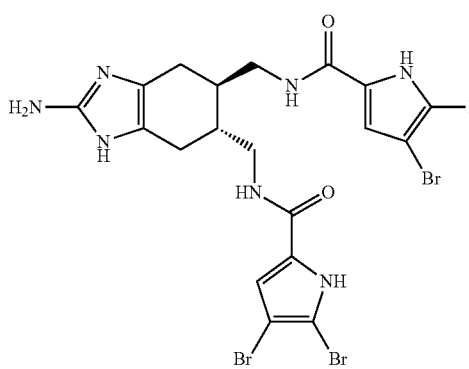

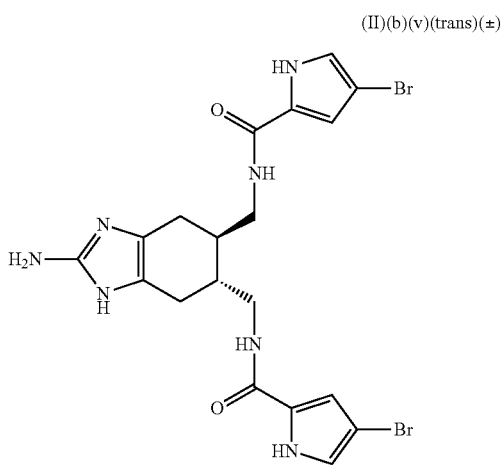

(II)(b)(v)(trans)(±)

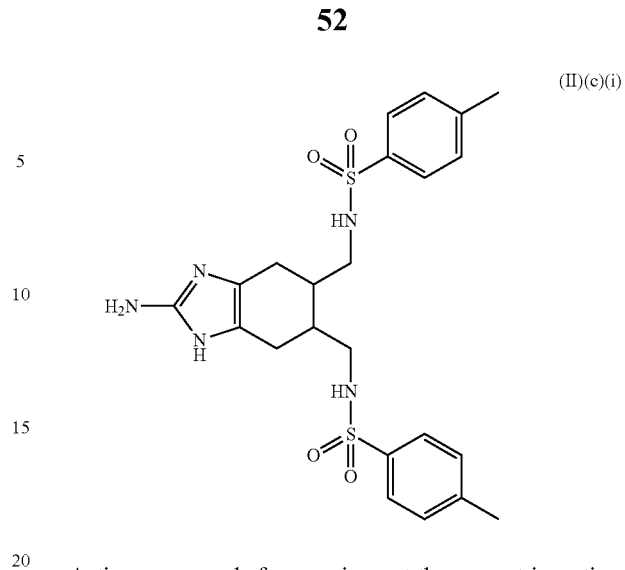

(II)(c)(i)

Active compounds for carrying out the present invention include compounds of Formula (III):

As would be understood by one of skill in the art, these formulas refer to a racemic mixture ("(±)") of these compounds.

In some embodiments of Formula (II), $R^8$ comprises an amino, $R^9$ and $R^{10}$ are the same, and $R^9$ and $R^{10}$ comprise sulfones, generally depicted in Formula (II)(c):

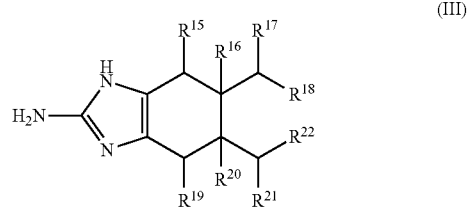

(III)

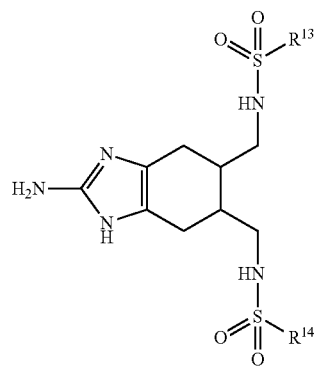

(II)(c)

wherein:

$R^{15}, R^{16}, R^{17}, R^{18}, R^{19}, R^{20}, R^{21}$ and $R^{22}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or an agriculturally acceptable salt. Each group can be optionally substituted.

Active compounds for carrying out the present invention include compounds of Formula (IV):

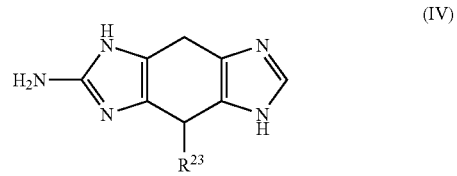

(IV)

wherein:

$R^{23}$ is selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or an agriculturally acceptable salt. Each group can be optionally substituted.

In some embodiments of Formula (IV), $R^{23}$ comprises an amino acid sidechain. Examples of these embodiments are depicted in Formula (IV)(a) through Formula (IV)(c). The amino acids or peptides are optionally substituted, exemplified in Formula (IV)(d):

wherein:

$R^{13}$ and $R^{14}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or an agriculturally acceptable salt. Each group can be optionally substituted.

In some embodiments of Formula (II)(c), $R^{13}$ and $R^{14}$ are the same, and $R^{13}$ and $R^{14}$ comprise aryls or heteroaryls. An example of these embodiments is depicted in Formula (II)(c)(i):

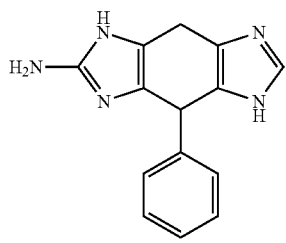
(IV)(a)

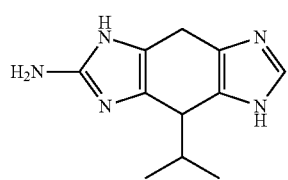
(IV)(b)

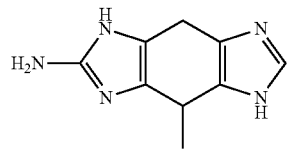
(IV)(c)

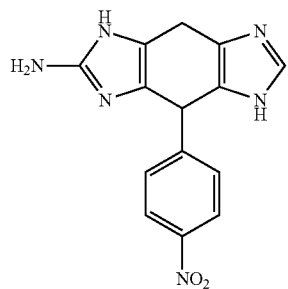
(IV)(d)

Active compound embodiments include those depicted by Formula (V) and Formula (VI):

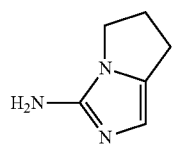
(V)

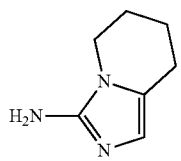
(VI)

These formulas are also optionally substituted.

Active compounds also include those represented by Formula (X):

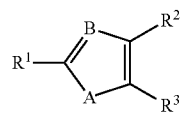
Formula (X)

wherein:

$R^1$ and $R^2$ and $R^3$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and A and B are each independently selected from N, S and O.

or an agriculturally acceptable salt. Each group can be optionally substituted.

In some embodiments of Formula (X), $R^1$ is amino; $R^3$ is H; and A and B are each N, generally depicted by Formula (X)(I)(a):

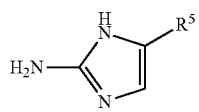
(X)(I)(a)

wherein $R^5$ is an alkyl, alkenyl or alkynyl having an amide group substituted thereon;

or an agriculturally acceptable salt.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(a) are represented by Formula (X)(I)(a)(1):

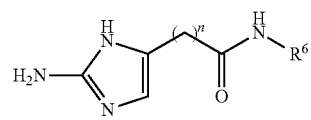
(X)(I)(a)(1)

wherein:

n is 1 to 10 carbons, saturated or unsaturated; and $R^6$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or an agriculturally acceptable salt.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

A preferred embodiment of Formula (X)(I)(a) is represented by Formula (X)(I)(a)(1)(A):

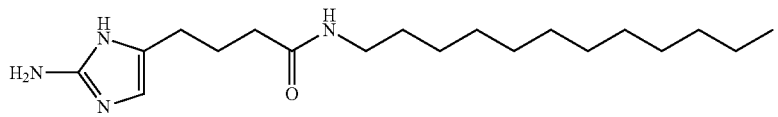

or an agriculturally acceptable salt.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(a) are represented by Formula (X)(I)(a)(2):

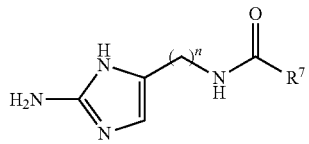

wherein:
n is 1 to 10 carbons, saturated or unsaturated, substituted or unsubstituted; and
$R^7$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;
or an agriculturally acceptable salt.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(a)(2) are represented by Formula (X)(I)(a)(2)(A):

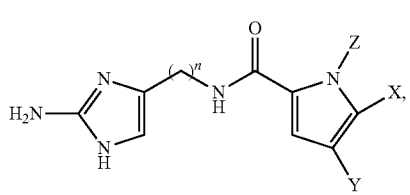

wherein:
n is 1 to 10 carbons, saturated or unsaturated, substituted or unsubstituted; and X, Y and Z are each independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;
or an agriculturally acceptable salt.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(a)(2)(A) are represented by Formula (x)(I)(a)(2)(A)(i):

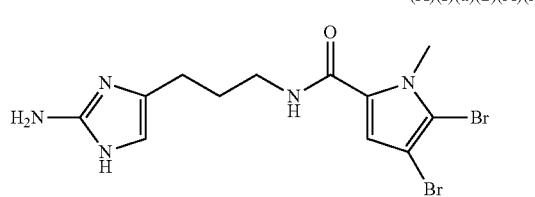

or an agriculturally acceptable salt.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (X), $R^1$ is amino; $R^3$ is H; and A is S and B is N, generally depicted by Formula (X)(I)(b):

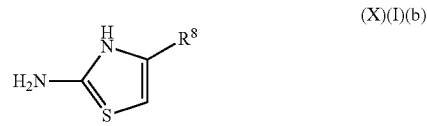

wherein $R^8$ is an alkyl, alkenyl or alkynyl having an amide group substituted thereon;
or an agriculturally acceptable salt.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(b) are represented by Formula (X)(I)(b)(1):

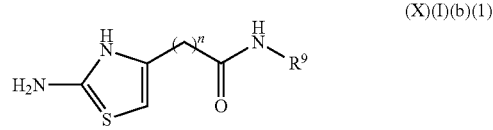

wherein:
n is 1 to 10 carbons, saturated or unsaturated; and
$R^9$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or an agriculturally acceptable salt.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

A preferred embodiment of Formula (X)(I)(b) is represented by Formula (X)(I)(b)(1)(A):

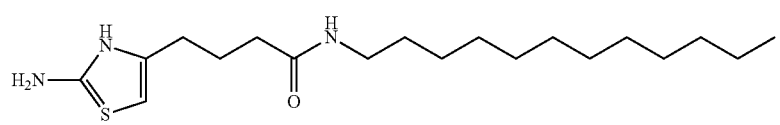

(X)(I)(b)(1)(A)

or an agriculturally acceptable salt.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(b) are represented by Formula (X)(I)(b)(2):

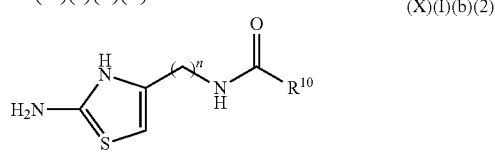

(X)(I)(b)(2)

wherein:

n is 1 to 10 carbons, saturated or unsaturated, substituted or unsubstituted; and $R^{10}$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or an agriculturally acceptable salt.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(b)(2) are represented by Formula (X)(I)(b)(2)(A):

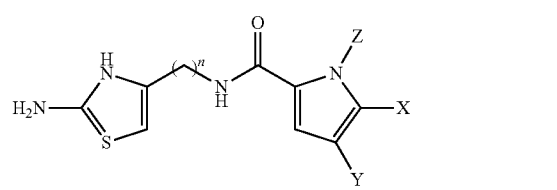

(X)(I)(b)(2)(A)

wherein:

is 1 to 10 carbons, saturated or unsaturated, substituted or unsubstituted; and X, Y and Z are each independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or an agriculturally acceptable salt.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(b)(2)(A) are represented by Formula (X)(I)(b)(2)(A)(i):

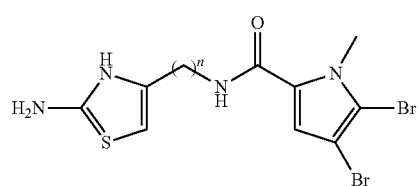

(X)(I)(b)(2)(A)(i)

or an agriculturally acceptable salt.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (X), $R^1$ is thiol; $R^3$ is H; and A and B are each N, generally depicted by Formula (X)(I)(c):

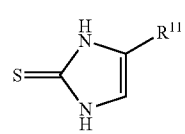

(X)(I)(c)

wherein $R^{11}$ is an alkyl, alkenyl or alkynyl having an amide group substituted thereon;

or an agriculturally acceptable salt.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(c) are represented by Formula (X)(I)(c)(1):

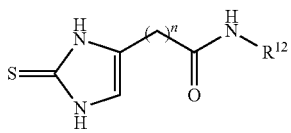

wherein:
n is 1 to 10 carbons, saturated or unsaturated; and
$R^{12}$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;
or an agriculturally acceptable salt.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

A preferred embodiment of Formula (X)(I)(c) is represented by Formula (x)(I)(c)(1)(A):

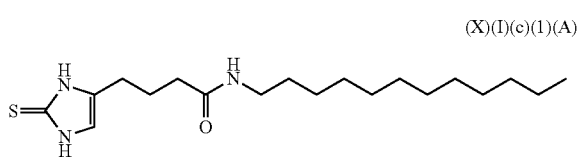 [SMILES: CCCCCCCCCCCCNC(=O)CCCc1c[nH]c(=S)[nH]1]

or an agriculturally acceptable salt.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(a) are represented by Formula (X)(I)(a)(2):

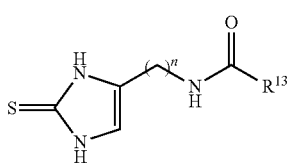

wherein:
n is 1 to 10 carbons, saturated or unsaturated, substituted or unsubstituted; and
$R^{13}$ is selected from the group consisting of H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;
or an agriculturally acceptable salt.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(c)(2) are represented by Formula (x)(I)(c)(2)(A):

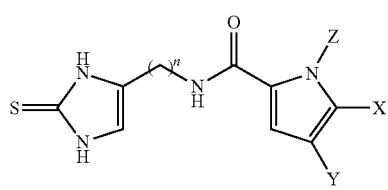

wherein:
n is 1 to 10 carbons, saturated or unsaturated, substituted or unsubstituted; and X, Y and Z are each independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;
or an agriculturally acceptable salt.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Some embodiments of Formula (X)(I)(c)(2)(A) are represented by Formula (x)(I)(c)(2)(A)(i):

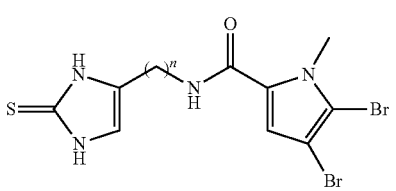

or an agriculturally acceptable salt.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

C. Microbicides And Plant Defense Activators.

In some embodiments, an active compound described herein is applied in combination with a microbicide. "Microbicide" as used herein refers to a substance with the ability to kill or to inhibit the growth of microorganisms (e.g., bacteria, fungal cells, protozoa, etc.), which microbicide is not an active compound in the group herein disclosed of triazole derivatives. Common microbicides used for microbial control in plants include copper compounds. Examples of copper compounds include, but are not limited to, Bordeaux mixture, copper hydroxide, copper oxychloride, copper sulfate, cuprous oxide, mancopper or oxine-copper. However, microorganisms (e.g., bacteria such as *Xanthomonas* and *Pseudomonas*) may become resistant to treatment with copper.

In some embodiments, resistant microorganisms (e.g., copper-resistant bacteria) are rendered more susceptible to a microbicides and/or the effectiveness of treatment with a microbicides is enhanced upon application in combination with an active compound described herein (e.g., fruit or vegetable yield is increased as compared to diseased plant producing the fruit or vegetable that is untreated or treated only with the microbicide).

Other microbicides include, but are not limited to, azoles such as azaconazole, bitertanol, propiconazole, difenoconazole, diniconazole, cyproconazole, epoxiconazole, fluquinconazole, flusilazole, flutriafol, hexaconazole, imazalil, imibenconazole, ipconazole, tebuconazole, tetraconazole, fenbuconazole, metconazole, myclobutanil, perfurazoate, penconazole, bromuconazole, pyrifenox, prochloraz, triadimefon, triadimenol, triflumizole or triticonazole; pyrimidinyl carbinoles such as ancymidol, fenarimol or nuarimol; 2-amino-pyrimidine such as bupirimate, dimethirimol or ethirimol; morpholines such as dodemorph, fenpropidin, fenpropimorph, spiroxamin or tridemorph; anilinopyrimidines such as cyprodinil, pyrimethanil or mepanipyrim; pyrroles such as fenpiclonil or fludioxonil; phenylamides such as benalaxyl, furalaxyl, metalaxyl, R-metalaxyl, ofurace or oxadixyl; benzimidazoles such as benomyl, carbendazim, debacarb, fuberidazole or thiabendazole; dicarboximides such as chlozolinate, dichlozoline, iprodine, myclozoline, procymidone or vinclozolin; carboxamides such as carboxin, fenfuram, flutolanil, mepronil, oxycarboxin or thifluzamide; guanidines such as guazatine, dodine or iminoctadine; strobilurines such as azoxystrobin, kresoxim-methyl, metominostrobin, SSF-129, methyl 2[(2-trifluoromethyl)-pyrid-6-yloxymethyl]-3-methoxy-acrylate or 2-[{α[(α-methyl-3-trifluoromethyl-benzyl)imino]-oxy}-o-tolyl]-1-glyoxylic acid-methylester-O-methyloxime (trifloxystrobin); dithiocarbamates such as ferbam, mancozeb, maneb, metiram, propineb, thiram, zineb or ziram; N-halomethylthio-dicarboximides such as captafol, captan, dichlofluanid, fluoromide, folpet or tolyfluanid; nitrophenol derivatives such as dinocap or nitrothal-isopropyl; organo phosphorous derivatives such as edifenphos, iprobenphos, isoprothiolane, phosdiphen, pyrazophos or toclofos-methyl; and other compounds of diverse structures such as acibenzolar-5-methyl, hatpin, anilazine, blasticidin-S, chinomethionat, chloroneb, chlorothalonil, cymoxanil, dichione, diclomezine, dicloran, diethofencarb, dimethomorph, dithianon, etridiazole, famoxadone, fenamidone, fentin, ferimzone, fluazinam, flusulfamide, fenhexamid, fosetyl-aluminium, hymexazol, kasugamycin, methasulfocarb, pencycuron, phthalide, polyoxins, probenazole, propamocarb, pyroquilon, quinoxyfen, quintozene, sulfur, triazoxide, tricyclazole, triforine, validamycin, (S)-5-methyl-2-methylthio-5-phenyl-3-phenyl amino-3,5-di-hydroimidazol-4-o-ne (RPA 407213), 3,5-dichloro-N-(3-chloro-1-ethyl-1-methyl-2-oxopropyl)-4-methylbenzamide (RH-7281), N-allyl-4,5-dimethyl-2-trimethylsilylthiophene-3-carboxamide (MON 65500), 4-chloro-4-cyano-N,N-dimethyl-5-p-tolylimidazole-1-sulfon-amide (IKF-916), N-(1-cyano-1,2-dimethylpropyl)-2-(2,4-dichlorophenoxy)-propionamide (AC 382042) or iprovalicarb (SZX 722).

An "antibiotic" as used herein is a type of "microbicide." Common antibiotics include aminoglycosides, carbacephems (e.g., loracarbef), carbapenems, cephalosporins, glycopeptides (e.g., teicoplanin and vancomycin), macrolides, monobactams (e.g., aztreonam) penicillins, polypeptides (e.g., bacitracin, colistin, polymyxin B), quinolones, sulfonamides, tetracyclines, etc. Antibiotics treat infections by either killing or preventing the growth of microorganisms. Many act to inhibit cell wall synthesis or other vital protein synthesis of the microorganisms.

Aminoglycosides are commonly used to treat infections caused by Gram-negative bacteria. Examples of aminoglycosides include, but are not limited to amikacin, gentamicin, kanamycin, neomycin, netilmicin, streptomycin, tobramycin, and paromomycin.

Carbapenems are broad-specrum antibiotics, and include, but are not limited to, ertapenem, doripenem, imipenem/cilstatin, and meropenem.

Cephalosporins include, but are not limited to, cefadroxil, cefazolin, cefalotin (cefalothin), cefalexin, cefaclor, cefamandole, cefoxitin, cefprozil, loracarbef, cefuroxime, cefixime, cefdinir, cefditoren, cefoperazone, cefotaxime, cefpodoxime, ceftazidime, ceftibuten, ceftizoxime, ceftriaxone, cefepime, cefpirome, and ceftobiprole.

Macrolides include, but are not limited to, azithromycin, clarithromycin, dirithromycin, erythromycin, roxithromycin, troleandomycin, telithromycin and spectinomycin.

Penicillins include, but are not limited to, amoxicillin, ampicillin, azlocillin, bacampicillin, carbenicillin, cloxacillin, dicloxacillin, flucloxacillin, mezlocillin, meticillin, nafcillin, oxacillin, penicillin, piperacillin and ticarcillin.

Quinolones include, but are not limited to, ciprofloxacin, enoxacin, gatifloxacin, gemifloxacin, levofloxacin, lomefloxacin, moxifloxacin, norfloxacin, ofloxacin and trovafloxacin.

Sulfonamides include, but are not limited to, mafenide, prontosil, sulfacetamide, sulfamethizole, sulfanilamide, sulfasalazine, sulfisoxazole, trimethoprim, and co-trimoxazole (trimethoprim-sulfamethoxazole).

Tetracyclines include, but are not limited to, demeclocycline, doxycycline, minocycline, oxytetracycline and tetracycline.

Other antibiotics include arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin (rifampicin), timidazole, etc.

Other microbicides that may be used in combination with the active compounds of the present invention include bacteriophages (bacterial viruses) such as *Bacillus*. Examples of bacteriophage microbicides include, but are not limited to, AgriPhage™ (OmniLytics, Inc., Salt Lake City, Utah) and Serenade® (AgraQuest, Davis, Calif.). See, e.g., U.S. Pat. Nos. 5,919,447 and 6,077,506 to Marrone et al.; U.S. Pat. No. 6,103,228 to Heins et al.; and U.S. Patent Application Publication 20080152684.

In some embodiments, an active compound described herein is applied in combination with a plant defense activator. A "plant defense activator" as used herein is a compound that improves disease resistance by activating a plant's natural defense mechanisms, e.g., induces the plant to produce disease-fighting compounds. Examples of plant defense activators include, but are not limited to, prohexadione-calcium (Apogee), Cropset (plant booster element complex), probenazole, potassium phosphate (e.g., ProPhyt®, Helena Chemical Company), harpin protein (e.g., Messenger®, Eden Biosciences Ltd, Bothell, Wash.), acibenzolar or acibenzolar-S-methyl (e.g., Actigard™, Syngenta Crop Production, Inc, Greensboro, N.C.), streptomycin sulfate, reynoutria sachalinensis extract (reysa), etc.

D. Agrochemical Compositions.

Active compounds of the present invention can be used to prepare agrochemical compositions in like manner as other antimicrobial compounds. See, e.g., U.S. Pat. Application 2006/0094739; see also U.S. Pat. Nos. 6,617,330; 6,616,952; 6,569,875; 6,541,500, and 6,506,794.

Active compounds described herein can be used for protecting plants against diseases that are caused by microorganisms, including biofilm-forming microorganisms. The active compounds can be used in the agricultural sector and related fields as active ingredients for controlling plant pests. The active compounds can be used to inhibit or destroy the pests that occur on plants or parts of plants (fruit, blossoms, leaves, stems, tubers, roots) of different crops of useful plants, optionally while at the same time protecting also those parts of the plants that grow later e.g. from phytopathogenic microorganisms.

Active compounds may be used as dressing agents for the treatment of plant propagation material, in particular of seeds (fruit, tubers, grains) and plant cuttings (e.g. rice), for the protection against fungal infections as well as against phytopathogenic fungi occurring in the soil.

The active compounds can be used in the form of compositions and can be applied to the crop area or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides, plant growth regulators, plant activators or mixtures of several of these preparations, if desired together with further carriers, surfactants or application promoting adjuvants customarily employed in the art of formulation.

Suitable carriers and adjuvants can be solid or liquid and are substances useful in formulation technology, e.g. natural or regenerated mineral substances, solvents, dispersants, wetting agents, tackifiers, thickeners, binders or fertilizers.

The active compounds are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomizing, dusting, scattering, coating or pouring, are chosen in accordance with the intended objectives and the prevailing circumstances.

The formulation, i.e. the compositions containing the active compound and, if desired, a solid or liquid adjuvant, are prepared in known manner, typically by intimately mixing and/or grinding the compound with extenders, e.g. solvents, solid carriers and, optionally, surface active compounds (surfactants).

Suitable carriers and adjuvants may be solid or liquid and correspond to the substances ordinarily employed in formulation technology, such as, e.g. natural or regenerated mineral substances, solvents, dispersants, wetting agents, tackifiers, thickeners, binding agents or fertilizers. Such carriers are for example described in WO 97/33890.

Further surfactants customarily employed in the art of formulation are known to the expert or can be found in the relevant literature.

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

The compositions may also contain further adjuvants such as stabilizers, antifoams, viscosity regulators, binders or tackifiers as well as fertilizers, micronutrient donors or other formulations for obtaining special effects.

E. Methods Of Use.

Target crops or plants to be treated with active compounds and compositions of the invention typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fiber plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) or plants such as tobacco, nuts, coffee, eggplants, sugar cane, tea, pepper, vines including grape-bearing vines, hops, bananas, pineapple, turf and natural rubber plants, as well as ornamentals (flowers, shrubs, broad-leafed trees and evergreens, such as conifers). This list does not represent any limitation.

1. Bacterial Infections. The methods, active compounds and compositions can be used to treat bacterial infections in a variety of plants, with specific examples including but not limited to those set forth below.

Citrus. In citrus trees (including orange, lemon, lime, and grapefruit) active compounds and compositions as described herein can be used to treat or control a variety of microbial diseases, including but not limited to canker (caused by *Xanthomonas campestris* infection), bacterial spot (caused by *Xanthomonas campestris* pv. *Citrumelo* infection); Black Pit (fruit) (caused by *Pseudomonas syringae* infection); Blast (caused by *Pseudomonas syringae* infection) citrus variegated chlorosis (caused by *Xylella fastidiosa* infection), and Citrus Huanglongbing (HLB) caused by *Candidatus* Liberibacter asiaticus.

Pome Fruit. In pome fruits (including apple, pear, quince, Asian pear, and loquat), active compounds and compositions as described herein can be used to treat or control a variety of microbial infections, including but not limited to Fire Blight (caused by *Erwinia amylovora* infection), Crown Gall (caused by *Agrobacterium tumefaciens* infection); Blister spot (caused by *Pseudomonas syringae* infection) and Hairy root (caused by *Agrobacterium rhizogenes* infection).

Peppers. In pepper plants, active compounds and compositions as described herein can be used to treat or control a variety of microbial infections, including but not limited to: Bacterial Spot (caused by *Xanthomonas campestris* pv. *vesicatoria* infection); Bacterial wilt (caused by *Ralstonia solanacearum* infection), and Syringae seedling blight and leaf spot (caused by *Pseudomonas sryingae* infection).

Tomatoes. In tomato plants, active compounds and compositions as described herein can be used to treat or control a variety of microbial infections, including but not limited to: Bacterial canker (caused by *Clavibacter michiganesis*), Bacterial speck (caused by *Pseudomonas syringae*), Bacterial spot (caused by *Xanthomonas campestris vesicatoria*), Bacterial stem rot and fruit rot (caused by *Erwinia carotovora*), Bacterial wilt (caused by *Ralstonia solanacearum*), Pith necrosis (caused by *Pseudomonas corrugate*), and Syringae leaf spot (caused by *Pseudomonas syringae*).

Soybeans. In soybeans, active compounds and compositions as described herein can be used to treat or control a variety of microbial infections, including but not limited to: Bacterial blight (caused by *Pseudomonas amygdale*), Bacterial pustules (caused by *Xanthomonas axonopodis* pv. *Glycines*), and Bacterial wilt (caused by *Ralstonia solanacearum* or *Curtobacterium flaccumfaciens*).

Corn, Cotton, Wheat and Rice. In corn, cotton, wheat and rice, active compounds and compositions as described herein can be used to treat or control a variety of microbial infections, including but not limited to: bacterial blights, leaf spots and leaf streak caused by *Xanthomonas* species; bacterial sheath rot, stripe and spot caused by *Pseudomonas* species; and to bacterial stalk and top rot, wilt, foot rot, pink seed and lint degradation caused by *Erwinia* species.

Pineapple. In pineapple, active compounds and compositions as described herein can be used to treat or control a variety of microbial infections, including but not limited to: Bacterial heart rot and Fruit collapse (caused by *Erwinia chrysanthemi*), Bacterial fruitlet brown rot (caused by *Erwinia ananas*), Marbled fruit and Pink fruit (caused by *Erwinia herbicola*), Soft rot (caused by *Erwinia carotovora*), and Acetic souring (caused by Acetic acid bacteria).

The above listing is but a sampling, and active compounds and compositions as described herein may also be used to treat or control bacteria (some of which are named above) in a variety of plants. For example, the bacteria *Xylella fastidiosa* infects citrus trees as noted above (citrus variegated chlorosis), and also infects grapevines (Pierce's disease). Other plant hosts of *Xylella fastidiosa* include, but are not limited to, ornamentals, oleander (leaf scorch), almond, coffee, maple, mulberry, elm, sycamore, alfalfa, etc. Similarly, *Ralstonia solanacearum* infects soybeans (bacterial wilt) as well as banana (Moko disease), tobacco (Granville wilt), geranium (southern bacterial wilt), potato (brown rot) and a wide variety of other plants, including ginger and mulberry.

2. Fungal Infections. In addition to treating or controlling bacterial infections, active compounds and compositions as described herein can be used to treat or control fungal infections such as rots, leaf molds, blights, wilts, damping-off, spot, root rot, stem rot, mildew, brown spot, gummosis, melanose, post-bloom fruit drop, scab, alternaria, canker, flyspeck, fruit blotch, dieback, downy mildews, ear rots, anthracnose bunts, smut, rust, eyespot and pecky rice. Genera of plant-pathogenic fungi that can be treated or controlled by the active compounds, compositions, and methods described herein include but are not limited to: *Pythium* spp., *Fusarium* spp., *Rhizoctonia* spp., *Cercospora* spp., *Alternaria* spp., *Colletotrichum* spp., *Ustilago* spp., *Phoma* spp., *Gibberella* spp. *Penicillium* spp., *Glomerella* spp. *Diplodia* spp., *Curvularia* spp., *Sclerospora* spp., *Peronosclerospora* spp., *Cercospora* spp., *Puccinia* spp., *Ustilago* spp., *Aspergillus* spp., *Phomopsis* spp., *Diaporthe* spp., *Botiytis* spp., *Verticillium* spp., *Phytophthors* spp.

Particular fungal infections that can be treated or controlled by the methods, compounds and compositions described herein, in vegetables and greenhouse crops, include *Phytophthora* blight (caused by *Phytophthora capsici*) and *Pythium* damping-off (caused by *Pythium* spp).

Note that *Phytophthora* also has adverse effects on crops ranging from pineapples to cotton. It can kill woody citrus seedlings and young citrus trees (oranges, grapefruits, lemons, limes). In the greenhouse, germinating seed and seedlings are very susceptible to damping-off caused by *Phytophthora, Pythium, Sclerotina* and *Rhizoctonia* species. The cost to the grower to lose his crop to any of these fungi is substantial. The loss can happen at transplant time or when the crop is ready to be harvested.

The problems of fungi are not restricted to traditional crops but also extend to forestry products and have worldwide scope. *Phytophthora cinnamomi* is a soil-borne water mould that leads to a condition in plants called "root rot" or "dieback." *P. cinnamomi* causes root rot affecting woody ornamentals including azalea, dogwood, forsythia, Fraser fir, hemlock, Japanese holly, juniper, rhododendron, white pine, and American chestnut. *P. cinnamomi* is responsible for the destruction of the elegant American chestnut tree. In Australia, *P. cinnamomi* has spread through the forests of western Australia, and into coastal forests of Victoria, where entire plant ecosystems are being obliterated. Given that *P. cinnamomi* is a soil-borne water mould that infects the roots, almost the entire action takes place below ground. This problem highlights the importance of developing new compounds to counter fungal infections, even those that directly affect only the roots of the plant rather than the more visible effects on fruits or vegetables.

Active compounds of the invention can be applied to plants or plant loci in accordance with known techniques. The compound(s) can be tank mixed with other agricultural, turf, ornamental nursery, forestry and all other plant-labeled compatible pesticides. The compound(s) can be applied to seed. The compound(s) can be applied to edible and non-edible crops. The compound(s) can be applied to roots and all other parts of all plants. The compound(s) can be applied in greenhouses. The compound(s) can be applied and used in food-processing facilities. The compound(s) can be applied to plastic food bags and containers. The compound(s) can be applied as a solid, as its free base, or as a salt. The salts can include, but are not limited to, HI, HCl, HBr, $H_2SO_4$, acetic acid, and trifluoroacetic acid. The compound(s) can applied as a solution from 0.0001% to 99.9%. The compound(s) can be applied as a solid or solution with copper-based cidal compounds. The compound(s) can be applied with specific additional active agents, including but not limited to bactericides, fungicides, pesticides, biological insecticides and microbial insecticides.

Application can be carried out with any suitable equipment or technique, such as: Aerial—Fixed wing and Helicopter; Ground Broadcast Spray—Boom or boomless system, pull-type sprayer, floaters, pick-up sprayers, spray coupes, speed sprayers, and other broadcast equipment, water wagons and water bags; Low pressure boom sprayers, High pressure sprayers; Air blast sprayers; Low volume air sprayers (mist blowers); Ultra-low volume sprayers (ULV); Aerosol Generators (foggers); Dusters; Soil Injector; Hand-Held or High-Volume Spray Equipment—knapsack and backpack sprayers, pump-up pressure sprayers, hand guns, motorized spray equipment; Selective Equipment—Recirculating sprayers, shielded and hooded sprayers; Controlled droplet applicator (CDA) hand-held or boom-mounted applicators that produce a spray consisting of a narrow range of droplet size; Any and all greenhouse sprayers; Micro-sprinkler or drip irrigation systems; Chemigation.

One method of applying an active compound of the invention, or an agrochemical composition which contains at least one of said compounds, is foliar application. The frequency of application and the rate of application will depend on the risk of infestation by the corresponding pathogen. However, the active compounds can also penetrate the plant through the roots via the soil (systemic action) by drenching the locus of the plant with a liquid formulation, or by applying the compounds in solid form to the soil, e.g. in granular form (soil application). In crops of water such as rice, such granulates can be applied to the flooded rice field. The active compounds may also be applied to seeds (coating) by impregnating the seeds or tubers either with a liquid formulation of the fungicide or coating them with a solid formulation.

The term locus as used herein is intended to embrace the fields on which the treated crop plants are growing, or where the seeds of cultivated plants are sown, or the place where the seed will be placed into the soil. The term seed is intended to embrace plant propagating material such as cuttings, seedlings, seeds, and germinated or soaked seeds.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

F. Combination Treatments.

In some embodiments, methods of enhancing the effects of a microbicide (such as a microbicide comprising copper, e.g., Kocide® 2000 or Kocide® 3000 (DuPont™, with active ingredient copper hydroxide) are disclosed, comprising the step of applying an active compound in combination with a microbicide, the active compound being applied in an amount effective to enhance the effects of the microbicide.

In some embodiments, methods of enhancing the effects of a plant defense activator are disclosed, comprising the step of applying an active compound in combination with a plant defense activator, the active compound being applied in an amount effective to enhance the effects of the plant defense activator.

"Enhancing" the effects of a microbicide by applying an active compound in combination with the microbicide refers to increasing the effectiveness of the microbicide, such that the microorganism killing and/or growth inhibition is higher at a certain concentration of the microbicide applied in combination with the active compound than without. In some embodiments, a bacteria or other microorganism is "sensitized" to the effects of a microbicide, such that the bacteria or other microorganism that was resistant to the microbicide prior to applying the active compound (e.g., little to none, or less than 20, 10, 5 or 1% are killed upon application) is rendered vulnerable to that microbicide upon or after applying the active compound (e.g., greater than 20, 30, 40, 50, 60, 70, 80, 90, or 95% or more are killed).

Similarly, "enhancing" the effects of a plant defense activator by applying an active compound in combination with the plant defense activator refers to increasing the effectiveness of the plant defense activator, such that the microorganism killing and/or growth inhibition is higher at a certain concentration of the plant defense activator applied in combination with the active compound than without. In some embodiments, a bacteria or other microorganism is "sensitized" to the effects of a plant defense activator, such that the bacteria or other microorganism that was resistant to the effects of the plant defense activator prior to applying the active compound (e.g., little to none, or less than 20, 10, 5 or 1% are killed upon application) is rendered vulnerable to the effects of that plant defense activator upon or after applying the active compound (e.g., greater than 20, 30, 40, 50, 60, 70, 80, 90, or 95% or more are killed).

As used herein, the application of two or more compounds (inclusive of active compounds and microbicides) "in combination" means that the two compounds are applied closely enough in time that the application of or presence of one alters the biological effects of the other. The two compounds may be applied simultaneously (concurrently) or sequentially.

Simultaneous application of the compounds may be carried out by mixing the compounds prior to application, or by applying the compounds at the same point in time but at different sites of the plant or using different types of applications, or applied at times sufficiently close that the results observed are indistinguishable from those achieved when the compounds are applied at the same point in time.

Sequential application of the compounds may be carried out by applying, e.g., an active compound at some point in time prior to application of a microbicide, such that the prior application of active compound enhances the effects of the microbicide (e.g., percentage of microorganisms killed and/or slowing the growth of microorganisms). In some embodiments, an active compound is applied at some point in time prior to the initial application of a microbicide. Alternatively, the microbicide may be applied at some point in time prior to the application of an active compound, and optionally, applied again at some point in time after the application of an active compound.

EXAMPLES

Example 1

Compound numbering for Example 1 applies only to Example 1. Formula (II)(a)(i) ("compound 1") was synthesized in 10 linear steps, outlined in Scheme 1. Diethyl fumarate and 1,3-butadiene were subjected to a [4+2] cycloaddition to yield the Diels-Alder adduct 2. The diester 2 was then reduced with lithium aluminum hydride (LiAlH$_4$) to yield diol 3. The diol was then treated with mesityl chloride (MsCl) to generate the corresponding bis-mesylate 4 that was then refluxed with sodium azide (NaN$_3$) to yield di-azide 5. We then epoxidized 5 with meta-chloroperoxybenzoic acid (m-CPBA) at room temperature in the absence of ambient light to generate 6. Epoxide 6 was then treated with NaN$_3$ and sulfuric acid H$_2$SO$_4$ in refluxing ethanol to yield the azidoalcohol 7 that was subsequently subjected to hydrogenating conditions in the presence of Di-tert-butyl dicarbonate (Boc$_2$O). The tri-Boc protected amino alcohol 8 was then oxidized with pyridinium chlorochromate to generate ketone 9. Quantitative Boc-deprotection with TFA, followed by conversion to the HCl, and finally condensation of our α-aminoketone with cyanamide generated 1 in 7.5% overall yield from commercially available starting materials.

Scheme 1. Synthesis of compound 1.

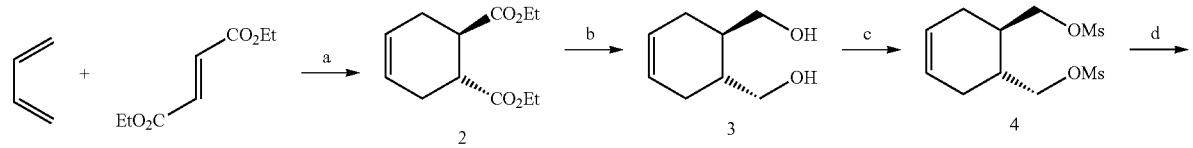

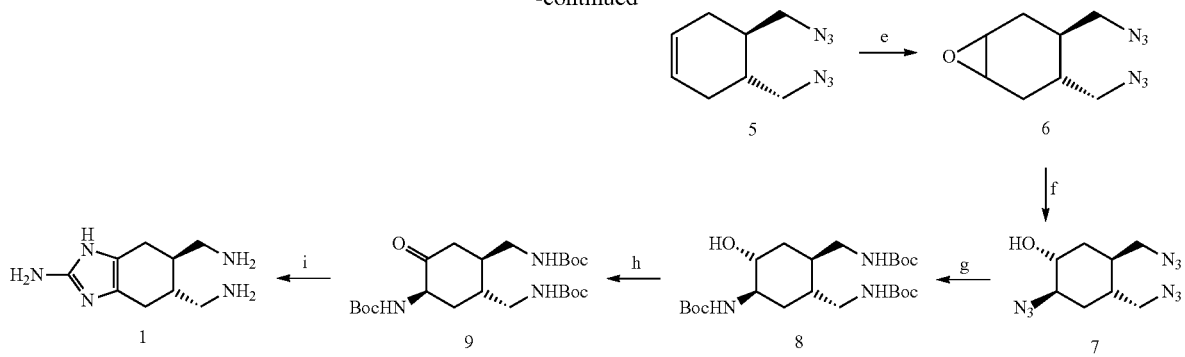

Reaction conditions: a. Toluene, reflux, 24 hours; b. lithium aluminum hydride, 0° C., diethyl ether; c. mesityl chloride, dichloromethane, diisopropylethyl amine; d. sodium azide, DMF, 100° C.; e. m-CPBA, dichloromethane, room temperature, 24 hours; f. sodium azide, H₂SO₄, ethanol, reflux; g. H₂, 10% Pd/C, DMF, Boc₂O; h. PCC, methylene chloride; i. TFA/methylene chloride, then HCl/MeOH, then Cyanamide/H₂O/pH = 4.5, 90° C., 3 hours.

Control compounds were also synthesized (Scheme 2). Starting with 2-aminoimidazole (2-AI) 1, we acylated the 2-amino position of the 2-aminoimidazole ring with an acyl pyrrole moiety to yield compound 10. This was designed to test the importance of the 2-AI ring as the critical pharmacophore that imparted biological activity on our molecule. We also synthesized the diastereomer of compound 1, where one of the chiral centers was inverted. This diastereomer, 11, was synthesized using the same synthetic sequence delineated above.

Scheme 2. Synthesis of control compounds 10 and 11.

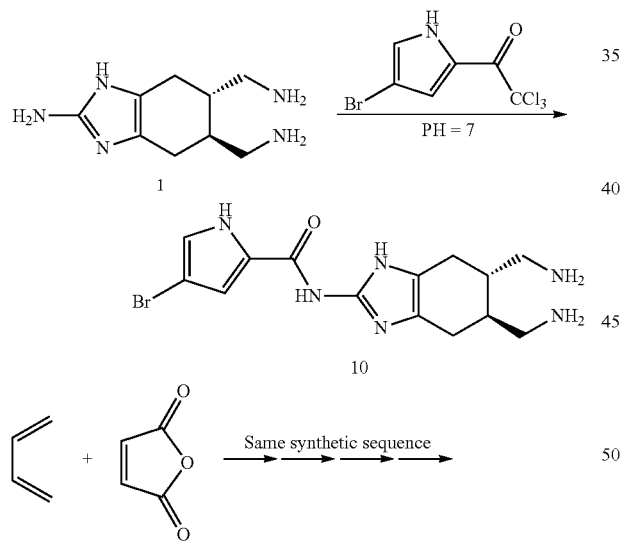

Example 2

Bicyclic 2-aminoimidazole derivatives. Compound numbering for Example 2 applies only to Example 2. Three trans-bromoageliferin analogue (TAGE) derivatives were synthesized that possessed an acylpyrrole ring in a manner that mimics the ageliferin natural products (Scheme 3).

Scheme 3. Synthesis of advanced ageliferin analogues.

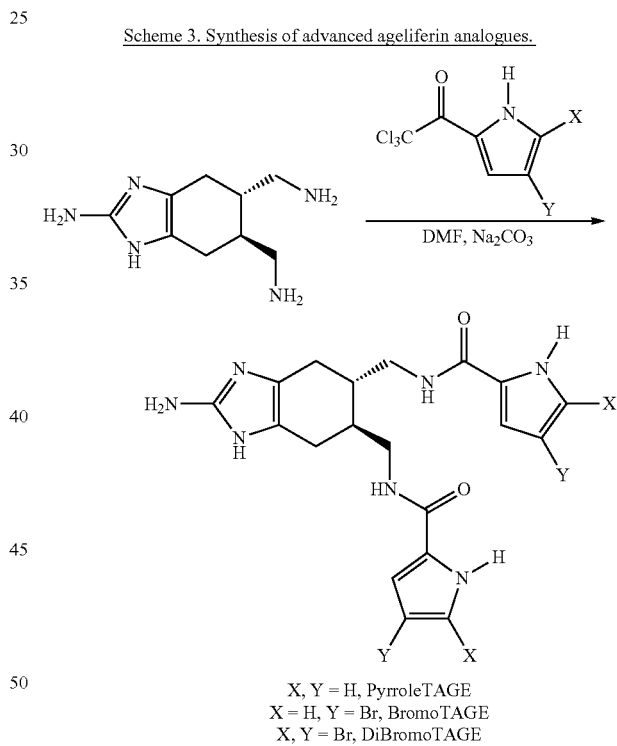

X, Y = H, PyrroleTAGE
X = H, Y = Br, BromoTAGE
X, Y = Br, DiBromoTAGE

Previous studies have indicated that the incorporation of an acyl pyrrole moiety within the 2-aminoimidazole scaffold dramatically increases anti-biofilm activity. To synthesize the three TAGE derivatives, TAGE was first synthesized on multi-gram scale using the synthetic approach we outlined previously. TAGE was then coupled to the appropriate the appropriate acyl pyrrole trichloromethyl ketone to generate the 3 TAGE derivatives (PyrroleTAGE, BromoTAGE, and DibromoTAGE).

Mammalian cytotoxicity of TAGE was investigated. Bromoageliferin, a natural sponge compound, is known to modulate the activity of calcium channels (U. Bickmeyer, *Toxicon*, 2005, 45, 627). GH4C1 rat pituitary cells and N2A mouse neuroblastoma cells were chosen for cytotoxicity screening. These cell lines are utilized for evaluating toxicity of marine natural products (Burkholder et al., *Proc. Natl. Acad. Sci. USA,* 2005, 102, 3471; Van Dolah et al., *Nat. Toxins,* 1994, 2, 189). Each cell line was plated at 3×10$^4$ cells/well in 96-well plates in 50 μl of Dulbeccos Modified Eagles Medium (DMEM). The cells were allowed to adhere at 37° C. in 5% $CO_2$ for 4 hours before use. 4 μl of test fractions were added and the cells incubated for 18 hours. Cell viability was assessed through an MTT-based colorimetric assay. All cells remained viable in the presence of up to 600 μM of our compounds, which indicates a lack of cytotoxicity.

All $^1$H NMR (300 MHz) and $^{13}$C NMR (75 MHz) spectra were recorded at 25.0° C. on a Varian Mercury spectrometer. Chemical shifts (δ) are given in ppm relative to tetramethylsilane or the respective NMR solvent. Abbreviations used are s=singlet, m=multiplet. High resolution ESI was used to determine molecular weight of new compounds in this study. Silica gel (40 μm average particle size) was used for column chromatography. All reagents were used without further purification from commercial sources unless otherwise noted.

General Procedure for Acylation of TAGE. DMF (2 or 3 ml) was added to a reaction vial containing TAGE.3HCl along with $Na_2CO_3$ (5 equivalents), and the respective brominated or non-brominated 2-(trichloroacetyl)-pyrrole variant (2.1 equivalents). The reaction was then allowed to stir under an argon atmosphere at 50° C. overnight. Upon completion of the reaction, the reaction vial was removed from the heat source and concentrated under reduced pressure vacuum. The resulting residue was purified by flash column chromatography (utilizing a gradient starting at 10% methanol/ammonia in DCM and increasing polarity to 40% methanol/ammonia in DCM) to give the corresponding acylpyrrole TAGE derivative. Percent yields are recorded with compound characterization below.

PyrroleTAGE—DMF (2 ml), 104.4 mg TAGE.3HCl, 155.6 mg 2-(trichloroacetyl)-pyrrole, 183 mg $Na_2CO_3$ yielded 69 mg PyrroleTAGE as a free base after purification (53% yield). $^1$H NMR (300 Hz, DMSO-d$_6$) δ11.47 (s, 2H), δ 8.20 (s, 2H), δ 7.40 (s, 2H), δ 6.84 (s, 2H), δ 6.77 (s, 2H), δ 6.07 (s, 2H), δ 3.21 (m, 4H), δ 2.62-2.50 (m, 2H partially buried in DMSO peak), δ 2.26-2.16 (m, 4H) ppm; $^{13}$C NMR (75 Hz, DMSO-d$_6$) δ 160.8, 146.5, 126.3, 121.1, 117.6, 110.2, 108.5, 40.7, 34.3, 20.1; HRMS (ESI) calcd for $C_{19}H_{24}N_7O_2$ (MH)$^+$ 382.1985, found 382.1982.

BromoTAGE—DMF (2 ml), 101 mg TAGE.3HCl, 210.7 mg 4-bromo-2-(trichloroacetyl)-pyrrole, 180 mg $Na_2CO_3$ yielded 89 mg BromoTAGE as a free base after purification (50% yield). $^1$H NMR (300 Hz, DMSO-d$_6$) δ11.91 (s, 2H), δ 8.44 (t, 2H), δ 7.42 (s, 2H), δ 6.95 (s, 2H), δ 6.91 (s, 2H), δ 3.15 (m, 4H), δ 2.60-2.50 (m, 2H partially buried in DMSO peak), δ 2.25-2.16 (m, 4H) ppm; $^{13}$C NMR (75 Hz, DMSO-d$_6$) δ 159.7, 146.5, 126.9, 121.0, 117.5, 111.9, 94.9, 40.8, 34.0, 20.1; HRMS (ESI) calcd for $C_{19}H_{22}N_7O_2Br_2$ (MH)$^+$ 538.0196, found 538.0185.

DibromoTAGE—DMF (3 ml), 106 mg TAGE.3HCl, 274 mg 4,5-dibromo-2-(trichloroacetyl)-pyrrole, 195 mg $Na_2CO_3$ yielded 127 mg DibromoTAGE as a free base after purification (52% yield). $^1$H NMR (300 Hz, DMSO-d$_6$) δ 8.51 (t, 2H), δ 7.41 (s, 2H), δ 6.98 (s, 2H), δ 3.19 (m, 4H), δ 2.60-2.50 (m, 2H partially buried in DMSO peak), δ 2.25-2.16 (m, 4H) ppm; $^{13}$C NMR (75 Hz, DMSO-d$_6$) δ 158.9, 146.5, 128.1, 117.5, 113.1, 104.3, 97.8, 40.8, 33.9, 20.1; HRMS (ESI) calcd for $C_{19}H_{20}N_7O_2Br_4$ (MH)$^+$ 693.8406, found 693.8410.

Example 3

Reverse Amide 2-aminoimidazole oroidin analogues. Compound numbering for Example 3 applies only to Example 3. The marine alkaloid oroidin along with a small library of reverse amide (RA) 2-aminoimidazoles were synthesized. One of the best methods for large scale preparation of the 2-AI scaffold en route to prepare oroidin and other family members involves Akabori reduction (Na/Hg) of ornithine methyl ester 7 followed by condensation with cyanamide under pH controlled conditions (S. Akabori, *Ber. Dtsch. Chem. Ges.,* 1933, 66, 151-158; G. C. Lancini and E. Lazzari, *J. Heterocycl. Chem.,* 1966, 3, 152; A. Olofson et al., *J. Org. Chem.,* 1998, 63, 1248-1253). Oroidin was synthesized as reported and matched characterization data. Derivatization can then be achieved via acylation of the alkyl amine off the carbon tail with variously substituted trichloroacetyl pyrroles. However, this chemistry is plagued by severe limitations, most notably the overall lack of compatibility of this system with other trichloroacetyl esters. In addition, solubility issues of the parent 2-AI leaves much to be desired. Many attempts by our group in developing other acylation conditions that would allow for the generation of greater diversity have proven unfruitful. From a practical standpoint, purifications of intermediates bearing an unprotected 2-AI often require large amounts of methanol saturated with ammonia (MeOH/NH$_3$), which is cumbersome to prepare and can be difficult to remove from the pure sample after column chromatography.

Figure 2:
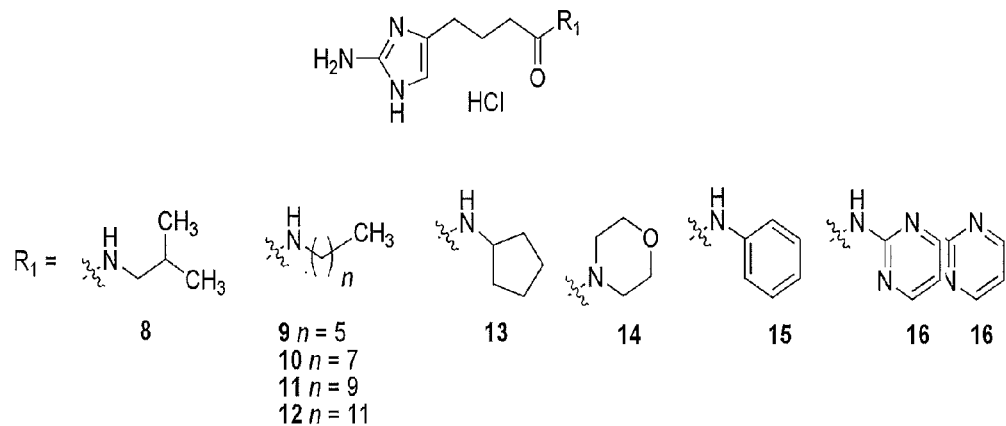
FIG. 2. Members of the reverse amide library.

Implementation of a reverse amide approach, coupled with a practical protecting group strategy, would effectively eliminate many of the aforementioned handicaps with current methods. Installation of the reverse amide bond could be obtained by direct aminolysis of an intermediate Boc-2AI alkyl ester or through couplings of a carboxylic acid (FIG. 1). These intermediates could be accessed through α-bromoketones which are obtained by diazomethane homologation with the proper acyl chloride. Additionally, significant diversity can be achieved by incorporating any commercially available amine with a common RA intermediate. Herein we report the synthesis of a focused reverse amide (RA) library (FIG. 2).

Synthesis of RA Library. Scaffold synthesis began with treatment of the commercially available acid chloride 17 with diazomethane (Scheme 4). Adiyaman et al., *Tet. Lett.,* 1996, 37, 4849-4852. Quenching with concentrated HCl or HBr delivered the corresponding α-haloketones in excellent yields which were isolable by column chromatography. Installation of the protected 2-aminoimidazole moiety was achieved through a Boc-guanidine condensation in DMF at ambient temperature to yield 18. Significantly higher yields for this step were obtained when two equivalents of sodium iodide were added to the reaction mixture and represents a significant improvement over previous reports. N. Ando and S. Terashima, *Synlett,* 2006, 2836-2840. V. B. Birman and X. T. Jiang, *Org. Lett.,* 2004, 6, 2369-2371. It was also observed during this sequence that the α-bromoketone afforded higher yields than its α-chloro counterpart in the cyclization reaction.

Scheme 4.

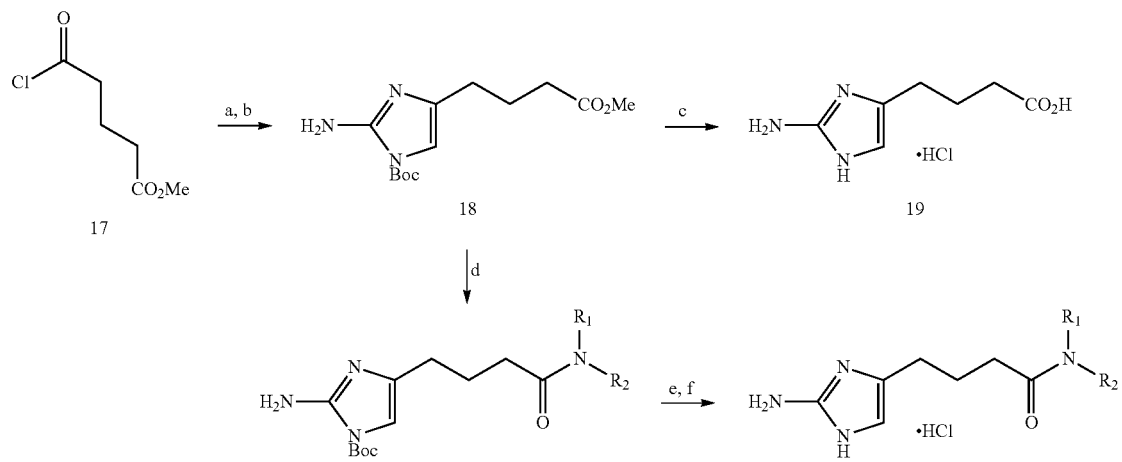

1st Generation Synthesis of the RA Scaffold; Reaction conditions: (a) i. CH$_2$N$_2$, Et$_2$O/CH$_2$Cl$_2$, 0° C. ii. conc. HCl (90%) or conc. HBr (93%) (b) Boc-guanidine, NaI, DMF, 65% (c) LiOH, MeOH/THF/H$_2$O (3:1:1) then 1N HCl to pH = 5, 94% (d) AlMe$_3$, NR$_1$R$_2$, DCE, 0° C. TO 60° C. (e) TFA, CH$_2$Cl$_2$ (f) 2M HCl in Et$_2$O The first approach to the RA scaffold relied heavily on the aminolysis of intermediate 18 since this would afford the Boc-protected RA precursors in a single synthetic step. After deprotection with TFA and HCl salt exchange, isolation of the targets would require only filtration with no need for further purification. Based upon the seminal paper published by Weinreb on the transformation, trimethylaluminum was used as the Lewis acid to affect the direct aminolysis reaction (Basha et al., *Tet. Lett.*, 1977, 4171-4174). Numerous reaction factors were taken into account such as choice of solvent, equivalents of aluminum-amine complex, reagent order of addition, time, and temperature. Despite all of the conditions scanned (data not shown), the highest yielding reaction occurred in only 55% yield when aniline was used as the amine partner. Triazabicyclo[4.4.0]dec-5-ene (TBD) was also examined as a potential catalyst to promote the direct aminolysis of ester 18 (Sabot et al., *Tet. Lett.*, 2007, 48, 3863-3866). Heating both starting materials in the presence of 30 mol % of TBD in toluene at elevated temperatures for extended periods of time failed to produce any desired product as evident by TLC analysis (data not shown).

Due to the problems encountered utilizing aminolysis, we opted for a more conventional route to access the RA scaffold through the intermediacy of an activated carboxylic acid. Unfortunately, saponification of the methyl ester 18 proved problematic on this system as cleavage of the Boc group was observed under the basic conditions of both LiOH/MeOH/THF/H$_2$O or LiI/pyridine. Decomposition of the methyl ester was also observed when TMSOK in methylene chloride or (Bu$_3$Sn)$_2$O in toluene at either ambient temperature or reflux were employed as the saponification agents (data not shown).

Persuaded by these results that the current route required revision, we began a second generation approach to our core scaffold (Scheme 5). This approach relied on a different protecting group strategy, substituting the methyl ester for a benzyl ester which, in the case of another failed attempt at aminolysis, would undergo hydrogenolysis under mild conditions to deliver the corresponding Boc-protected acid 22. Synthesis began with the known mono benzyl ester acid (Li et al., *J. Am. Chem. Soc.*, 1995, 117, 2123-2127) 20 which was transformed into the benzyl protected α-bromoketone by conversion to its acid chloride followed by diazomethane homologation and concomitant quench with concentrated HBr. Cyclization of this intermediate afforded the Boc-protected 2-AI 21 in 66% yield. All attempts at direct aminolysis of benzyl ester 21 resulted in sluggish reactions that were plagued by the formation of multiple side products.

Scheme 5.

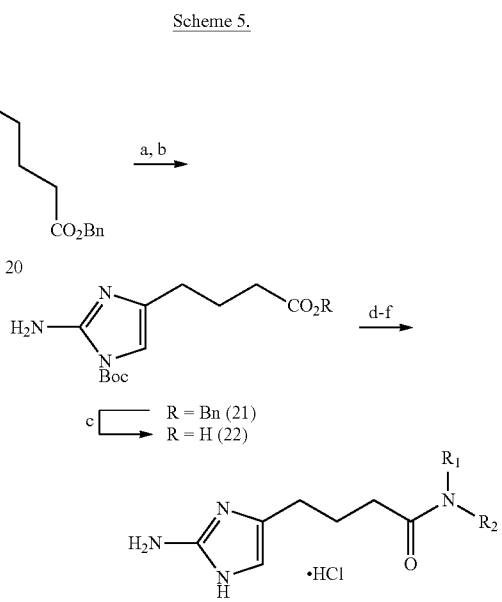

2nd Generation Synthesis of RA Scaffold; Reaction conditions: (a) i. (COCl)$_2$, DMF (cat.), CH$_2$Cl$_2$ ii. CH$_2$N$_2$, Et$_2$O/CH$_2$Cl$_2$, 0° C. iii. conc. HBr, 88% (b) Boc-guanidine, DMF, 66% (c) H$_2$ (1 atm), 10% Pd/C, THF, 98% (d) EDC, HOBt, NR$_1$R$_2$, DMF (e) TFA, CH$_2$Cl$_2$ (f) 2M HCl in Et$_2$O Given the failure of the direct aminolysis conversion, the two-step approach to the RA scaffold was investigated. Deprotection proceeded as planned and was accomplished by subjecting 21 to a hydrogen atmosphere at balloon pressure to cleanly afford pure Boc-protected acid 22 in near quantitative yield (98%). With the acid now in hand and available on a multi-gram scale, attempts to install the key amide bond were assessed. A number of activating agents were scanned including DCC, EDC, HCTU, CDI, and cyanuric chloride to affect the transformation. Of those listed only EDC and HCTU were able to give consistent and tangible results. EDC was chosen over HCTU due to ease of purification in separating side products during column chromatography. It was during this optimization that the limitation of the synthetic route was identified to be the reactivity of the Boc group. A significant quantity of a Boc-protected starting amine was isolated and characterized, signifying the lability of the Boc-group due to Boc-transfer under the reaction conditions regardless of which activating agent was used.

With two routes in hand to generate the RA scaffold, we assembled the focused library outlined in Table 1. EDC/HOBt couplings of acid 22 were used to generate most of the linear alkyl chain analogues (28-34%) while aminolysis of the methyl ester intermediate 18 furnished the remaining compounds (11-55%) in the library (Table 1). The final step of the synthetic approach required removal of the Boc group, which proceeded at room temperature in TFA/DCM. The resulting trifluoroacetate salts of each target were then traded out for their HCl counterparts.

TABLE 1

Completion of the reverse amide library

Amine $\xrightarrow{a\ or\ b}$

| Amine | Conditions | Coupled Product | Target |
|---|---|---|---|
| isobutylamine | a | 23 | 8 |
| hexylamine | b | 24 | 9 |
| octylamine | b | 25 | 10 |
| decylamine | a | 26 | 11 |
| dododecylamine | b | 27 | 12 |
| cyclopentylamine | a | 28 | 13 |
| morpholine | a | 29 | 14 |
| aniline | a | 30 | 15 |
| 2-aminopyrimidine | a | 31 | 16 |

Reaction conditions: (a) AlMe$_3$, 18, DCE, 0° C. to 60° C.
(b) 22, EDC, HOBt, DMF
(c) TFA, CH$_2$Cl$_2$
(d) 2M HCl in Et$_2$O All reagents including anhydrous solvents used for the chemical synthesis of the library were purchased from commercially available sources and used without further purification unless otherwise noted. All reactions were run under either a nitrogen or argon atmosphere. Flash silica gel chromatography was performed with 60 Å mesh standard grade silica gel from Sorbtech. $^1$H and $^{13}$C NMR spectra were obtained using Varian 300 MHz or 400 MHz spectrometers. NMR solvents were purchased from Cambridge Isotope Labs and used as received. Chemical shifts are given in parts per million relative to DMSO-d$_6$ (δ 2.50) and CDCl$_3$ (δ 7.27) for proton spectra and relative to DMSO-d$_6$ (δ 39.51) and CDCl$_3$ (δ 77.21) for carbon spectra with an internal TMS standard. High-resolution mass spectra were obtained at the North Carolina State Mass Spectrometry Laboratory for Biotechnology. ESI experiments were carried out on Agilent LC-TOF mass spectrometer.

6-bromo-5-oxo-hexanoic acid methyl ester. Methyl glutaryl chloride (2.5 mL, 18.23 mmol) was dissolved into anhydrous dichloromethane (10 mL) and added drop-wise to a 0° C. solution of CH$_2$N$_2$ (55.0 mmol generated from Diazald® diazomethane precursor/KOH) in diethyl ether (150 mL). This solution was stirred at 0° C. for 1.5 h at which time the reaction was quenched via the drop-wise addition of 48% HBr (7.5 mL). The reaction mixture was diluted with dichloromethane (25 mL) and immediately washed with sat. NaHCO$_3$ (3×25 mL) and brine (2×25 mL) before being dried (MgSO$_4$), filtered and concentrated. The crude oil was purified via flash column chromatography (10-30% EtOAc/Hexanes) to obtain the title compound (3.76 g, 93%) as a colorless oil. $^1$H NMR (400 MHz, CDCl$_3$) δ 3.91 (s, 2H), 3.68 (s, 3H), 2.76 (t, 2H, J=7.2 Hz), 2.38 (t, 2H, J=7.2 Hz), 1.95 (quint, 2H, J=7.2 Hz); $^{13}$C NMR (75 MHz, CDCl$_3$) δ 201.36, 173.41, 51.67, 38.74, 34.16, 32.87, 19.13; HRMS (ESI) calcd for C$_7$H$_{12}$O$_3$Br (MH)$^+$ 222.9964, found 222.9964.

6-chloro-5-oxo-hexanoic acid methyl ester. Using the same general procedure as used above but instead quenching with conc. HCl afforded the chloro derivative (2.93 g, 90%) as a colorless oil. $^1$H NMR (400 MHz, CDCl$_3$) δ 4.13 (s, 2H), 3.67 (s, 3H), 2.69 (t, 2H, J=7.2 Hz), 2.38 (t, 2H, J=7.2 Hz), 1.94 (quint., 2H, J=7.2 Hz); $^{13}$C NMR (100 MHz, CDCl$_3$) δ 201.85, 173.33, 51.57, 48.22, 38.47, 32.66, 18.61; HRMS (ESI) calcd for C$_7$H$_{12}$O$_3$Cl (MH)$^+$ 179.0469, found 179.0476.

6-bromo-5-oxo-hexanoic acid benzyl ester. Monobenzylesterbutanoic acid 20 (3.00 g, 13.6 mmol) was dissolved in anhydrous dichloromethane (70 mL) at 0° C. and a catalytic amount of DMF was added. To this solution was added oxalyl chloride (3.60 mL, 41.3 mmol) drop-wise and the solution was then warmed to room temperature. After 1 h, the solvent and excess oxalyl chloride were removed under reduced pressure. The resulting solid was dissolved into anhydrous dichloromethane (10 mL) and added drop-wise to a 0° C. solution of CH$_2$N$_2$ (42.0 mmol generated from Diazald® diazomethane precursor (Sigma-Aldrich, St. Louis, Mo.)/KOH) in diethyl ether (120 mL). This solution was stirred at 0° C. for 1.5 h at which time the reaction was quenched via the drop-wise addition of 48% HBr (4.7 mL) The reaction mixture was diluted with dichloromethane (25 mL) and immediately washed with sat. NaHCO$_3$ (3×25 mL) and brine (2×25 mL) before being dried (MgSO$_4$), filtered and concentrated. The crude oil was purified by flash column chromatography (0-30% EtOAc/Hexanes) to obtain the title compound (3.57 g, 88%) as a colorless oil. $^1$H NMR (400 MHz, CDCl$_3$) δ 7.35 (m, 5H), 5.12 (s, 2H), 3.85 (s, 2H), 2.73 (t, 2H, J=6.8 Hz), 2.42 (t, 2H, J=6.8 Hz), 1.96 (quint, 2H, J=6.8 Hz); $^{13}$C NMR (75 MHz, CDCl$_3$) δ 201.43, 172.88, 136.15, 128.79, 128.48, 128.45, 66.52, 38.74, 34.07, 33.20, 19.23; HRMS (ESI) calcd for C$_{13}$H$_{16}$O$_3$Br (MH)$^+$ 299.0277, found 299.0279.

2-amino-4-(3-methoxycarbonyl-propyl)-imidazole-1-carboxylic acid tert-butyl ester (18). 6-bromo-5-oxo-hexanoic acid methyl ester (2.30 g, 10.3 mmol), Boc-guanidine (4.92 g, 30.9 mmol),[32] and NaI (3.07 g, 20.6 mmol) were dissolved in DMF (30 mL) and allowed to stir at room temperature. After 24 h the DMF was removed under reduced pressure and the residue was taken up in ethyl acetate (100 mL) and washed with water (3×50 mL) and brine (50 mL) before being dried (Na$_2$SO$_4$), filtered and evaporated to dryness. The resulting oil was purified by flash column chromatography (50-100%

EtOAc/Hexanes) to obtain a yellow oil. Trituration of the viscous oil with cold hexanes (20 mL) produced a precipitate, which upon filtration yielded 18 (1.89 g, 65%) as a pale yellow solid. $^1$H NMR (400 MHz, CDCl$_3$) δ 6.53 (s, 1H), 5.6 (br s, 2H), 2.41 (t, 2H, J=7.2 Hz), 2.37 (t, 2H, J=7.2 Hz), 1.93 (quint., 2H, J=7.2 Hz), 1.58 (s, 9H); $^{13}$C NMR (75 MHz, CDCl$_3$) δ 174.09, 150.11, 149.61, 138.39, 107.15, 84.81, 51.56, 33.65, 28.18, 27.68, 23.82; HRMS (ESI) calcd for C$_{13}$H$_{22}$N$_3$O$_4$ (MH)$^+$ 284.1604, found 284.1606.

4-(2-amino-1H-imidazol-4-yl) butyric acid hydrochloride (19). To 2-amino-4-(3-methoxycarbonyl-propyl)-imidazole-1-carboxylic acid tert-butyl ester 18 (50 mg, 0.176 mmol) was added methanol (0.60 mL), tetrahydrofuran (0.20 mL), and water (0.20 mL). Lithium hydroxide (9 mg, 0.352 mmol) was then added and the reaction was stirred at room temperature for 30 min. The pH of the solution was carefully adjusted to pH=5 with a 1N aqueous solution of HCl before being evaporated to dryness. The crude product was purified via a silica gel plug (100% MeOH sat. NH$_3$) to deliver the product as its corresponding free base. The hydrochloride salt was obtained through addition of a single drop of concentrated HCl to a methanolic solution (2 mL) of the free base. Rotary evaporation of this solution afforded 19 (34 mg, 94%) as a white solid. $^1$H NMR (300 MHz, DMSO-d$_6$) δ 12.25 (s, 1H), 12.13 (br s, 1H), 11.77 (s, 1H), 7.33 (s, 1H), 6.54 (s, 1H), 2.43 (t, 2H, J=7.2 Hz), 2.21 (t, 2H, J=7.2 Hz), 1.73 (m, 2H); $^{13}$C NMR (100 MHz, DMSO-d$_6$) δ 174.04, 146.92, 126.01, 108.62, 32.81, 23.47, 23.05; HRMS (ESI) calcd for C$_7$H$_{12}$N$_3$O$_2$ (MH)$^+$ 170.0924, found 170.0927.

2-amino-4-(3-benzyloxycarbonyl-propyl)-imidazole-1-carboxylic acid tert-butyl ester (21). 6-bromo-5-oxo-hexanoic acid benzyl ester (3.42 g, 11.99 mmol) and Boc-guanidine (5.73 g, 35.97 mmol) were dissolved in DMF (35 mL) and allowed to stir at room temperature. After 48 h the DMF was removed under reduced pressure and the residue was taken up in ethyl acetate (100 mL) and washed with water (3×50 mL) and brine (50 mL) before being dried (Na$_2$SO$_4$), filtered and evaporated to dryness. The resulting oil was purified by flash column chromatography (30-100% EtOAc/Hexanes) to obtain the title compound (2.79 g, 66%) as a colorless oil which solidified upon prolonged standing. $^1$H NMR (400 MHz, CDCl$_3$) δ 7.35 (m, 5H), 6.51 (s, 1H), 5.91 (s, 2H), 5.12 (s, 2H), 2.41 (m, 4H), 1.94 (quint., 2H, J=7.2 Hz), 1.57 (s, 9H); $^{13}$C NMR (75 MHz, CDCl$_3$) δ 173.45, 150.31, 149.59, 138.27, 136.36, 128.67, 128.29, 128.27, 107.05, 84.73, 66.23, 33.82, 28.16, 27.62, 23.79; HRMS (ESI) calcd for C$_{19}$H$_{26}$N$_3$O$_4$ (MH)$^+$ 360.1917, found 360.1919.

2-amino-4-(3-carboxy-propyl)-imidazole-1-carboxylic acid tert-butyl ester (22). To a solution of anhydrous THF (2 mL) and 10% Pd/C (12 mg) was charged 2-amino-4-(3-benzyloxycarbonyl-propyl)-imidazole-1-carboxylic acid tert-butyl ester 21 (101 mg, 0.281 mmol). Air was removed from the system and the reaction was back flushed with hydrogen. This process was repeated three times before setting the reaction under a hydrogen balloon at atmospheric pressure and temperature for 1 h. After that time the reaction was filtered through a Celite® diatomite pad (World Minerals Inc., Santa Barbara, Calif.) and the filter cake was washed with THF (8 mL) The filtrate was concentrated under reduced pressure to afford the title compound 21 (75 mg, 98%) as a white solid. $^1$H NMR (400 MHz, DMSO-d$_6$) δ 6.52 (s, 1H), 6.42 (br s, 2H), 2.52 (t, 2H, J=5.4 Hz), 2.18 (t, 2H, J=5.4 Hz), 1.71 (m, 2H), 1.53 (s, 9H); $^{13}$C NMR (100 MHz, DMSO-d$_6$) δ 175.00, 149.99, 148.95, 138.28, 105.86, 84.09, 39.24, 38.85, 33.70, 27.52, 27.08, 23.52; HRMS (ESI) calcd for C$_{12}$H$_{20}$N$_3$O$_4$ (MH)$^+$ 270.1448, found 270.1452.

General Aminolysis Procedure:

To a stirring 0° C. solution of amine (0.704 mmol) in anhydrous 1,2-dichloroethane (1 mL) was added drop-wise a 2M solution of AlMe$_3$ in PhCH$_3$ (0.351 mL, 0.704 mmol). The solution was stirred for 10 min before the addition of 2-amino-4-(3-methoxycarbonyl-propyl)-imidazole-1-carboxylic acid tert-butyl ester 18 (100 mg, 0.352 mmol) in several portions. Once dissolution was complete, the reaction was warmed to 60° C. and stirred until completion as evident by TLC analysis. The reaction was then cooled back down to 0° C. before being diluted with dichloromethane (5 mL) and quenched with water (1 mL). The resulting viscous solution was warmed to ambient temperature and Celite® diatomite was added. After stirring for 5 min, the mixture was filtered and the filtrate washed with brine (2×3 mL), dried (Na$_2$SO$_4$), and evaporated to dryness. The crude product was purified via flash column chromatography (2-10% MeOH/CH$_2$Cl$_2$) to afford pure product.

2-amino-4-(3-isobutylcarbamoyl-propyl)-imidazole-1-carboxylic acid tert-butyl ester (23) White solid (46 mg, 40%). $^1$H NMR (400 MHz, DMSO-d$_6$) δ 7.75 (m, 1H), 6.51 (s, 1H), 6.37 (br s, 2H), 2.85 (t, 2H, J=6.4 Hz), 2.22 (t, 2H, J=6.8 Hz), 2.07 (t, 2H, J=7.2 Hz), 1.61-1.73 (m, 3H), 1.53 (s, 9H), 0.81 (d, 6H, J=6.4 Hz); $^{13}$C NMR (100 MHz, DMSO-d$_6$) δ 171.82, 149.92, 148.95, 138.39, 105.84, 84.04, 45.94, 34.88, 28.09, 27.52, 27.23, 24.10, 20.14; HRMS (ESI) calcd for C$_{16}$H$_{29}$N$_4$O$_3$ (MH)$^+$ 325.2234. found 325.2238.

2-amino-4-(3-decylcarbamoyl-propyl)-imidazole-1-carboxylic acid tert-butyl ester (26). Tan solid (24 mg, 16%). $^1$H NMR (400 MHz, DMSO-d$_6$) δ 7.74 (m, 1H), 6.52 (s, 1H), 6.49 (br s, 2H), 3.00 (q, 2H, J=6.8 Hz), 2.22 (t, 2H, J=6.8 Hz), 2.04 (t, 2H, J=6.8 Hz), 1.71 (quint., 2H, J=6.8 Hz), 1.53 (s, 9H), 1.36 (m, 2H), 1.23 (s, 14H), 0.85 (t, 3H, J=6.8 Hz); $^{13}$C NMR (100 MHz, DMSO-d$_6$) δ 171.64, 149.82, 148.86, 137.90, 105.90, 84.16, 38.33, 34.88, 31.31, 29.16, 29.03, 28.97, 28.75, 28.73, 28.02, 27.51, 27.05, 26.40, 24.04, 22.12, 13.97; HRMS (ESI) calcd for C$_{22}$H$_{41}$N$_4$O$_3$ (MH)$^+$ 409.3173, found 409.3175.

2-amino-4-(3-cyclopentylcarbamoyl-propyl)-imidazole-1-carboxylic acid tert-butyl ester (28). White solid (54 mg, 45%). $^1$H NMR (400 MHz, DMSO-d$_6$) δ 7.72 (d, 1H, J=6.4 Hz), 6.5 (s, 1H), 6.38 (s, 2H), 3.97 (m, 1H), 2.21 (t, 2H, J=7.2 Hz), 2.02 (t, 2H, J=7.2 Hz), 1.73 (m, 4H), 1.61 (m, 2H), 1.53 (s, 9H), 1.47 (m, 2H), 1.32 (m, 2H); $^{13}$C NMR (75 MHz, DMSO-d$_6$) δ 171.27, 149.92, 148.86, 138.37, 105.88, 84.02, 50.04, 34.79, 32.32, 28.05, 27.53, 27.17, 24.00, 23.43; HRMS (ESI) calcd for C$_{17}$H$_{29}$N$_4$O$_3$ (MH)$^+$ 337.2234, found 337.2235.

2-amino-4-(4-morpholin-4-yl-4-oxo-butyl)-imidazole-1-carboxylic acid tert-butyl ester (29). Tan solid (33 mg, 27%). $^1$H NMR (400 MHz, DMSO-d$_6$) δ 6.52 (s, 1H), 6.39 (s, 2H), 3.52 (m, 4H), 3.41 (m, 4H), 2.28 (m, 4H), 1.42 (quint., 2H, J=7.2 Hz) 1.53 (s, 9H); $^{13}$C NMR (75 MHz, DMSO-d$_6$) δ 171.43, 150.56, 149.64, 139.17, 106.58, 84.78, 66.85, 46.14, 32.23, 28.23, 27.89, 24.19; HRMS (ESI) calcd for C$_{16}$H$_{27}$N$_4$O$_4$ (MH)$^+$ 339.2026, found 339.2027.

2-amino-4-(3-phenylcarbamoyl-propyl)-imidazole-1-carboxylic acid tert-butyl ester (30). White solid (66 mg, 55%). $^1$H NMR (300 MHz, DMSO-d$_6$) δ 9.88 (s, 1H), 7.59 (d, 2H, J=8.1 Hz), 7.27 (t, 2H, J=7.5 Hz), 7.00 (t, 1H, J=7.2 Hz), 6.55 (s, 1H), 6.44 (br s, 2H), 2.97 (m, 4H), 1.82 (m, 2H), 1.53 (s, 9H); $^{13}$C NMR (75 MHz, DMSO-d$_6$) δ 170.95, 149.71, 148.86, 139.25, 138.16, 128.47, 122.78, 118.98, 105.92, 84.00, 38.42, 35.71, 27.44, 27.01, 23.72; HRMS (ESI) calcd for C$_{18}$H$_{25}$N$_4$O$_3$ (MH)$^+$ 345.1921, found 345.1920.

2-amino-4-[3-(pyrimidin-2-ylcarbamoyl)-propyl]-imidazole-1-carboxylic acid tert-butyl ester (31). Tan solid (19 mg, 11%). $^1$H NMR (400 MHz, DMSO-d$_6$) δ 10.51 (s, 1H), 8.63 (d, 2H, J=4.8 Hz), 7.15 (t, 1H, J=4.8 Hz), 6.54 (s, 1H), 6.40 (s, 2H), 2.49 (t, 2H, J=7.2 Hz), 2.29 (t, 2H, J=7.2 Hz), 1.80 (quint., 2H, J=7.2 Hz), 1.53 (s, 9H); $^{13}$C NMR (75 MHz, DMSO-d$_6$) δ 171.34, 158.11, 157.63, 149.76, 148.85, 138.31, 116.37, 105.81, 83.98, 35.75, 27.44, 27.05, 23.37; HRMS (ESI) calcd for C$_{16}$H$_{23}$N$_6$O$_3$ (MH)$^+$ 347.1826, found 347.1827.

General EDC/HOBt Procedure: 2-amino-4-(3-carboxypropyl)-imidazole-1-carboxylic acid tert-butyl ester 22 (100 mg, 0.371 mmol), 1-hydroxybenzotriazole (100 mg, 0.742 mmol) and N-(3-dimethylaminopropyl)-N'-ethylcarbodiimide hydrochloride (142 mg, 0.742 mmol) were dissolved in anhydrous DMF (3 mL). The appropriate amine coupling partner (1.48 mmol) was then added and the solution was stirred at ambient temperature until completion was evident by TLC analysis. The reaction was concentrated under reduced pressure and the residue partitioned between ethyl acetate (20 mL) and water (10 mL) The organic layer was successively washed with water (3×10 mL), a 10% aqueous solution of citric acid (2×10 mL), sat. NaHCO$_3$ (2×10 mL), and brine (10 mL) before being dried (Na$_2$SO$_4$) and evaporated to dryness. The crude product was purified via flash column chromatography (2-10% MeOH/CH$_2$Cl$_2$) to afford the target compound.

2-amino-4-(3-hexylcarbamoyl-propyl)-imidazole-1-carboxylic acid tert-butyl ester (24). Pale yellow solid (41 mg, 32%). $^1$H NMR (300 MHz, DMSO-d$_6$) δ 7.73 (m, 1H), 6.50 (s, 1H), 6.39 (s, 2H), 2.99 (q, 2H, J=6.3 Hz), 2.21 (t, 2H, J=7.5 Hz), 2.04 (t, 2H, J=7.2 Hz), 1.70 (m, 2H), 1.53 (s, 9H), 1.31 (m, 3H), 1.23 (br s, 7H), 0.85 (t, 3H, J=5.1 Hz); $^{13}$C NMR (75 MHz, DMSO-d$_6$) δ 171.68, 149.93, 148.95, 138.37, 105.81, 84.04, 38.35, 34.91, 31.01, 29.14, 27.52, 27.22, 26.10, 24.06, 22.09, 13.93; HRMS (ESI) calcd for C$_{18}$H$_{33}$N$_4$O$_3$ (MH)$^+$ 353.2547, found 353.2549.

2-amino-4-(3-octylcarbamoyl-propyl)-imidazole-1-carboxylic acid tert-butyl ester (25). White solid (48 mg, 34%). $^1$H NMR (300 MHz, DMSO-d$_6$) δ 7.73 (m, 1H), 6.50 (s, 1H), 6.38 (s, 2H), 2.99 (q, 2H, J=5.4 Hz), 2.21 (t, 2H, J=7.5 Hz), 2.04 (t, 2H, J=7.2 Hz), 1.73 (m, 2H), 1.53 (s, 9H), 1.36 (m, 4H), 1.23 (br s, 10H), 0.85 (t, 3H, J=5.1 Hz); $^{13}$C NMR (75 MHz, DMSO-d$_6$) δ 171.72, 149.95, 148.95, 138.43, 105.83, 84.06, 38.35, 34.92, 31.26, 29.16, 28.71, 27.53, 27.22, 26.43, 24.10, 22.12, 13.98; HRMS (ESI) calcd for C$_{20}$H$_{37}$N$_4$O$_3$ (MH)$^+$ 381.2860, found 381.2861.

2-amino-4-(3-dodecylcarbamoyl-propyl)-imidazole-1-carboxylic acid tert-butyl ester (27). White solid (44 mg, 28%). $^1$H NMR (400 MHz, DMSO-d$_6$) δ 7.73 (t, 1H, J=5.6 Hz), 6.50 (s, 1H), 6.38 (s, 2H), 3.00 (q, 2H, J=5.6 Hz), 2.21 (t, 2H, J=7.6 Hz), 2.04 (t, 2H, J=7.6 Hz), 1.71 (quint., 2H, J=7.6 Hz), 1.53 (s, 9H), 1.36 (m, 2H), 1.23 (s, 18H), 0.85 (t, 3H, J=6.0 Hz); $^{13}$C NMR (75 MHz, DMSO-d$_6$) δ 171.58, 149.77, 148.88, 138.42, 105.76, 83.98, 38.28, 34.90, 31.18, 29.06, 28.88, 28.58, 27.47, 27.18, 26.29, 24.04, 21.96, 13.81, 13.27; HRMS (ESI) calcd for C$_{24}$H$_{45}$N$_4$O$_3$ (MH)$^+$ 437.3486. found 437.3487.

4-(2-amino-1H-imidazol-4-yl)-N-isobutyl-butyramide hydrochloride (8). A solution of 2-amino-4-(3-isobutylcarbamoyl-propyl)-imidazole-1-carboxylic acid tert-butyl ester 23 (76 mg, 0.234 mmol) in anhydrous dichloromethane (1 mL) was cooled to 0° C. TFA (1 mL) was charged into the flask and the reaction stirred for 5 h. After that time the reaction was evaporated to dryness and toluene (2 mL) was added. Again the mixture was concentrated and the process repeated. The resulting TFA salt was dissolved in dichloromethane (1 mL) and 2M HCl in diethyl ether (0.50 mL) was added followed by cold diethyl ether (8 mL) The precipitate was collected by filtration and washed with diethyl ether (3 mL) to yield the target compound 8 (59 mg, 97%) as a tan solid. $^1$H NMR (300 MHz, DMSO-d$_6$) δ 12.14 (s, 1H), 11.70 (s, 1H), 7.89 (m, 1H), 7.34 (br s, 2H), 6.55 (s, 1H), 2.84 (t, 2H, J=6.6 Hz), 2.38 (t, 2H, J=7.5 Hz), 2.10 (t, 2H, J=7.5 Hz), 1.60-1.79 (m, 3H), 0.82 (d, 6H, J=6.3 Hz); $^{13}$C NMR (75 MHz, DMSO-d$_6$) δ 171.52, 146.78, 126.31, 108.68, 46.00, 34.41, 28.09, 23.94, 23.64, 20.18; HRMS (ESI) calcd for C$_{11}$H$_{21}$N$_4$O (MH)$^+$ 225.1709, found 225.1711.

4-(2-amino-1H-imidazol-4-yl)-N-hexyl-butyramide hydrochloride (9). Using the same general procedure as used for the synthesis of 8,2-amino-4-(3-hexylcarbamoyl-propyl)-imidazole-1-carboxylic acid tert-butyl ester 24 (90 mg, 0.255 mmol) gave 9 (70 mg, 96%) as a pale yellow foam. $^1$H NMR (300 MHz, DMSO-d$_6$) δ 11.96 (s, 1H), 11.54 (s, 1H), 7.81 (m, 1H), 7.29 (br s, 2H), 6.56 (s, 1H), 3.01 (m, 2H), 2.40 (t, 2H, J=7.8 Hz), 2.07 (t, 2H, J=7.2 Hz), 1.73 (m, 2H), 1.23-1.36 (m, 8H) 0.85 (m, 3H); $^{13}$C NMR (100 MHz, DMSO-d$_6$) δ 171.35, 146.72, 126.37, 108.71, 38.43, 34.41, 31.00, 29.12, 26.12, 23.87, 23.62, 22.09, 13.96; HRMS (ESI) calcd for C$_{13}$H$_{25}$N$_4$O (MH)$^+$ 253.2022, found 253.2025.

4-(2-amino-1H-imidazol-4-yl)-N-octyl-butyramide hydrochloride (10). Using the same general procedure as used for the synthesis of 8,2-amino-4-(3-octylcarbamoyl-propyl)-imidazole-1-carboxylic acid tert-butyl ester 25 (50 mg, 0.131 mmol) gave 10 (39 mg, 93%) as a white solid. $^1$H NMR (300 MHz, DMSO-d$_6$) δ 12.13 (s, 1H), 11.69 (s, 1H), 7.87 (m, 1H), 7.33 (br s, 2H), 6.55 (s, 1H), 2.99 (q, 2H, J=6.3 Hz), 2.38 (t, 2H, J=7.5 Hz), 2.07 (t, 2H, J=7.5 Hz), 1.73 (m, 2H), 1.35 (m, 2H), 1.23 (m, 10H), 0.85 (t, 3H, J=6.3 Hz); $^{13}$C NMR (75 MHz, DMSO-d$_6$) δ 171.30, 146.80, 126.32, 108.57, 38.40, 34.39, 31.15, 29.06, 28.62, 28.56, 26.37, 23.86, 23.57, 21.99, 13.85; HRMS (ESI) calcd for C$_{15}$H$_{29}$N$_4$O (MH)$^+$ 281.2335, found 281.2339.

4-(2-amino-1H-imidazol-4-yl)-N-decyl-butyramide hydrochloride (11). Using the same general procedure as used for the synthesis of 8,2-amino-4-(3-decylcarbamoyl-propyl)-imidazole-1-carboxylic acid tert-butyl ester 26 (32 mg, 0.078 mmol) gave 11 (27 mg, 99%) as a white solid. $^1$H NMR (400 MHz, DMSO-d$_6$) δ 12.07 (s, 1H), 11.64 (s, 1H), 7.85 (s, 1H), 7.32 (br s, 2H), 6.56 (s, 1H), 3.00 (q, 2H, J=6.4 Hz), 2.38 (t, 2H, J=7.2 Hz), 2.07 (t, 2H, J=7.2 Hz), 1.73 (quint., 2H, J=7.2 Hz), 1.36 (m, 2H), 1.23 (s, 14H), 0.85 (t, 3H, J=7.2 Hz); $^{13}$C NMR (100 MHz, DMSO-d$_6$) δ 171.33, 146.72, 126.36, 108.70, 38.42, 34.41, 31.32, 29.15, 29.04, 28.99, 28.77, 28.73, 26.45, 23.89, 23.62, 22.12, 13.99; HRMS (ESI) calcd for C$_{17}$H$_{33}$N$_4$O (MH)$^+$ 309.2648, found 309.2647.

4-(2-amino-1H-imidazol-4-yl)-N-dodecyl-butyramide hydrochloride (12). Using the same general procedure as used for the synthesis of 8,2-amino-4-(3-dodecylcarbamoyl-propyl)-imidazole-1-carboxylic acid tert-butyl ester 27 (20 mg, 0.046 mmol) gave 12 (16 mg, 94%) as a white solid. $^1$H NMR (400 MHz, DMSO-d$_6$) δ 12.03 (s, 1H), 11.60 (s, 1H), 7.83 (t, 1H, J=6.4 Hz), 7.31 (s, 2H), 6.56 (s, 1H), 3.00 (q, 2H, J=6.4 Hz), 2.38 (t, 2H, J=7.2 Hz), 2.07 (t, 2H, J=7.2 Hz), 1.73 (quint., 2H J=7.2 Hz), 1.36 (m, 2H), 1.23 (s, 18H), 0.85 (t, 2H, J=6.4 Hz); $^{13}$C NMR (75 MHz, DMSO-d$_6$) δ 171.20, 146.66, 126.34, 108.59, 38.34, 34.32, 34.32, 31.15, 29.02, 28.86, 28.6, 28.55, 26.31, 23.78, 23.52, 21.94, 13.79; HRMS (ESI) calcd for C$_{19}$H$_{37}$N$_4$O (MH)$^+$ 337.2961, found 337.2964.

4-(2-amino-1H-imidazol-4-yl)-N-cyclopentyl-butyramide hydrochloride (13). Using the same general procedure as used for the synthesis of 8,2-amino-4-(3-cyclopentylcarbamoyl-propyl)-imidazole-1-carboxylic acid tert-butyl ester 28 (100 mg, 0.297 mmol) gave 13 (78 mg, 96%) as a pale yellow foam. $^1$H NMR (400 MHz, DMSO-d$_6$) δ 11.99 (s, 1H), 11.57 (s, 1H), 7.79 (d, 1H, J=7.2 Hz), 7.30 (s, 2H), 6.56 (s, 1H), 3.97 (m, 1H), 2.37 (t, 2H, J=7.2 Hz), 2.05 (t, 2H, J=7.2 Hz), 1.69-1.79 (m, 4H), 1.59 (m, 2H), 1.47 (m, 2H), 1.31 (m, 2H); $^{13}$C NMR (100 MHz, DMSO-d$_6$) δ 170.97, 146.74, 126.38, 108.72, 50.11, 34.36, 32.31, 23.81, 23.45, 23.62; HRMS (ESI) calcd for C$_{12}$H$_{21}$N$_4$O (MH)$^+$ 237.1709, found 237.1711.

4-(2-amino-1H-imidazol-4-yl)-1-morpholin-4-yl-butan-1-one hydrochloride (14). Using the same general procedure as used for the synthesis of 8,2-amino-4-(4-morpholin-4-yl-4-oxo-butyl)-imidazole-1-carboxylic acid tert-butyl ester 29 (44 mg, 0.133 mmol) gave 14 (25 mg, 70%) as a tan solid. $^1$H NMR (400 MHz, DMSO-d$_6$) δ 12.1 (s, 1H), 11.64 (s, 1H), 7.33 (s, 2H), 6.58 (s, 1H), 3.54 (m, 4H), 3.42 (m, 4H), 2.43 (t, 2H, J=7.2 Hz), 2.33 (t, 2H, J=7.2 Hz), 1.75 (quint., 2H, J=7.2 Hz); $^{13}$C NMR (75 MHz, DMSO-d$_6$) δ 170.27, 146.72, 126.39, 108.61, 66.04, 45.28, 31.05, 23.56, 23.17; HRMS (ESI) calcd for C$_{11}$H$_{19}$N$_4$O$_2$ (MH)$^+$ 239.1502, found 239.1503.

4-(2-amino-1H-imidazol-4-yl)-N-phenyl-butyramide hydrochloride (15). Using the same general procedure as used for the synthesis of 8,2-amino-4-(3-phenylcarbamoyl-propyl)-imidazole-1-carboxylic acid tert-butyl ester 30 (80 mg, 0.232 mmol) gave 15 (64 mg, 99%) as a tan solid. $^1$H NMR (400 MHz, DMSO-d$_6$) δ 12.03 (s, 1H), 11.60 (s, 1H), 9.98 (s, 1H), 7.59 (d, 2H, J=8.0 Hz), 7.33 (br s, 2H), 7.28 (t, 2H, J=8.0 Hz), 7.02 (t, 1H, J=7.6 Hz), 6.61 (s, 1H), 2.44 (m, 2H), 2.32 (t, 2H, J=6.8 Hz), 1.85 (m, 2H); $^{13}$C NMR (75 MHz, DMSO-d$_6$) δ 170.65, 146.77, 139.25, 137.24, 128.59, 126.40, 123.00, 119.13, 108.83, 35.33, 23.60, 23.51; HRMS (ESI) calcd for C$_{13}$H$_{17}$N$_4$O (MH)$^+$ 245.1396, found 245.1401.

4-(2-amino-1H-imidazol-4-yl)-N-pyrimidin-2-yl-butyramide hydrochloride (16). Using the same general procedure as used for the synthesis of 8,2-amino-4-[3-(pyrimidin-2-ylcarbamoyl)-propyl]-imidazole-1-carboxylic acid tert-butyl ester 31 (50 mg, 0.144 mmol) gave 16 (41 mg, 99%) as a white solid. $^1$H NMR (400 MHz, DMSO-d$_6$) δ 12.06 (s, 1H), 11.64 (s, 1H), 10.59 (s, 1H), 8.64 (d, 2H, J=4.8 Hz), 7.34 (s, 2H), 7.17 (t, 1H, J=4.8 Hz), 6.60 (s, 1H), 2.51 (m, 2H), 2.46 (t, 2H, J=7.2 Hz), 1.83 (quint., 2H, J=7.2 Hz); $^{13}$C NMR (75 MHz, DMSO-d$_6$) δ 158.17, 157.54, 146.73, 129.02, 126.33, 116.5, 108.71, 35.35, 23.48, 23.09; HRMS (ESI) calcd for C$_{11}$H$_{15}$N$_{60}$ (MH)$^+$ 247.1301. found 247.1304.

Example 4

Library of Oroidin Derivatives Compound numbering for Example 4 applies only to Example 4. Two members of the oroidin family, bromoageliferin and oroidin, were documented to possess anti-biofouling properties by inhibiting biofilm development in the marine α-proteobacterium R. salexigens (A. Yamada et al., Bull. Chem. Soc. Jpn. 1997, 70, 3061). A library of analogues was synthesized based upon the oroidin template. Molecules based on oroidin would require a relatively short reaction sequence to access (2-6 steps) and could be rapidly assembled from core scaffolds and screened for their anti-biofilm properties. Herein we provide the synthesis of a 50 compound oroidin library. Marine natural products provide a diverse array of chemical structures and are known to possess a plethora of biological activities (M. D. Lebar, et al., Nat. Prod. Rep. 2007, 24, 774). Most members of the oroidin alkaloid family have nitrogen-dense architectures that contain a 2-aminoimidazole (2-AI) subunit (H. Hoffmann, T. Lindel, Synthesis-Stuttgart 2003, 1753; S. M. Weinreb, Nat. Prod. Rep. 2007, 24, 931). These compounds are typically found in sponges of the family Agelasidae and mainly serve as a chemical anti-feeding defense mechanism against predators (J. C. Braekman, et al., Biochem. Syst. Ecol. 1992, 20, 417). Oroidin is believed to be one of the main building blocks in the biosynthesis of other more complex family members including palau'amine and the stylissadines (A. Al Mourabit, P. Potier, Eur. J. Org. Chem. 2001, 237; M. Kock, et al., Angew. Chem., Int. Ed. 2007, 46, 6586). In addition to being documented to interfere with the biofouling process of R. salexigens, oroidin has also been observed to retard bacterial attachment and colonization in a limited number of studies (S. R. Kelly, et al., Aqua. Microb. Ecol. 2005, 40, 191; S. R. Kelly, et al., Aquat. Microb. Ecol. 2003, 31, 175).

Figure 3:
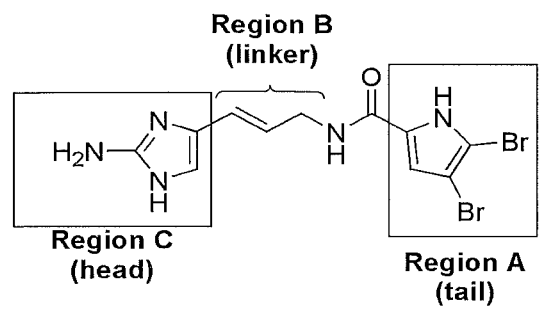
FIG. 3. Fragmentation of the oroidin template.
Figure 4:
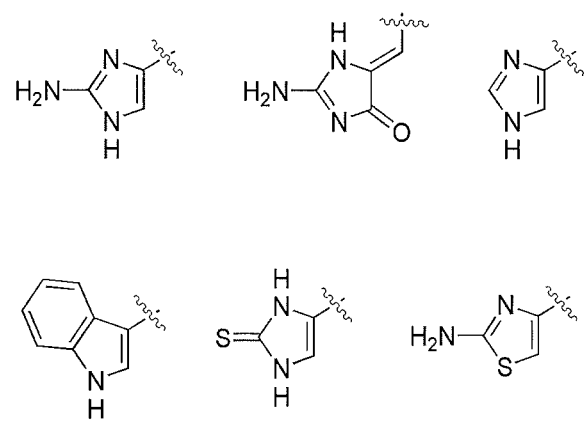
FIG. 4. Region C design.

Using this natural product as our base, a focused library was constructed by systematically varying three regions within the oroidin template (FIG. 3). These areas were designated as: the tail group (Region A), the linker chain (Region B), and the head group (Region C). The tail group was varied as: absent, an N—H pyrrole derivative, or an N-methyl pyrrole derivative. The linker between the head group and tail group was varied from two to four carbons and the effect of chain unsaturation was also examined. The head groups considered for analysis included 2-aminoimidazole, 2-amino-4-oxoimidazole, imidazole, tryptophan, 2-thioimidazolone, and 2-aminothiazole (FIG. 4).

Region A: Tail-Group analogue synthesis. Nearly all oroidin alkaloids are known to contain the pyrrole carboxamide moiety with various degrees of bromination and this provided the first structural element for investigation (H. Hoffmann, T. Lindel, Synthesis-Stuttgart 2003, 1753). Each analogue was prepared by a convergent synthetic approach with amide bond formation between the scaffold 4-(3-aminopropyl)-2-aminoimidazole dihydrochloride 16 and the appropriate trichloroacetyl pyrrole derivative serving as the final step. Trichloroacetyl pyrroles are known to undergo smooth amide bond formation in the presence of an unprotected 2-aminoimidazole and are among the most frequently used reagents in the total synthesis of many oroidin relatives (V. B. Birman, X. T. Jiang, Org. Lett. 2004, 6, 2369; D. P. O'Malley, et al., J. Am. Chem. Soc. 2007, 129, 4762). The necessary trichloroacetyl pyrroles were synthesized as outlined in Scheme 6 (D. M. Bailey, R. E. Johnson, J. Med. Chem. 1973, 16, 1300). The corresponding N—H and N-methyl dibromo carboxylic acids 11 and 15 were also prepared. These simple compounds are frequently isolated in high concentrations in conjunction with the more complex oroidin alkaloids from the Agelasidae sponges (A. E. Wright, et al., J. Nat. Prod. 1991, 54, 1684).

Scheme 6.

6 → 7 X = H, Y = Br (93%)
8 X = Y = Br (91%)
9 X = Y = Cl (70%)

10 → 11

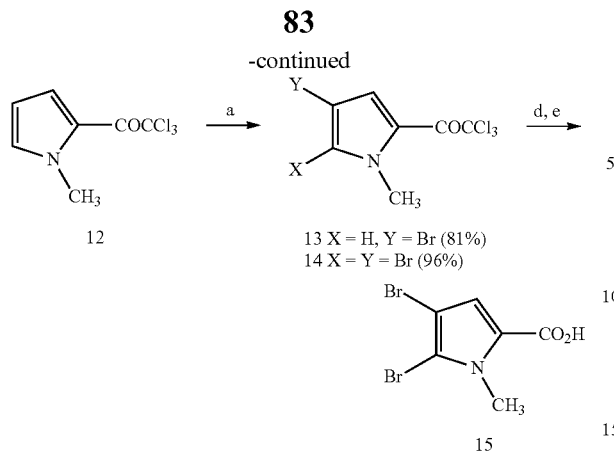

Synthesis of pyrrole subunits for Region A SAR; Reaction conditions:
(a) Br$_2$, CHCl$_3$, 0° C. (b) SO$_2$Cl$_2$, CHCl$_3$, reflux (c) Br$_2$, HOAc, CHCl$_3$, 50° C., 87%
(d) K$_2$CO$_3$, MeOH, 92% (e) LiOH, MeOH/THF/H$_2$O, 94%.

Both bromine atoms were replaced with less sterically demanding and less electronegative chlorine atoms (20). No known oroidin family members possess chlorine substituents on the pyrrole carboxamide subunit yet some do contain chlorinated positions in other parts of the molecule (M. Kock, et al., *Angew. Chem., Int. Ed.* 2007, 46, 6586). A methyl substituent was also introduced on the pyrrole nitrogen. This decision was based upon the observation that some naturally occurring members of the oroidin family (i.e. sventrin 24) contain an N-methylated pyrrole instead of the more commonly seen N—H pyrrole moiety (M. Assmann, et al., *J. Nat. Prod.* 2001, 64, 1593).

Region B: Linker analogue synthesis. The double bond found in oroidin is proposed to have a profound impact on the ability of the sponge to synthesize a number of more complex chemical skeletons (i.e. ageliferins, sceptrins) through dimerization type reactions (A. Al Mourabit, P. Potier, *Eur. J. Org. Chem.* 2001, 237). Discerning whether or not unsaturation was necessary for a biological response from an anti-biofilm standpoint would allow us to circumvent a low yielding extra synthetic step needed to install the double bond between the 3-4 positions in the dihydro scaffold 16. Oroidin 5 was prepared as previously reported (A. Olofson, et al., *J. Org. Chem.* 1998, 63, 1248). Sventrin 24 was synthesized using an identical synthetic approach executed for oroidin with the exception of employing 14 in the amide bond formation step.

Homologues of dihydrosventrin (DHS) that contained a 2-methylene and a 4-methylene spacer between the 2-AI head and the pyrrole tail were quickly accessed as outlined in Scheme 7. Briefly, commercially available 1,4-diamino-2-butanone dihydrochloride 25 was condensed with cyanamide under pH-controlled conditions to yield the 2-methylene spacer 2-AI 26 (T. Vitali, et al., *Farmaco* 1984, 39, 70), which was subsequently coupled to fragment 14 to deliver target 27. The 4-methylene spacer was generated through Akabori reduction of lysine methyl ester 28 to produce the corresponding α-amino aldehyde (Akabori, *Ber. Deut. Chem. Ges.* 1933, 66, 151; G. C. Lancini, E. Lazzari, *J. Heterocycl. Chem.* 1966, 3, 152), which, upon cyclization with cyanamide and ensuing amide bond formation, afforded the 2-AI 30.

Scheme 7.

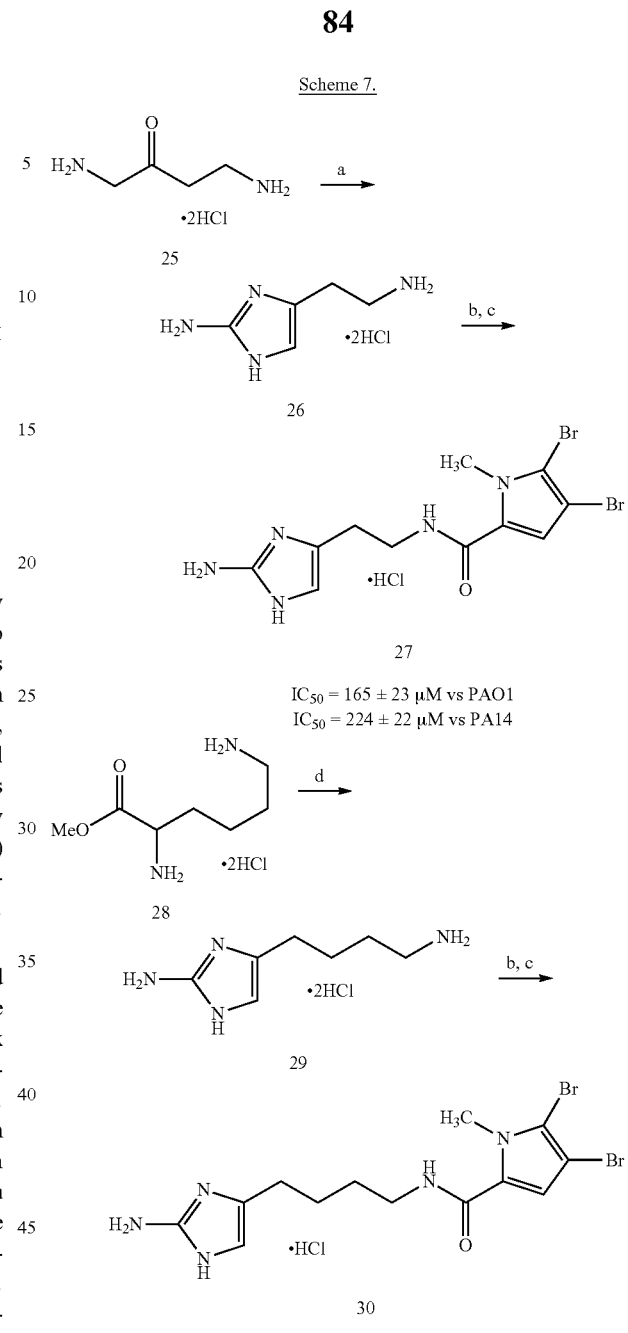

Region B linker synthesis; Reaction conditions: (a) NH$_2$CN, H$_2$O, 95° C., pH = 4.3, 62% (b) 14, Na$_2$CO$_3$, DMF, rt (c) HCl in MeOH, 27: 64%, 30: 54% (d) Na/Hg, H$_2$O, 5° C., pH = 1.5 then NH$_2$CN, H$_2$O, 95° C., pH = 4.3, 18%.

Region C: Head-Group analogue synthesis. Given the ubiquitous nature of the 2-aminoimidazole group in oroidin alkaloids, a substantial effort was made to delineate the importance of the 2-AI head group. We first focused on determining the ramifications of oxidizing the 2-AI ring at the 4-position. The natural product dispacamide (F. Cafieri, et al., *Tet. Lett.* 1996, 37, 3587) 31 and its N-methyl congener 32 were synthesized. Dispacamide was prepared as previously reported (A. Olofson, et al., *J. Org. Chem.* 1998, 63, 1248) while dihydrosventrin 23 was also oxidized with molecular bromine in DMSO to afford its requisite N-methyl analogue.

Atomic deletion or full head group replacement within Region C were synthesized next. The 2-AI group was replaced with a tryptophan residue (Scheme 8) or an imidazole group lacking the 2-amino group (Scheme 9). It was deemed unnecessary to delineate a synthesis for a 3-carbon linker of trytophan and imidazole when their 2-carbon homologues were commercially available and could be directly compared to the corresponding 2-AI derivative with a 2-methylene unit linker which had already been characterized. Tryptamine hydrochloride or histamine dihydrochloride were coupled to all of the different trichloroacetyl pyrroles discussed in the Region A.

Scheme 8. Region C tryptophan.

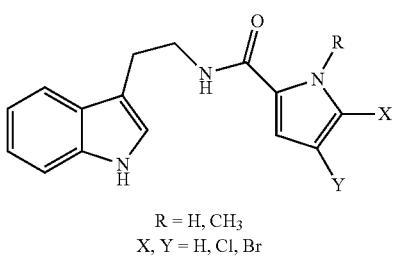

R = H, CH$_3$
X, Y = H, Cl, Br

Scheme 9. Region C synthesis.

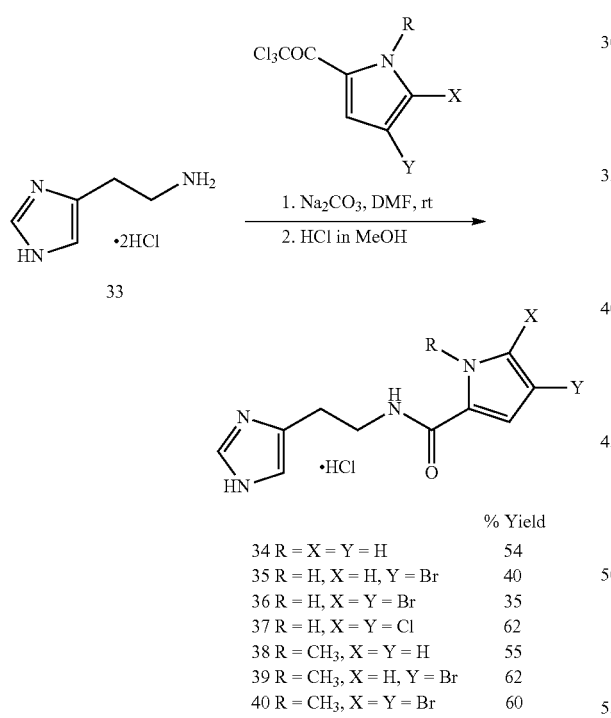

| | % Yield |
|---|---|
| 34 R = X = Y = H | 54 |
| 35 R = H, X = H, Y = Br | 40 |
| 36 R = H, X = Y = Br | 35 |
| 37 R = H, X = Y = Cl | 62 |
| 38 R = CH$_3$, X = Y = H | 55 |
| 39 R = CH$_3$, X = H, Y = Br | 62 |
| 40 R = CH$_3$, X = Y = Br | 60 |

Finally, single atom changes within the 2-AI subunits, the 2-thioimidazolone and 2-aminothiazole (2-AT) scaffolds, were synthesized. Condensation of an α-amino carbonyl compound with an isocyanate is well known, (A. C. B. Sosa, et al., *Org. Lett.* 2000, 2, 3443) and provided the basis for the synthesis of the 2-thioimidazolone scaffold 42. Similar to the known route to access 2-AI scaffold 16, Akabori reduction of ornithine methyl ester followed immediately by cyclization with KSCN under pH controlled conditions afforded the 2-thioimidazolone 42. Acylation of the terminal amine was accomplished with conditions adopted from the Region A synthesis to afford 43-49 in modest yields (Scheme 10).

Scheme 10. Region C synthesis.

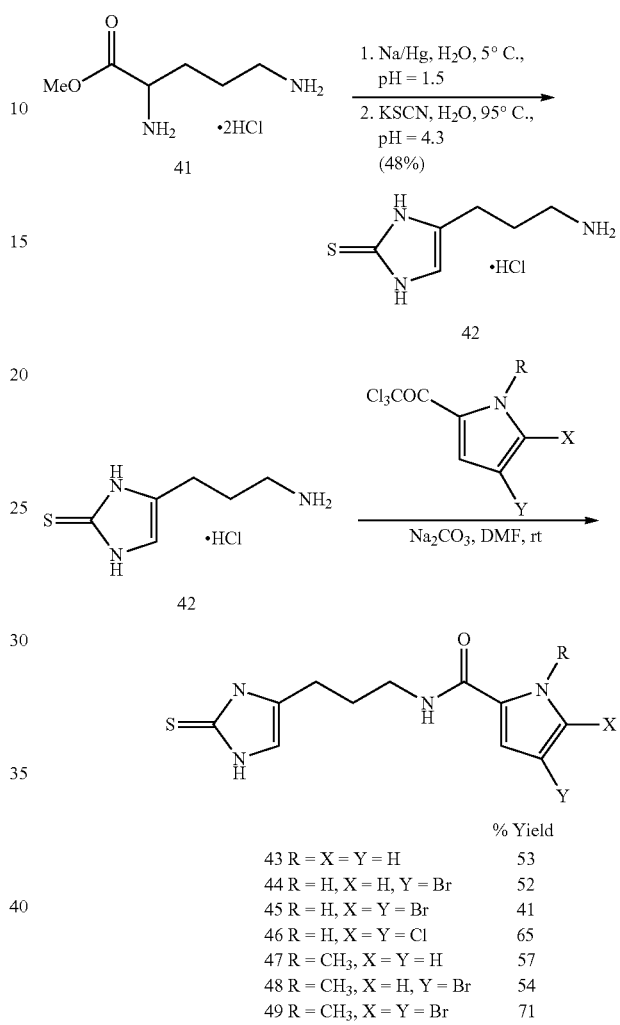

| | % Yield |
|---|---|
| 43 R = X = Y = H | 53 |
| 44 R = H, X = H, Y = Br | 52 |
| 45 R = H, X = Y = Br | 41 |
| 46 R = H, X = Y = Cl | 65 |
| 47 R = CH$_3$, X = Y = H | 57 |
| 48 R = CH$_3$, X = H, Y = Br | 54 |
| 49 R = CH$_3$, X = Y = Br | 71 |

2-AT's are known to possess biological activity and thus were deemed a logical choice for head group study (J. C. Eriks, et al., *J. Med. Chem.* 1992, 35, 3239; J. L. Kane, et al., *Bioorg. Med. Chem. Lett.* 2003, 13, 4463). To affect the synthesis of the 2-AT scaffold, a new synthetic plan was necessary to selectively install a sulphur atom at the 1-position in the ring (Scheme 11). Synthesis commenced with acyl chloride formation of the known 4-phthalimidobutanoic acid 50 (W. J. Kruper, et al., *J. Org. Chem.* 1993, 58, 3869). This was followed by diazomethane homologation and concomitant quench with concentrated HBr, which afforded the α-bromoketone. Cyclization of the α-bromoketone with thiourea under neutral conditions cleanly and regioselectively installed the 2-AT ring (51) (J. C. Eriks, et al., *J. Med. Chem.* 1992, 35, 3239). A. Hantzsch, V. Traumann, *Berichte* 1888, 21, 938. Deprotection of the phthalamide protecting group was accomplished with hydrazine in methanol to deliver the 2-AT scaffold. Again, acylation of the terminal amine was accomplished as previously outlined to afford the final target analogues.

Scheme 11.

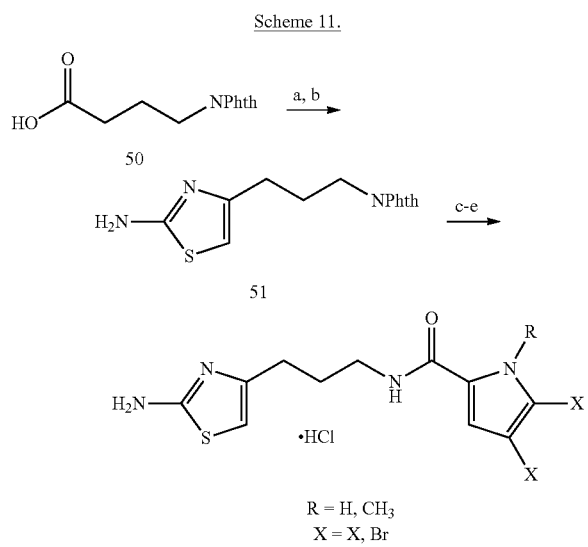

R = H, CH₃
X = X, Br

Region C synthesis; Reaction conditions: (a) i. (COCl)₂ DMF (cat.), CH₂Cl₂
ii. CH₂N₂, Et₂O/CH₂Cl₂, 0° C. iii. conc. HBr, 84% (b) thiourea, DMF, 0° C.
to 25° C., 97% (c) N₂H₄, MeOH, 25° C. to 55° C., 90% (d) K₂CO₃, 6/8/12/14,
DMF (e) HCl in MeOH.

All reagents including anhydrous solvents used for the chemical synthesis of the library were purchased from commercially available sources and used without further purification unless otherwise noted. All reactions were run under either a nitrogen or argon atmosphere. Flash silica gel chromatography was performed with 60 Å mesh standard grade silica gel from Sorbtech. $^1$H and $^{13}$C NMR spectra were obtained using Varian 300 MHz or 400 MHz spectrometers. NMR solvents were purchased from Cambridge Isotope Labs and used as received. Chemical shifts are given in parts per million relative to DMSO-$d_6$ ($\delta$ 2.50), CD$_3$OD ($\delta$ 3.31) and CDCl$_3$ ($\delta$ 7.27) for proton spectra and relative to DMSO-$d_6$ ($\delta$ 39.51), CD$_3$OD ($\delta$ 49.00) and CDCl$_3$ ($\delta$ 77.21) for carbon spectra with an internal TMS standard. High-resolution mass spectra were obtained at the North Carolina State Mass Spectrometry Laboratory for Biotechnology. FAB experiments were carried with a JOEL HX110HF mass spectrometer while ESI experiments were carried out on Agilent LC-TOF mass spectrometer.

1-(4-bromo-1H-pyrrol-2-yl)-2,2,2-trichloro-ethanone (7). 2-Trichloroacetyl pyrrole 6 (5.00 g, 23.3 mmol) was dissolved in anhydrous chloroform (20 mL) The solution was cooled to −10° C. before the drop-wise addition of bromine (1.20 mL, 23.3 mmol) to the flask. Once addition was complete the reaction was allowed to warm to room temperature on its own accord while stirring for an additional 30 minutes. The reaction was poured into water (40 mL) and extracted with chloroform (3×20 mL) The combined organic layers were washed with sat. NaHCO$_3$ (2×30 mL), brine (1×20 mL), dried over anhydrous sodium sulfate, filtered, and evaporated to dryness. Purification of the residue by column chromatography (Hexanes/Diethyl Ether 95:5) yielded the title compound 7 (6.37 g, 93%) as an off-white solid: $^1$H NMR (300 MHz, DMSO-$d_6$) $\delta$ 12.86 (s, 1H), 7.54 (s, 1H), 7.32 (s, 1H); $^{13}$C NMR (100 MHz, DMSO-$d_6$) $\delta$ 171.67, 129.06, 122.01, 121.54, 97.60, 94.56; HRMS (FAB) calcd for C$_6$H$_3$BrCl$_3$NO (M$^+$) 288.8464, found 288.8479.

1-(4-bromo-1-methyl-pyrrol-2-yl)-2,2,2-trichloro-ethanone (13). Using the same general procedure as used for the synthesis of 1-(4-bromo-1H-pyrrol-2-yl)-2,2,2-trichloro-ethanone 7, 5.00 g of 2-trichloroacetyl-1-methylpyrrole afforded 5.46 g (81%) of the title compound 13 as a white solid: $^1$H NMR (300 MHz, DMSO-$d_6$) $\delta$ 7.66 (d, 1H, J=1.2 Hz), 7.42 (d, 1H, J=1.8 Hz), 3.91 (s, 3H); $^{13}$C NMR (100 MHz, DMSO-$d_6$) $\delta$ 171.48, 134.40, 123.62, 121.19, 95.36, 95.12; HRMS (FAB) calcd for C$_7$H$_6$BrCl$_3$NO (MH$^+$) 303.8698, found 303.8678.

2,2,2-trichloro-1-(4,5-dibromo-1H-pyrrol-2-yl)-ethanone (8). 2-Trichloroacetyl pyrrole 6 (5.00 g, 23.3 mmol) was dissolved in anhydrous chloroform (20 mL) The solution was cooled to −10° C. before the drop-wise addition of bromine (2.64 mL, 51.3 mmol) to the reaction. Once addition was complete the reaction was allowed to warm to room temperature on its own accord while stirring for an additional 30 minutes. The reaction was poured into water (40 mL) and extracted with chloroform (3×20 mL). The combined organic layers were washed with sat. NaHCO$_3$ (2×30 mL), brine (1×20 mL), and dried over anhydrous sodium sulfate. Filtration and evaporation afforded the crude product which was recrystallized from hexanes to deliver 7.93 g (91%) of the title compound 8 as an off-white solid: $^1$H NMR (300 MHz, DMSO-$d_6$) $\delta$ 13.75 (s, 1H), 7.40 (s, 1H); $^{13}$C NMR (100 MHz, DMSO-$d_6$) $\delta$ 170.94, 123.30, 122.45, 114.62, 100.88, 94.08; HRMS (FAB) calcd for C$_6$H$_2$Br$_2$Cl$_3$NO (M$^+$) 366.7569, found 366.7556.

2,2,2-trichloro-1-(4,5-dibromo-1-methyl-pyrrol-2-yl)-ethanone (14). Using the same general procedure as used for the synthesis of 2,2,2-trichloro-1-(4,5-dibromo-1H-pyrrol-2-yl)-ethanone 8, 5.00 g of 2-trichloroacetyl-1-methylpyrrole 12 gave 8.14 g (96%) of the title compound 14 as white needles. $^1$H NMR (300 MHz, DMSO-$d_6$) $\delta$ 7.60 (s, 1H), 3.96 (s, 3H); $^{13}$C NMR (100 MHz, DMSO-$d_6$) $\delta$ 170.86, 123.81, 122.68, 120.58, 99.58, 94.89, 37.60; HRMS (FAB) calcd for C$_7$H$_4$Br$_2$Cl$_3$NO (M$^+$) 380.7725, found 380.7744.

2,2,2-trichloro-1-(4,5-dichloro-1H-pyrrol-2-yl)-ethanone (9). 2-Trichloroacetyl pyrrole 6 (5.00 g, 23.5 mmol) was dissolved in anhydrous chloroform (10 mL) and the reaction flask was covered in aluminum foil to exclude light. Sulfuryl chloride (4.20 mL, 51.8 mmol), was then charged in the flask and the reaction was refluxed for 16 h before being cooled to room temperature and poured into cold water (100 mL). The aqueous layer was removed and washed with dichloromethane (2×25 mL) The combined organic layers were then washed with sat. NaHCO$_3$ (3×35 mL), dried over anhydrous sodium sulfate, filtered, and concentrated in vacuo. The residue was purified by column chromatography (Hexanes/Diethyl Ether 95:5) to afford 4.61 g (70%) of the desired compound 9 as a white solid: $^1$H NMR (300 MHz, DMSO-$d_6$) $\delta$ 13.84 (s, 1H), 7.41 (s, 1H); $^{13}$C NMR (100 MHz, DMSO-$d_6$) $\delta$ 171.2, 123.6, 119.9, 119.7, 110.8, 94.8; HRMS (FAB) calcd for C$_6$H$_2$Cl$_5$NO (M$^+$) 278.8579, found 278.8573.

4,5-dibromo-1H-pyrrole-2-carboxylic acid (11). Pyrrole-2-carboxylic acid 10 (1.00 g, 9.00 mmol), was dissolved in anhydrous chloroform (10 mL) and glacial HOAc (2 mL). To the resulting cloudy solution was slowly added bromine (0.971 mL, 18.9 mmol) at room temperature and once addition was complete the reaction was heated to 50° C. for 5 h. After cooling to ambient temperature the reaction was partitioned between water (30 mL) and chloroform (40 mL). The organic layer was rinsed with water (2×30 mL) and 10% K$_2$CO$_3$ (40 mL). The K$_2$CO$_3$ extract was then washed with chloroform (2×20 mL) and acidified to pH=3 with an aqueous solution of 4N HCl. The precipitate was collected by vacuum filtration and the filter cake rinsed with water (15 mL) to afford the target compound 11 (2.10 g, 87%) as a white solid: $^1$H NMR (400 MHz, DMSO-$d_6$) $\delta$ 12.80 (bs, 1H), 6.82 (s, 1H); $^{13}$C NMR (100 MHz, DMSO-$d_6$) $\delta$ 160.43, 125.37, 116.73, 106.50, 98.70; HRMS (FAB) calcd for $C_5H_3Br_2NO$ (M$^+$) 266.8531, found 266.8525.

4,5-dibromo-1-methyl-pyrrole-2-carboxylic acid methyl ester. 2,2,2-Trichloro-1-(4,5-dibromo-1-methyl-1H-pyrrol-2-yl)-ethanone 14 (1.00 g, 2.60 mmol), anhydrous potassium carbonate (0.719 g, 5.20 mmol), and anhydrous methanol (20 mL) were charged into a reaction flask. The resulting suspension was stirred for 16 h at room temperature upon which the reaction was quenched with water (10 mL). The methanol was removed under reduced pressure and the residue partitioned between ethyl acetate (100 mL) and water (20 mL). The organic layer was subsequently washed with sat. NaHCO$_3$ (2×30 mL), brine (2×20 mL), dried over anhydrous sodium sulfate, and filtered. Evaporation of the filtrate yielded the title compound (0.710 g, 92%) as a white solid: $^1$H NMR (300 MHz, DMSO-d$_6$) δ 7.05 (s, 1H), 3.90 (s, 3H), 3.76 (s, 3H); $^{13}$C NMR (75 MHz, DMSO-d$_6$) δ 159.38, 123.62, 118.51, 113.93, 98.06, 51.58, 35.78; HRMS (FAB) calcd for $C_7H_7Br_2NO_2$ (M$^+$) 294.8844, found 294.8861.

4,5-dibromo-1-methyl-pyrrole-2-carboxylic acid (15). 4,5-dibromo-1-methyl-1H-pyrrole-2-carboxylic acid methyl ester (0.675 g, 2.27 mmol), lithium hydroxide (0.436 g, 18.19 mmol), methanol (12 mL), tetrahydrofuran (4 mL), and water (4 mL) were stirred for 16 h at ambient temperature. The pH was then adjusted to 7.0 with an aqueous solution of 4N HCl. The organics were removed by rotary evaporation and the resulting residue diluted with water (15 mL). Acidification of the aqueous layer to pH=3 with 4N HCl afforded a white solid which was collected by vacuum filtration. The filter cake was rinsed with water (10 mL) to give the title compound 15 (0.601 g, 94%) as a white solid: $^1$H NMR (400 MHz, DMSO-d$_6$) δ 12.83 (s, 1H), 7.00 (s, 1H), 3.90 (s, 3H); $^{13}$C NMR (100 MHz, DMSO-d$_6$) δ 160.51, 124.74, 118.41, 113.07, 97.72, 35.64; HRMS (FAB) calcd for $C_6H_5Br_2NO_2$ (M$^+$) 280.8687. found 280.8676.

4-(3-amino-propyl)-1H-imidazol-2-ylamine dihydrochloride (16). Prepared as previously reported.[37] $^1$H NMR (300 MHz, DMSO-d$_6$) δ 12.04 (br s, 1H), 8.25 (br s, 2H), 7.41 (s, 2H), 6.65 (s, 1H), 2.75 (t, 2H, J=7.2), 2.52 (m, 2H), 1.85 (tt, 2H, J=7.5, 14.7 Hz); $^{13}$C NMR (100 MHz, DMSO-d$_6$) δ 146.9, 125.4, 108.9, 37.7, 25.5, 21.1; HRMS (FAB) calcd for $C_6H_{12}N_3S$ (MH$^+$) 158.0752, found 158.0743.

1H-pyrrole-2-carboxylic acid [3-(2-amino-1H-imidazol-4-yl)-propyl]-amide hydrochloride (17). 4-(3-amino-propyl)-1H-imidazol-2-ylamine dihydrochloride 16 (0.100 g, 0.458 mmol), 2-trichloroacetyl pyrrole 6 (0.103 g, 0.488 mmol), and anhydrous sodium carbonate (0.172 g, 1.63 mmol), were dissolved in anhydrous N,N-dimethylformamide (5 mL). The reaction was stirred at ambient temperature for 16 h. Evaporation of the reaction under reduced pressure and purification of the residue by column chromatography (CH$_2$Cl$_2$/MeOH sat. NH$_3$ 85:15) afforded the desired compound in its free base form. Addition of a single drop of concentrated hydrochloric acid to a methanol solution (8 mL) and evaporation under reduced pressure yielded 0.078 g (63%) of the title compound 17 as a white solid: $^1$H NMR (300 MHz, DMSO-d$_6$) δ 12.07 (s, 1H), 11.59 (s, 1H), 11.45 (s, 1H), 8.14 (t, 1H, J=5.1 Hz), 7.30 (s, 2H), 6.81 (m, 2H), 6.74 (s, 1H), 6.59 (s, 1H), 6.04 (s, 1H), 3.19 (dt, 2H, J=6.6, 12.6 Hz), 2.42 (t, 2H, J=6.9 Hz), (tt, 2H, J=6.6, 13.8 Hz); $^{13}$C NMR (100 MHz, DMSO-d$_6$) δ 160.74, 146.76, 126.43, 126.40, 121.13, 110.28, 108.65, 108.50, 37.59, 28.14, 21.60; HRMS (ESI) calcd for $C_{11}H_{16}N_5O$ (MH$^+$) 234.1349, found 234.1354.

4-bromo-1H-pyrrole-2-carboxylic acid [3-(2-amino-1H-imidazol-4-yl)-propyl]-amide hydrochloride (18). Using the same general procedure as used for the synthesis of 1H-pyrrole-2-carboxylic acid [3-(2-amino-1H-imidazol-4-yl)-propyl]-amide hydrochloride 17, 0.132 g of 4-(3-amino-propyl)-1H-imidazol-2-ylamine dihydrochloride 16 gave the target compound 18 (0.159 g, 74%) as an off-white solid: $^1$H NMR (300 MHz, DMSO-d$_6$) δ 12.20 (s, 1H), 11.85 (s, 1H), 11.57 (s, 1H), 8.23 (m, 1H), 7.31 (s, 2H), 6.97 (d, 1H, J=1.5 Hz), 6.86 (d, 1H, J=1.5 Hz), 6.61 (s, 1H), 3.21 (m, 2H), 2.44 (t, 2H, J=7.2 Hz), 1.73 (m, 2H); $^{13}$C NMR (75 MHz, DMSO-d$_6$) δ 159.63, 146.68, 126.99, 126.40, 121.06, 111.61, 108.70, 94.90, 37.67, 27.91, 21.56; HRMS (FAB) calcd for $C_{11}H_{15}BrN_5O$ (MH$^+$) 312.0460, found 312.0475.

4,5-dibromo-1H-pyrrole-2-carboxylic acid [3-(2-amino-1H-imidazol-4-yl)-propyl]-amide hydrochloride (19). Using the same general procedure as used for the synthesis of 1H-pyrrole-2-carboxylic acid [3-(2-amino-1H-imidazol-4-yl)-propyl]-amide hydrochloride 17, 0.100 g of 4-(3-amino-propyl)-1H-imidazol-2-ylamine dihydrochloride 16 afforded 0.117 g (59%) of the title compound 19 as an off-white solid: $^1$H NMR (300 MHz, DMSO-d$_6$) δ 8.33 (t, 1H, J=5.4 Hz), 7.07 (s, 2H), 6.95 (s, 1H), 6.56 (s, 1H), 3.22 (dt, 2H, J=6.0, 12.3 Hz), 2.43 (t, 2H, J=7.2 Hz), 1.73 (tt, J=6.9, 13.8 Hz); $^{13}$C NMR (100 MHz, DMSO-d$_6$) δ 158.92, 146.87, 128.31, 126.75, 112.88, 108.82, 104.33, 97.76, 37.74, 27.89, 21.74; HRMS (FAB) calcd for $C_{11}H_{14}Br_2N_5O$ (MH$^+$) 389.9565, found 389.9570.

4,5-dichloro-1H-pyrrole-2-carboxylic acid [3-(2-amino-1H-imidazol-4-yl)-propyl]-amide hydrochloride (20). Using the same general procedure as used for the synthesis of 1H-pyrrole-2-carboxylic acid [3-(2-amino-1H-imidazol-4-yl)-propyl]-amide hydrochloride 17, 0.200 g of 4-(3-amino-propyl)-1H-imidazol-2-ylamine dihydrochloride 16 afforded 0.204 g (65%) of the title compound 20 as a white solid: $^1$H NMR (300 MHz, DMSO-d$_6$) δ 8.32 (t, 1H, J=4.8 Hz), 6.91 (s, 2H), 6.53 (s, 1H), 3.21 (dt, 2H, J=6.6, 12.6 Hz), 2.42 (t, 2H, J=7.2 Hz), 1.72 (tt, 2H, J=7.5, 14.1 Hz); $^{13}$C NMR (75 MHz, DMSO-d$_6$) δ 159.15, 147.11, 127.31, 125.14, 114.75, 109.82, 108.99, 107.77, 37.83, 28.03, 22.04; HRMS (ESI) calcd for $C_{11}H_{14}Cl_2N_5O$ (MH$^+$) 302.0569, found 302.0569.

1-methyl-pyrrole-2-carboxylic acid [3-(2-amino-1H-imidazol-4-yl)-propyl]-amide hydrochloride (21). Using the same general procedure as used for the synthesis of 1H-pyrrole-2-carboxylic acid [3-(2-amino-1H-imidazol-4-yl)-propyl]-amide hydrochloride 17, 0.300 g of 4-(3-amino-propyl)-1H-imidazol-2-ylamine dihydrochloride 16 delivered 0.229 g (58%) of the target compound 21 as a pale yellow solid: $^1$H NMR (300 MHz, DMSO-d$_6$) δ 8.03 (t, 1H, J=5.1 Hz), 6.86 (m, 1H), 6.75 (m, 1H), 6.32 (s, 1H), 5.98 (m, 1H), 5.86 (br s, 2H), 3.82 (s, 3H), 3.17 (dt, 2H, J=6.3, 13.2 Hz), 2.36 (t, 2H, J=7.2 Hz), (tt, 2H, J=7.2, 14.1 Hz); $^{13}$C NMR (75 MHz, DMSO-d$_6$) δ 161.39, 148.11, 129.74, 127.47, 125.72, 112.09, 109.63, 106.53, 38.00, 36.15, 28.65, 23.30; HRMS (ESI) calcd for $C_{12}H_{18}N_5O$ (MH$^+$) 248.1506, found 248.1514.

4-bromo-1-methyl-pyrrole-2-carboxylic acid [3-(2-amino-1H-imidazol-4-yl)-propyl]-amide hydrochloride (22). Using the same general procedure as used for the synthesis of 1H-pyrrole-2-carboxylic acid [3-(2-amino-1H-imidazol-4-yl)-propyl]-amide hydrochloride 17, 0.150 g of 4-(3-amino-propyl)-1H-imidazol-2-ylamine dihydrochloride 16 afforded 0.142 g (56%) of the desired compound 22 as a pale yellow solid: $^1$H NMR (300 MHz, DMSO-d$_6$) δ 8.17 (t, 1H, J=5.7 Hz), 7.08 (d, 1H, J=1.2 Hz), 6.91 (s, 2H), 6.85 (d, 1H, J=1.5 Hz), 6.52 (s, 1H), 3.80 (s, 3H), 3.17 (dt, 2H, J=6.3, 12.9 Hz), 2.41 (t, 2H, J=7.2 Hz), 1.71 (m, 2H); $^{13}$C NMR (100 MHz, DMSO-d$_6$) δ 160.29, 147.23, 127.39, 126.87, 126.43, 113.60, 108.94, 92.89, 37.75, 36.33, 28.02, 22.08; HRMS (ESI) calcd for $C_{12}H_{17}BrN_5O$ (MH$^+$) 326.0610, found 326.0613.

4,5-dibromo-1-methyl-pyrrole-2-carboxylic acid [3-(2-amino-1H-imidazol-4-yl)-propyl]-amide hydrochloride (23). Using the same general procedure as used for the synthesis of 1H-pyrrole-2-carboxylic acid [3-(2-amino-1H-imidazol-4-yl)-propyl]-amide hydrochloride 17, 0.200 g of 4-(3-amino-propyl)-1H-imidazol-2-ylamine dihydrochloride 16 gave 0.258 g (63%) of the title compound 23 as a white solid: $^1$H NMR (300 MHz, DMSO-d$_6$) δ 12.06 (s, 1H), 11.59 (s, 1H), 8.31 (t, 1H, J=5.4 Hz), 7.32 (s, 2H), 7.03 (s, 1H), 6.60 (s, 1H), 3.87 (s, 3H), 3.18 (dt, 2H, J=6.3, 12.3 Hz), 2.45 (t, 2H, J=7.8 Hz), 1.73 (m, 2H); $^{13}$C NMR (75 MHz, DMSO-d$_6$) δ 159.77, 147.30, 127.99, 127.77, 114.00, 110.43, 109.06, 96.86; 37.94, 35.38, 27.96, 22.28; HRMS (FAB) calcd for C$_{12}$H$_{16}$Br$_2$N$_5$O (MH$^+$) 403.9722, found 403.9728.

oroidin hydrochloride (5). Prepared as previously reported.[37] $^1$H NMR (300 MHz, DMSO-d$_6$) δ 12.78 (s, 1H), 12.54 (s, 1H), 11.89 (s, 1H), 8.55 (t, 1H, J=6.0 Hz), 7.47 (s, 2H), 6.99 (d, 1H, J=3.0 Hz), 6.90 (s, 1H), 6.17 (m, 2H), 3.95 (m, 2H); $^{13}$C NMR (100 MHz, DMSO-d$_6$) δ 158.73, 147.46, 127.99, 126.85, 124.84, 116.15, 112.81, 111.15, 104.74, 97.91, 39.83; HRMS (FAB) calcd for C$_{11}$H$_{12}$Br$_2$N$_5$O (MH$^+$) 387.9409, found 387.9402.

sventrin hydrochloride (24). Using the same general procedure as used for the synthesis of 1H-pyrrole-2-carboxylic acid [3-(2-amino-1H-imidazol-4-yl)-propyl]-amide hydrochloride 17, 0.050 g of 4-(3-amino-propenyl)-1H-imidazol-2-ylamine dihydrochloride afforded 0.062 g (61%) of sventrin hydrochloride 24 as a pale yellow solid: $^1$H NMR (400 MHz, DMSO-d$_6$) δ 8.49 (t, 1H, J=5.6 Hz), 7.06 (s, 1H), 6.77 (s, 2H), 6.75 (s, 1H), 6.19 (d, 1H, J=15.6 Hz), 6.02 (dt, 1H, J=5.6, 11.2 Hz), 3.94 (m, 2H), 3.89 (s, 3H); $^{13}$C NMR (100 MHz, DMSO-d$_6$) δ 159.57, 147.44, 127.59, 126.75, 124.85, 116.25, 114.17, 111.20, 110.88, 96.98, 35.45; HRMS (ESI) calcd for C$_{12}$H$_{14}$Br$_2$N$_5$O (MH$^+$) 401.9560, found 401.9560.

4-(2-amino-ethyl)-1H-imidazol-2-ylamine dihydrochloride (26). 1,4-diamino-2-butanone dihydrochloride 25 (0.300 g, 1.71 mmol) and cyanamide (0.753 g, 17.9 mmol) were dissolved in water (10 mL). The pH of the solution was adjusted to pH=4.3 before heating the reaction at 95° C. for 3.5 h while open to the atmosphere. After cooling to ambient temperature ethanol (10 mL) was added to the flask and the solution was evaporated to dryness. Purification of the residue by column chromatography (MeOH sat. with NH$_3$/CH$_2$Cl$_2$ 90:10) yielded the product as its corresponding free base. Addition of methanol (10 mL) and concentrated hydrochloric acid followed by evaporation in vacuo afforded the target compound 26 (0.211 g, 62%) as a yellow solid: $^1$H NMR (300 MHz, DMSO-d$_6$) δ 6.21 (s, 1H), 5.14 (br s, 2H), 2.81 (m, 2H), 2.47 (m, 2H); HRMS (ESI) calcd for C$_5$H$_{11}$N$_4$ (MH$^+$) 127.0978, found 127.0977.

4,5-dibromo-1-methyl-pyrrole-2-carboxylic acid [2-(2-amino-1H-imidazol-4-yl)-ethyl]-amide hydrochloride (27). Using the same general procedure as used for the synthesis of 1H-pyrrole-2-carboxylic acid [3-(2-amino-1H-imidazol-4-yl)-propyl]-amide hydrochloride 17, 0.150 g of 4-(2-amino-ethyl)-1H-imidazol-2-ylamine dihydrochloride 26 afforded 0.206 g (64%) of the title compound 27 as an off-white solid: $^1$H NMR (300 MHz, DMSO-d$_6$) δ 8.24 (t, 1H, J=5.1 Hz), 6.95 (s, 1H), 6.20 (s, 1H), 5.02 (s, 2H), 3.87 (s, 3H), 3.31 (m, 2H); $^{13}$C NMR (75 MHz, DMSO-d$_6$) δ 159.54, 149.20, 128.14, 113.86, 113.69, 110.33, 99.14, 96.83, 35.33, 27.45; HRMS (ESI) calcd for C$_{11}$H$_{14}$Br$_2$N$_5$O (MH$^+$) 389.9559. found 389.9574.

4-(4-amino-butyl)-1H-imidazol-2-ylamine dihydrochloride (29). Using the same general procedure as used for the synthesis of 4-(3-amino-propyl)-1H-imidazol-2-ylamine dihydrochloride 16, 12.5 g of lysine methyl ester dihydrochloride 28 afforded 2.25 g (18%) of the target compound 29 as a yellow solid: $^1$H NMR (300 MHz, DMSO-d$_6$) δ 6.09 (s, 1H), 4.96 (s, 2H), 2.56 (t, 2H, J=6.3 Hz), 2.27 (t, 2H, J=6.9 Hz), 1.35-1.51 (m, 4H); $^{13}$C NMR (100 MHz, DMSO-d$_6$) δ 149.11, 132.29, 110.59, 40.75, 31.41, 26.62, 26.12; HRMS (ESI) calcd for C$_7$H$_{15}$N$_4$ (MH$^+$) 155.1291, found 155.1293.

4,5-dibromo-1-methyl-pyrrole-2-carboxylic acid [4-(2-amino-1H-imidazol-4-yl)-butyl]-amide hydrochloride (30). Using the same general procedure as used for the synthesis of 1H-pyrrole-2-carboxylic acid [3-(2-amino-1H-imidazol-4-yl)-propyl]-amide hydrochloride 17, 0.200 g of 4-(4-amino-butyl)-1H-imidazol-2-ylamine dihydrochloride 29 delivered 0.216 g (54%) of the target compound 30 as a pale yellow solid: $^1$H NMR (300 MHz, DMSO-d$_6$) δ 8.20 (t, 1H, J=5.1 Hz), 6.99 (s, 1H), 6.35 (s, 1H), 6.29 (bs, 2H), 3.86 (s, 3H), 3.17 (m, 2H), 2.35 (m, 2H), 1.49 (m, 4H); $^{13}$C NMR (100 MHz, DMSO-d$_6$) δ 159.66, 147.48, 128.39, 128.06, 113.86, 110.37, 109.17, 96.85, 38.23, 35.35, 28.51, 25.48, 24.53; HRMS (ESI) calcd for C$_{13}$H$_{18}$Br$_2$N$_5$O (MH$^+$) 417.9873, found 417.9870.

2-amino-5-(3-amino-propylidene)-1,5-dihydro-imidazol-4-one dihydrochloride. 4-(3-amino-propyl)-1H-imidazol-2-ylamine 16 (0.200 g, 0.930 mmol) was dissolved in anhydrous dimethyl sulfoxide (6 mL) Bromine (0.047 mL, 0.930 mmol) was added drop-wise and the solution was stirred at room temperature for 1 h. Diethyl ether (7 mL) was added and the organics were then decanted. The residue was purified by column chromatography (MeOH sat. with NH$_3$) to yield the desired product as its free base. Addition of concentrated hydrochloric acid to a methanol solution (8 mL) of the free base followed by evaporation under reduced pressure afforded the target compound ((Z)-isomer exclusively) (0.141 g, 67%) as a tan solid: $^1$H NMR (300 MHz, DMSO-d$_6$) δ 12.10 (br s, 1H), 9.20 (br s, 2H), 8.18 (br s, 2H), 5.92 (t, 1H, J=7.8 Hz), 2.96 (m, 2H), 2.66 (m, 2H); $^{13}$C NMR (100 MHz, DMSO-d$_6$) δ 164.13, 156.63, 130.88, 113.70, 37.57, 24.94; HRMS (FAB) calcd for C$_6$H$_{10}$N$_4$O (MH$^+$) 155.0933, found 155.0943.

dispacamide hydrochloride (31). Using the same general procedure as used for 2-amino-5-(3-amino-propylidene)-1,5-dihydro-imidazol-4-one dihydrochloride, 0.185 g of dihydrooroidin hydrochloride 19 gave 0.120 g (63%) of dispacamide hydrochloride (8:1 Z/E isomer) 31 as a tan solid: $^1$H NMR (300 MHz, CD$_3$OD) (Z isomer) δ 6.79 (s, 1H), 6.14 (t, 1H, J=7.8 Hz), 3.46 (t, 2H, J=6.9 Hz), 2.58 (dt, 2H, J=6.9, 14.7 Hz); $^{13}$C NMR (75 MHz, DMSO-d$_6$) δ 164.32, 162.06, 157.58, 130.90, 128.75, 119.09, 114.51, 106.47, 100.15, 39.11, 28.81; HRMS (ESI) calcd for C$_{11}$H$_{12}$Br$_2$N$_5$O$_2$ (MH$^+$) 403.9352, found 403.9350.

4,5-dibromo-1-methyl-pyrrole-2-carboxylic acid [3-(2-amino-5-oxo-3,5-dihydro-imidazol-4-ylidene)-propyl]-amide hydrochloride (32). Using the same general procedure as used for 2-amino-5-(3-amino-propylidene)-1,5-dihydro-imidazol-4-one dihydrochloride, 0.100 g of dihydrosventrin hydrochloride 23 gave 0.048 g (47%) of the title compound 32 as a tan solid ((Z)-isomer exclusively). $^1$H NMR (300 MHz, CD$_3$OD) δ 6.84 (s, 1H), 6.16 (t, 1H, J=7.8 Hz), 3.91 (s, 3H), 3.46 (t, 2H, J=6.9 Hz), 2.59 (dt, 2H, J=6.9, 14.7 Hz); $^{13}$C NMR (100 MHz, DMSO-d$_6$) δ 163.80, 163.00, 157.19, 130.63, 129.04, 119.42, 115.92, 112.67, 99.09, 39.06, 36.28, 28.73; HRMS (ESI) calcd for C$_{12}$H$_{14}$Br$_2$N$_5$O$_2$ (MH$^+$) 417.9509, found 417.9511.

General Procedure for the Synthesis of Tryptophan Based Region C Analogues: Tryptamine hydrochloride (0.150 g, 0.763 mmol), the desired appropriately substituted trichloroacetyl pyrrole (0.915 mmol), and anhydrous sodium carbonate (0.162 g, 1.53 mmol), were dissolved in anhydrous NNdimethylformamide (5 mL) The reaction was stirred at ambient temperature for 8 h upon which it was partitioned between ethyl acetate (75 mL) and water (35 mL). The organic layer was successively washed with water (3×20 mL), an aqueous solution of 1N HCl (2×35 mL), brine (20 mL), dried over anhydrous sodium sulfate, filtered, and concentrated under reduced pressure. Purification of the crude residue by column chromatography (Ethyl Acetate/Hexanes) yielded the final targets in the sub-library.

1H-pyrrole-2-carboxylic acid [2-(1H-indol-3-yl)-ethyl]-amide. white solid (80%): $^1$H NMR (300 MHz, DMSO-$d_6$) δ 11.41 (s, 1H), 10.80 (s, 1H), 8.11 (m, 1H), 7.58 (d, 1H, J=7.5 Hz), 7.33 (d, 1H, J=7.8 Hz), 7.16 (s, 1H), 7.08 (t, 1H, J=6.6 Hz), 6.97 (t, 1H, J=7.2 Hz), 6.83 (s, 1H), 6.74 (s, 1H), 6.06 (s, 1H) 3.47 (dt, 2H, J=7.2, 14.1 Hz), 2.90 (t, 2H, J=7.5 Hz); $^{13}$C NMR (100 MHz, DMSO-$d_6$) δ 160.69, 136.27, 127.31, 126.53, 122.58, 121.13, 120.95, 118.36, 118.25, 112.00, 111.40, 109.66, 108.52, 39.47, 25.59; HRMS (FAB) calcd for $C_{15}H_{16}N_3O$ (MH$^+$) 254.1293, found 254.1281.

4-bromo-1H-pyrrole-2-carboxylic acid [2-(1H-indol-3-yl)-ethyl]-amide. white solid (81%): $^1$H NMR (300 MHz, DMSO-$d_6$) δ 11.81 (s, 1H), 10.81 (s, 1H), 8.23 (t, 1H, J=6.0 Hz), 7.56 (d, 1H, J=7.8 Hz), 7.33 (d, 1H, J=8.1 Hz), 7.16 (s, 1H), 7.06 (t, 1H, J=6.6 Hz), 6.97 (m, 2H), 6.82 (s, 1H), 3.48 (dt, 2H, J=6.9, 13.5 Hz), 2.90 (t, 2H, J=7.8 Hz); $^{13}$C NMR (100 MHz, DMSO-$d_6$) δ 159.59, 136.25, 127.26, 127.14, 122.65, 121.06, 120.95, 118.31, 118.25, 111.84, 111.41, 111.26, 94.12, 25.39; HRMS (FAB) calcd for $C_{15}H_{15}BrN_3O$ (MH$^+$) 332.0398, found 332.0388.

4,5-dibromo-1H-pyrrole-2-carboxylic acid [2-(1H-indol-3-yl)-ethyl]amide. white solid (60%): $^1$H NMR (300 MHz, DMSO-$d_6$) δ 12.67 (s, 1H), 10.81 (s, 1H), 8.25 (t, 1H, J=5.1 Hz), 7.57 (d, 1H, J=8.1 Hz), 7.33 (d, 1H, J=8.4 Hz), 7.15 (s, 1H), 7.07 (t, 1H, J=6.9 Hz), 6.97 (t, 1H, J=7.2 Hz), 6.90 (d, 1H, J=2.7 Hz), 3.47 (dt, 2H, J=6.6, 13.2 Hz), 2.89 (t, 2H, J=7.2 Hz); $^{13}$C NMR (100 MHz, DMSO-$d_6$) δ 158.87, 136.25, 128.41, 127.25, 122.70, 120.96, 118.29, 118.27, 112.42, 111.76, 111.41, 104.39, 97.79, 39.57, 25.31; HRMS (ESI) calcd for $C_{15}H_{14}Br_2N_3O$ (MH$^+$) 409.9498, found 409.9501.

4,5-dichloro-1H-pyrrole-2-carboxylic acid [2-(1H-indol-3-yl)-ethyl]-amide. white solid (73%): $^1$H NMR (300 MHz, DMSO-$d_6$) δ 12.71 (s, 1H), 10.81 (s, 1H), 8.27 (m, 1H), 7.56 (d, 1H, J=7.8 Hz), 7.32 (d, 1H, J=8.1 Hz), 7.15 (s, 1H), 7.03 (t, 1H, J=6.9 Hz), 6.96 (t, 1H, J=6.9 Hz), 6.86 (s, 1H), 3.47 (dt, 2H, J=6.3, 13.2 Hz), 2.90 (t, 2H, J=7.5 Hz); $^{13}$C NMR (75 MHz, DMSO-$d_6$) δ 159.63, 136.91, 127.91, 125.80, 123.34, 121.61, 118.94, 118.91, 115.33, 112.41, 112.07, 110.09, 108.54, 25.98; HRMS (FAB) calcd for $C_{15}H_{13}Cl_2N_3O$ (M$^+$) 321.0436, found 321.0429.

1-methyl-pyrrole-2-carboxylic acid [2-(1H-indol-3-yl)-ethyl]-amide. white solid (63%): $^1$H NMR (300 MHz, DMSO-$d_6$) δ 10.81 (s, 1H), 8.10 (t, 1H, J=5.4 Hz), 7.57 (d, 1H, J=7.8 Hz), 7.33 (d, 1H, J=8.1 Hz), 7.16 (s, 1H), 7.06 (t, 1H, J=7.2 Hz), 7.00 (t, 1H, J=7.8 Hz) 6.87 (s, 1H), 6.73 (d, 1H, J=2.1 Hz), 6.00 (s, 1H), 3.84 (s, 3H), 3.45 (dt, 2H, J=6.9, 14.1 Hz), 2.89 (t, 2H, J=7.8 Hz); $^{13}$C NMR (75 MHz, DMSO-$d_6$) δ 161.31, 136.23, 127.46, 127.28, 125.78, 122.57, 120.91, 118.32, 118.21, 111.98, 111.94, 111.36, 106.51, 36.16, 25.49; HRMS (FAB) calcd for $C_{16}H_{18}N_3O$ (MH$^+$) 268.1450, found 268.1434.

4-bromo-1-methyl-pyrrole-2-carboxylic acid [2-(1H-indol-3-yl)-ethyl]amide. white solid (72%): $^1$H NMR (300 MHz, DMSO-$d_6$) δ 10.81 (s, 1H), 8.20 (t, 1H, J=5.4 Hz), 7.57 (d, 1H, J=7.8 Hz), 7.33 (d, 1H, J=8.1 Hz), 7.16 (d, 1H, J=1.8 Hz), 7.07 (m, 2H), 6.97 (t, 1H, J=6.9 Hz), 6.80 (d, 1H, J=1.8 Hz), 3.82 (s, 3H), 3.45 (dt, 2H, J=6.9, 14.1 Hz), 2.89 (t, 2H, J=7.8 Hz); $^{13}$C NMR (75 MHz, DMSO-$d_6$) δ 159.94, 136.04, 127.08, 126.63, 126.42, 122.48, 120.75, 118.12, 118.06, 113.24, 111.69, 111.23, 92.74, 36.31, 25.29; HRMS (FAB) calcd for $C_{16}H_{16}BrN_3O$ (M$^+$) 345.0477, found 345.0483.

4,5-dibromo-1-methyl-pyrrole-2-carboxylic acid [2-(1H-indol-3-yl)-ethyl]-amide. white solid (77%). $^1$H NMR (300 MHz, DMSO-$d_6$) δ 10.81 (s, 1H), 8.32 (t, 1H, J=5.7 Hz), 7.55 (d, 1H, J=7.5 Hz), 7.33 (d, 1H, J=8.1 Hz), 7.16 (s, 1H,) 7.06 (t, 1H, J=7.2 Hz), 7.00 (t, 1H, J=7.5 Hz), 6.95 (s, 1H), 3.88 (s, 3H), 3.45 (dt, 2H, J=6.3, 13.5 Hz), 2.89 (t, 2H, J=7.8 Hz); $^{13}$C NMR (100 MHz, DMSO-$d_6$) δ 159.66, 136.22, 128.15, 127.25, 122.67, 120.91, 118.24, 118.21, 113.78, 111.75, 111.37, 110.31, 96.81, 39.66, 35.32, 25.13; HRMS (ESI) calcd for $C_{16}H_{16}Br_2N_3O$ (MH$^+$) 423.9654, found 423.9655.

General Procedure for the Synthesis of Imidazole Based Region C Analogues (34-40): Histamine dihydrochloride 33 (0.100 g, 1.36 mmol), the desired appropriately substituted trichloroacetyl pyrrole (1.43 mmol), and anhydrous sodium carbonate (0.432 g, 4.08 mmol), were dissolved in anhydrous N,N-dimethylformamide (7 mL) The reaction was stirred at ambient temperature for 6 h upon which it was partitioned between ethyl acetate (75 mL) and water (35 mL). The organic layer was successively washed with water (3×20 mL), sat. NaHCO$_3$ (2×35 mL), brine (20 mL), dried over anhydrous sodium sulfate, filtered, and concentrated under reduced pressure. Purification of the crude residue by column chromatography (CH$_2$Cl$_2$/Methanol 85:15) delivered the desired targets in their free base form. Addition of concentrated HCl to a methanolic solution (8 mL) of the free base followed by rotary evaporation afforded the final analogues in this series as their corresponding hydrochloride salts.

1H-pyrrole-2-carboxylic acid [2-(1H-imidazol-4-yl)-ethyl]amide hydrochloride (34). white solid (54%): $^1$H NMR (400 MHz, DMSO-$d_6$) δ 11.46 (s, 1H), 9.01 (s, 1H), 8.23 (t, 1H, J=5.6 Hz), 7.46 (s, 1H), 6.82 (m, 1H), 6.73 (m, 1H), 6.05 (dd, 1H, J=2.8, 6.0 Hz), 3.50 (dt, 2H, J=6.8, 12.8 Hz), 2.87 (t, 1H, J=6.8 Hz); $^{13}$C NMR (100 MHz, DMSO-$d_6$) δ 161.40, 134.28, 131.82, 126.75, 122.01, 116.71, 110.80, 109.18, 37.98, 25.40; HRMS (FAB) calcd for $C_{10}H_{13}N_4O$ (MH$^+$) 205.1089, found 205.1083.

4-bromo-1H-pyrrole-2-carboxylic acid [2-(1H-imidazol-4-yl)-ethyl]-amide hydrochloride (35). white solid (40%): $^1$H NMR (300 MHz, DMSO-$d_6$) δ 11.80 (s, 1H), 8.18 (t, 1H, J=5.4 Hz), 7.53 (s, 1H), 6.96 (s, 1H), 6.80 (s, 2H), 3.41 (m, 2H), 2.70 (t, 2H, J=7.2 Hz); $^{13}$C NMR (100 MHz, DMSO-$d_6$) δ 159.55, 134.72, 127.06, 121.10, 116.67, 111.28, 94.92, 38.83, 27.18; HRMS (FAB) calcd for $C_{10}H_{12}BrN_4O$ (MH$^+$) 283.0194, found 283.0198.

4,5-dibromo-1H-pyrrole-2-carboxylic acid [2-(1H-imidazol-4-yl)-ethyl]-amide hydrochloride (36). white solid (35%): $^1$H NMR (300 MHz, DMSO-$d_6$) δ 12.64 (br s, 1H), 8.20 (t, 1H, J=5.7 Hz), 7.59 (s, 1H), 6.89 (s, 1H), 6.83 (s, 1H), 3.41 (dt, 2H, J=7.2, 13.2 Hz), 2.71 (t, 2H, J=7.2 Hz); $^{13}$C NMR (100 MHz, DMSO-$d_6$) δ 158.88, 133.83, 131.81, 128.10, 116.27, 112.97, 104.45, 97.84, 37.82, 25.10; HRMS (FAB) calcd for $C_{10}H_{11}Br_2N_4O$ (MH$^+$) 360.9300, found 360.9295.

4,5-dichloro-1H-pyrrole-2-carboxylic acid [2-(1H-imidazol-4-yl)-ethyl]-amide hydrochloride (37). white solid (62%): $^1$H NMR (400 MHz, DMSO-$d_6$) δ 12.82 (s, 1H), 9.02 (s, 1H), 8.56 (t, 1H, J=5.6 Hz), 7.46 (s, 1H), 6.94 (d, 1H, J=2.8 Hz), 3.50 (dt, 2H, J=6.8, 12.8 Hz), 2.89 (t, 2H, J=6.4 Hz); $^{13}$C NMR (100 MHz, DMSO-$d_6$) δ 159.04, 133.53, 130.96, 124.76, 116.10, 114.73, 110.16, 107.95, 37.49, 24.43; HRMS (ESI) calcd for $C_{10}H_{11}Cl_2N_4O$ (MH$^+$) 273.0304, found 273.0309.

1-methyl-pyrrole-2-carboxylic acid [2-(1H-imidazol-4-yl)-ethyl]-amide hydrochloride (38). white solid (55%): $^1$H NMR (300 MHz, DMSO-d$_6$) δ 14.60 (bs, 1H), 14.32 (bs, 1H), 9.03 (s, 1H), 8.17 (s, 1H), 7.50 (s, 1H), 6.87 (s, 1H), 6.74 (s, 1H), 5.98 (d, 1H, J=2.7 Hz), 3.80 (s, 3H), 3.48 (m, 2H), 2.88 (m, 2H); $^{13}$C NMR (100 MHz, DMSO-d$_6$) δ 161.32, 134.68, 127.51, 125.75, 116.69, 111.98, 106.57, 38.77, 36.14, 27.17; HRMS (ESI) calcd for C$_{11}$H$_{15}$N$_4$O (MH$^+$) 219.1240, found 219.1245.

4-bromo-1-methyl-pyrrole-2-carboxylic acid [2-(1H-imidazol-4-yl)-ethyl]-amide hydrochloride (39). white solid (54%): $^1$H NMR (300 MHz, DMSO-d$_6$) δ 11.86 (br s, 1H), 8.15 (m, 1H), 7.53 (s, 1H), 7.06 (d, 1H, J=1.5 Hz), 6.79 (m, 2H), 3.81 (s, 3H), 3.38 (m, 2H), 2.69 (t, 1H, J=7.8 Hz); $^{13}$C NMR (75 MHz, DMSO-d$_6$) δ 160.12, 134.66, 126.83, 126.52, 113.36, 92.85, 38.80, 36.29, 27.00; HRMS (ESI) calcd for C$_{11}$H$_{14}$BrN$_4$O (MH$^+$) 297.0345. found 297.0348.

4,5-dibromo-1-methyl-pyrrole-2-carboxylic acid [2-(1H-imidazol-4-yl)-ethyl]-amide hydrochloride (40). white solid (60%): $^1$H NMR (300 MHz, DMSO-d$_6$) δ 11.85 (br s, 1H), 8.26 (t, 1H, J=5.4 Hz), 7.54 (s, 1H), 6.95 (s, 1H), 6.80 (s, 1H), 3.87 (s, 3H), 3.39 (dt, 2H, J=6.9, 13.8 Hz), 2.70 (t, 2H, J=7.2 Hz); $^{13}$C NMR (100 MHz, DMSO-d$_6$) δ 159.72, 133.67, 131.48, 127.78, 116.20, 114.14, 110.62, 96.88, 37.75, 35.33, 24.71; HRMS (FAB) calcd for C$_{11}$H$_{13}$Br$_2$N$_4$O$_2$ (MH$^+$) 374.9456, found 374.9458.

4-(3-amino-propyl)-1,3-dihydro-imidazole-2-thione hydrochloride (42). To an Erlenmeyer flask was prepared a solution of L-ornithine methyl ester hydrochloride (10.50 g, 47.9 mmol) in water (125 mL) The solution was cooled to 5° C. and pH adjusted to a value of 1.5 with concentrated HCl. While being careful to maintain the above stated temperature and pH, 5% Na(Hg) (250 g) was added slowly to the solution over a time period of 35 min After the addition was complete and bubbling had calmed the Hg was decanted from the solution. The remaining aqueous portion was drained into a separate flask where potassium thiocyanate (14.0 g, 144 mmol) and water (75 mL) was added. The pH of solution was adjusted to a value of 4.30 and the flask was then heated at 95° C. while open to the atmosphere for 1.5 h. After cooling to room temperature, ethanol (75 mL) was added and the reaction was evaporated to dryness. The residue was taken up in methanol and filtered to remove NaCl. After all of the NaCl had been removed the crude residue was purified by column chromatography (CH$_2$Cl$_2$/MeOH sat. with NH$_3$ 80:20) to afford the desired compound in its free base form. Addition of concentrated hydrochloric acid to a methanol solution (50 mL) of the free base followed by evaporation to dryness gave 4.51 g (48%) of the title compound 42 as a tan solid: $^1$H NMR (300 MHz, DMSO-d$_6$) δ 11.92 (s, 1H), 11.69 (s, 1H), 7.77 (s, 2H), 6.58 (s, 1H), 2.73 (m, 2H), 2.42 (t, 2H, J=6.6 Hz), 1.76 (tt, 2H, J=7.5, 13.8 Hz); $^{13}$C NMR (100 MHz, DMSO-d$_6$) δ 160.23, 128.03, 111.69, 38.08, 25.75, 21.27; HRMS (FAB) calcd for C$_6$H$_{12}$N$_3$S (MH$^+$) 158.0752, found 158.0743.

General Procedure for the synthesis of 2-thioimadazolone region C analogues (43-49): 4-(3-amino-propyl)-1,3-dihydro-imidazole-2-thione hydrochloride 42 (0.150 g, 0.774 mmol), the desired appropriately substituted trichloroacetyl pyrrole (0.852 mmol), and anhydrous sodium carbonate (0.246 g, 2.32 mmol), were dissolved in anhydrous N,N-dimethylformamide (5 mL). The reaction was stirred at ambient temperature for 12 h upon which it was partitioned between ethyl acetate (75 mL) and water (35 mL). The organic layer was successively washed with water (3×20 mL), a 1N aqueous solution of HCl (2×35 mL), brine (20 mL), dried over anhydrous sodium sulfate, filtered, and concentrated under reduced pressure. Purification of the crude residue by column chromatography (CH$_2$Cl$_2$/Methanol) afforded the final analogues in this series.

1H-pyrrole-2-carboxylic acid [3-(2-thioxo-2,3-dihydro-1H-imidazol-4-yl)-propyl]-amide (43). pale yellow solid (53%): $^1$H NMR (300 MHz, DMSO-d$_6$) δ 11.40 (s, 1H), 8.20 (t, 1H, J=5.7 Hz), 6.97 (s, 1H), 6.82 (m, 1H), 6.75 (m, 1H), 6.06 (dd, 1H, J=2.1, 5.4 Hz), 3.23 (dt, 2H, J=6.6, 12.9 Hz), 2.52 (m, 2H), 1.75 (tt, 2H, J=7.2, 14.7 Hz); $^{13}$C NMR (75 MHz, DMSO-d$_6$) δ 160.80, 160.71, 130.67, 126.31, 121.14, 113.24, 109.77, 108.47, 37.67, 28.32, 22.01; HRMS (FAB) calcd for C$_{11}$H$_{15}$N$_4$OS (MH$^+$) 251.0967, found 251.0961.

4-bromo-1H-pyrrole-2-carboxylic acid [3-(2-thioxo-2,3-dihydro-1H-imidazol-4-yl)-propyl]-amide (44). pale yellow solid (52%): $^1$H NMR (300 MHz, DMSO-d$_6$) δ 11.87 (s, 1H), 11.81 (s, 1H), 11.65 (s, 1H), 8.10 (t, 1H, J=5.1 Hz), 6.96 (s, 1H), 6.83 (s, 1H), 6.57 (s, 1H), 3.18 (dt, 2H, J=6.3, 12.3 Hz), 2.37 (t, 2H, J=7.5 Hz), 1.71 (tt, 2H, J=6.9, 13.8 Hz); $^{13}$C NMR (100 MHz, DMSO-d$_6$) δ 160.35, 160.30, 130.05, 127.63, 121.74, 112.76, 112.04, 95.56, 38.43, 28.77, 22.52; HRMS (ESI) calcd for C$_{11}$H$_{14}$BrN$_4$OS (MH$^+$) 329.0066, found 329.0062.

4,5-dibromo-1H-pyrrole-2-carboxylic acid [3-(2-thioxo-2,3-dihydro-1H-imidazol-4-yl)-propyl]-amide (45). white solid (41%): $^1$H NMR (300 MHz, DMSO-d$_6$) δ 12.68 (s, 1H), 11.86 (s, 1H), 11.65 (s, 1H), 8.13 (t, 1H, J=5.1 Hz), 6.91 (d, 1H, J=2.7 Hz), 6.57 (s, 1H), 3.17 (m, 2H), 2.36 (t, 2H, J=6.9 Hz), 1.70 (tt, 2H, J=6.9, 13.8 Hz); $^{13}$C NMR (75 MHz, DMSO-d$_6$) δ 160.04, 158.91, 128.85, 128.02, 112.45, 111.30, 104.43, 97.76, 37.78, 27.95, 21.72; HRMS (ESI) calcd for C$_{11}$H$_{13}$Br$_2$N$_4$OS (MH$^+$) 406.9171, found 406.9174.

4,5-dichloro-1H-pyrrole-2-carboxylic acid [3-(2-thioxo-2,3-dihydro-1H-imidazol-4-yl)-propyl]-amide (46). yellow solid (65%): $^1$H NMR (300 MHz, DMSO-d$_6$) δ 12.71 (s, 1H), 11.86 (s, 1H), 11.65 (s, 1H), 8.15 (m, 1H), 6.86 (s, 1H), 6.56 (s, 1H), 3.17 (m, 2H), 2.36 (t, 2H, J=7.5 Hz), 1.71 (m, 2H); $^{13}$C NMR (100 MHz, DMSO-d$_6$) δ 160.73, 159.70, 129.53, 125.60, 115.40, 111.97, 110.16, 108.55, 38.47, 28.62, 22.40; HRMS (FAB) calcd for C$_{11}$H$_{12}$Cl$_2$N$_4$OS (M$^+$) 318.0109, found 318.0099.

1-methyl-pyrrole-2-carboxylic acid [3-(2-thioxo-2,3-dihydro-1H-imidazol-4-yl)-propyl]-amide (47). pale yellow solid (57%): $^1$H NMR (300 MHz, DMSO-d$_6$) δ 7.99 (m, 1H), 6.99 (s, 1H), 6.86 (s, 1H), 6.74 (m, 1H), 5.98 (m, 1H), 3.20 (dt, 2H, J=6.0, 12.3 Hz), 2.54 (t, 2H, J=7.2 Hz), 1.77 (tt, 2H, J=6.9, 14.1 Hz); $^{13}$C NMR (75 MHz, DMSO-d$_6$) 161.38, 160.95, 127.51, 125.64, 115.10, 112.09, 106.50, 97.60, 37.71, 36.11, 28.32, 22.15; HRMS (ESI) calcd for C$_{12}$H$_{17}$N$_4$OS (MH$^+$) 265.1118, found 265.1120.

4-bromo-1-methyl-pyrrole-2-carboxylic acid [3-(2-thioxo-2,3-dihydro-1H-imidazol-4-yl)-propyl]-amide (48). yellow solid (54%): $^1$H NMR (300 MHz, DMSO-d$_6$) 11.86 (s, 1H), 11.64 (s, 1H), 8.07 (m, 1H), 7.07 (s, 1H), 6.81 (s, 1H), 6.56 (s, 1H), 3.80 (s, 3H), 3.13 (dt, 2H, J=6.3, 12.9 Hz), 2.36 (t, 2H, J=7.8 Hz), 1.69 (m, 2H); $^{13}$C NMR (75 MHz, DMSO-d$_6$) δ 160.25, 160.00, 128.95, 126.85, 126.45, 113.45, 111.34, 92.87, 37.70, 36.30, 27.96, 21.78; HRMS (ESI) calcd for C$_{12}$H$_{16}$BrN$_4$OS (MH$^+$) 343.0222, found 343.0223.

4,5-dibromo-1-methyl-pyrrole-2-carboxylic acid [3-(2-thioxo-2,3-dihydro-1H-imidazol-4-yl)-propyl]-amide (49). white solid (71%): $^1$H NMR (400 MHz, DMSO-d$_6$) 11.85 (s, 1H), 11.64 (s, 1H), 8.19 (t, 1H, J=5.2 Hz), 6.97 (s, 1H), 6.55 (s, 1H), 3.86 (s, 3H), 3.15 (dt, 2H, J=6.4, 12.4 Hz), 2.36 (t, 2H, J=7.2 Hz), 1.70 (tt, 2H, J=7.2, 14.0 Hz); $^{13}$C NMR (75 MHz, DMSO-d$_6$) δ 160.00, 159.76, 128.89, 128.10, 113.84, 111.33, 110.42, 96.84, 37.86, 35.35, 27.85, 21.77; HRMS (ESI) calcd for C$_{12}$H$_{15}$Br$_2$N$_4$OS (MH$^+$) 420.9328, found 420.9327.

1-bromo-5-phthalimido-2-pentanone. 4-phthalimidobutanoic acid 50 (4.64 g, 19.9 mmol) was dissolved in $CH_2Cl_2$ (100 mL) at 0° C. and a catalytic amount of DMF was added. To this solution was added oxalyl chloride (5.2 mL, 59.6 mmol) drop-wise and the solution was then warmed to room temperature. After 1 h, the solvent and excess oxalyl chloride were removed under reduced pressure. The resulting solid was dissolved into $CH_2Cl_2$ (10 mL) and added slowly to a 0° C. solution of $CH_2N_2$ (~60 mmol generated from Diazald® diazomethane precursor/KOH) in $Et_2O$ (170 mL). This solution was stirred at 0° C. for 1.5 h at which time the reaction was quenched with the drop-wise addition of 48% HBr (7.0 mL). The reaction mixture was diluted with $CH_2Cl_2$ (50 mL) and immediately washed with sat. $NaHCO_3$, brine, dried ($MgSO_4$), filtered and concentrated. The resulting white solid was filtered and washed with $Et_2O$ (100 mL) to obtain the title compound (4.77 g, 84%) as a fine white powder: $^1H$ NMR (300 MHz, DMSO-$d_6$) δ 7.85 (m, 4H), 4.32 (s, 2H), 3.57 (t, 2H, J=6.9 Hz), 2.65 (t, 2H, J=6.9 Hz), 1.82 (quint., 2H, J=6.9 Hz); $^{13}C$ NMR (75 MHz, DMSO-$d_6$) δ 200.94, 168.05, 134.34, 131.68, 123.01, 36.94, 36.64, 36.37, 22.30; HRMS (ESI) calcd for $C_{13}H_{13}BrNO_3$ (MH$^+$) 310.0073, found 310.0072.

2-amino-4-(3-phthalimidopropyl)thiazole (51). 1-bromo-5-phthalimido-2-pentanone (0.500 g, 1.61 mmol) was dissolved in DMF (3.5 mL) at 0° C. and thiourea (0.135 g, 1.77 mmol) was added drop-wise as a solution in DMF (0.50 mL). The solution was allowed to warm to room temperature and stirring was continued for 2 h at which time the DMF was removed under reduced pressure and the resulting slurry was made alkaline with 10% $K_2CO_3$ (100 mL). The aqueous solution was then extracted with EtOAc (3×40 mL) and the organic layer was washed with brine (50 mL), dried ($Na_2SO_4$), filtered and concentrated to obtain 51 (448 mg, 97%) as a fine white powder in its freebase form: $^1H$ NMR (300 MHz, DMSO-$d_6$) δ 7.85 (m, 4H), 6.78 (s, 2H), 6.13 (s, 1H), 3.56 (t, 2H, J=6.9 Hz), 2.42 (t, 2H, J=7.5 Hz), 1.88 (quint., 2H, J=7.5 Hz); $^{13}C$ NMR (75 MHz, DMSO-$d_6$) δ 168.01, 167.87, 151.20, 134.25, 131.61, 122.89, 100.17, 37.27, 28.70, 27.09; HRMS (ESI) calcd for $C_{14}H_{14}N_3O_2S$ (MH$^+$) 288.0801, found 288.0799.

2-amino-4-(3-aminopropyl)thiazole dihydrochloride. 2-amino-4-(3-phthalimidopropyl)thiazole (51) (0.300 g, 1.04 mmol) was dissolved in MeOH (4.5 mL) and $N_2H_4$ (0.10 mL, 3.20 mmol) was added drop-wise to the stirring solution. The solution was stirred at room temperature for 1 h, warmed to 55° C. for 0.5 h and then cooled to room temperature. The slurry was filtered and the filtrate concentrated under reduced pressure. The resulting residue was purified by flash column chromatography (50-100% MeOH/$CH_2Cl_2$; followed by 5-7% TEA/MeOH) to obtain the corresponding freebase (0.148 g, 90%) as a fine white powder. Addition of concentrated HCl to a cold methanolic solution (8 mL) of the freebase followed by evaporation under reduced pressure delivered the title compound as its dihydrochloride salt. $^1H$ NMR (300 MHz, DMSO-$d_6$) δ 9.07 (bs, 2H), 8.06 (bs, 3H), 6.57 (s, 1H), 2.78 (m, 2H), 2.62 (t, 2H, J=7.2 Hz), 1.87 (quint., 2H, J=7.2 Hz); $^{13}C$ NMR (75 MHz, DMSO-$d_6$) δ 169.90, 139.21, 102.13, 37.68, 25.10, 24.47; HRMS (ESI) calcd for $C_6H_{12}N_3S$ (MH$^+$) 158.0746, found 158.0745.

General Procedure for the synthesis of 2-AT region C analogues: 2-amino-4-(3-aminopropyl)thiazole (0.200 mmol), the appropriately substituted trichloroacetyl pyrrole (0.210 mmol) and anhydrous potassium carbonate (0.300 mmol) were dissolved in anhydrous N,N-dimethylformamide (1.5 mL) and allowed to stir for 16 h at room temperature. The mixture was then concentrated under reduced pressure and the resulting residue was dissolved in EtOAc (40 mL) and washed with $H_2O$ (3×20 mL) and brine (20 mL), dried ($Na_2SO_4$), filtered and concentrated. The crude residue was purified by flash column chromatography (30-100% EtOAc/Hexanes; followed by 5-10% MeOH/EtOAc) to obtain pure product. Addition of concentrated HCl to a methanolic solution (5 mL) of the freebase followed by concentration under reduced pressure afforded the requisite analogues for this series as their hydrochloride salts.

1H-pyrrole-2-carboxylic acid [3-(2-amino-thiazol-4-yl)-propyl]-amide Hydrochloride. tan solid (64%): $^1H$ NMR (300 MHz, DMSO-$d_6$) 11.51 (s, 1H), 9.26 (s, 2H), 8.21 (s, 1H), 6.84 (s, 1H), 6.79 (s, 1H), 6.59 (s, 1H), 6.07 (d, 1H, J=2.7 Hz), 3.24 (q, 2H, J=5.7 Hz), 2.57 (t, 2H, J=7.2 Hz), 1.79 (quint., 2H, J=7.2 Hz); $^{13}C$ NMR (75 MHz, DMSO-$d_6$) δ 169.90, 160.68, 139.79, 126.28, 121.02, 110.02, 108.34, 101.61, 37.49, 27.59, 24.93; HRMS (ESI) calcd for $C_{11}H_{15}N_4OS$ (MH$^+$) 251.0961, found 251.0960.

4,5-dibromo-1H-pyrrole-2-carboxylic acid [3-(2-amino-thiazol-4-yl)-propyl]-amide hydrochloride. tan solid (56%): $^1H$ NMR (400 MHz, DMSO-$d_6$) 12.76 (s, 1H), 9.19 (s, 2H), 8.36 (t, 1H, J=5.6 Hz), 6.96 (d, 1H, J=2.0 Hz), 6.58 (s, 1H), 3.23 (q, 2H, J=7.2 Hz), 2.56 (t, 2H, J=7.2 Hz), 1.78 (quint., 2H, J=7.2 Hz); $^{13}C$ NMR (75 MHz, DMSO-$d_6$) δ 169.91, 158.87, 139.93, 128.23, 112.81, 104.20, 101.70, 97.76, 37.67, 27.35, 25.00; HRMS (ESI) calcd for $C_{11}H_{13}Br_2N_4OS$ (MH$^+$) 406.9171, found 406.9165.

1-methyl-pyrrole-2-carboxylic acid [3-(2-amino-thiazol-4-yl)-propyl]-amide Hydrochloride. tan solid (56%): $^1H$ NMR (300 MHz, DMSO-$d_6$) 9.19 (br s, 2H), 8.08 (m, 2H), 6.88 (t, 1H, J=2.1 Hz), 6.78 (dd, 1H, J=3.9 & 2.1 Hz), 6.57 (s, 1H), 5.99 (dd, 1H, J=3.9 & 2.7 Hz), 3.82 (s, 3H), 3.20 (q, 2H, J=7.2 Hz), 2.55 (t, 2H, J=7.2 Hz), 1.78 (quint., 2H, J=7.2 Hz); $^{13}C$ NMR (75 MHz, DMSO-$d_6$) δ 169.83, 161.37, 139.93, 127.40, 125.54, 112.04, 106.40, 101.54, 37.44, 35.94, 27.52, 24.98; HRMS (ESI) calcd for $C_{12}H_{17}N_4OS$ (MH$^+$) 265.1118, found 265.1117.

4,5-dibromo-1-methyl-pyrrole-2-carboxylic acid [3-(2-amino-thiazol-4-yl)-propyl]-amide hydrochloride. tan solid (62%): $^1H$ NMR (400 MHz, DMSO-$d_6$) 9.02 (br s, 2H), 8.29 (m, 1H), 7.02 (s, 1H), 6.55 (s, 1H), 3.87 (s, 3H), 3.19 (q, 2H, J=6.8 Hz), 2.53 (m, 2H), 1.77 (t, 2H, J=6.8 Hz); $^{13}C$ NMR (75 MHz, DMSO-$d_6$) δ 169.92, 159.83, 140.23, 128.03, 114.03, 110.40, 101.71, 96.86, 37.78, 35.34, 27.31, 25.14; HRMS (ESI) calcd for $C_{12}H_{15}Br_2N_4OS$ (MH$^+$) 420.9328, found 420.9321.

Example 5

Activity Testing. A standard crystal violet reporter assay is employed to assess the effect of compounds on the formation of biofilms Among others, the following strains are tested:
Xanthomonas Xccl
Xanthomonas Xcv.135
Xanthomonas XcvS
Xanthomonas Xccp
Xanthomonas Xcp60
Xanthomonas Xcp25
Ralstonia solanacearum K66
Xanthomonas* is a Gram-negative rod-shaped bacterium that is a common plant pathogen. *Xanthomonas* bacteria grow almost exclusively in plants. *Xanthomonas* species testing includes *X. vesicatoria* (crop=tomato), *X. euvesicatoria* (crop=pepper), *X. campestris* (crop=crucifers, particularly cabbage), *X. zinniae* (crop=zinnia), and *X. fragariae* (crop=strawberry). *Ralstonia solanacearum* is a Gram-negative bacterium that is found in soil.

Bacteria are allowed to form biofilms in a multi-well plate in the absence or presence of one or more compounds. Planktonic (or free growing) bacteria are then removed, wells washed vigorously, and crystal violet added. Crystal violet stains the remaining bacteria which, following ethanol solubilization, is quantitated by spectrophotometry ($A_{540}$). Time-dependent and concentration-dependent analysis of each compound are performed.

Example 6

Activity testing of imidazole library embers on *Xanthomonas*. Biofilm formation on PVC microtiter wells was accomplished using *Xanthomonas* strains Xcv 135 (known to infect peppers and tomatoes) and Xcv 5 (known to infect tomatoes but not peppers) as models. The Starting Optical Density (OD at 600 nm) for biofilm attachment assay was 0.55, the temperature for this assay was 28° C., the duration of incubation was 6 hours under, and the assay was, static.

Biofilm inhibition results are as follows for screens with Xcv 135. The Xcv 5 strain is tested in the same manner.

| Compound Screened | % Inhibition at 20 μM (vs. Xcv 135) |
|---|---|
| Formula (II)(b)(vi)(trans)(±) | 71% |
| Formula (II)(b)(v)(trans)(±) | 0% |
| Formula (II)(a)(±) | 0% |

Formula (II)(b)(vi)(trans)(±):

(II)(b)(vi)(trans)(±)

Formula (II)(b)(v)(trans)(±):

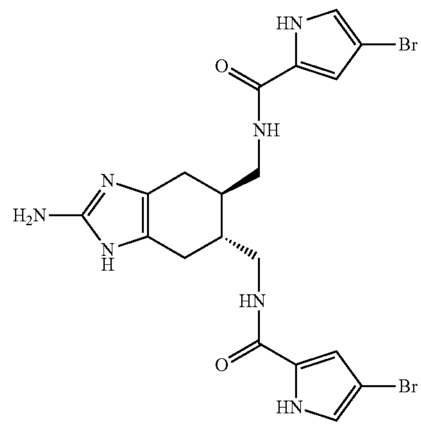

(II)(b)(v)(trans)(±)

Formula (II)(a)(±):

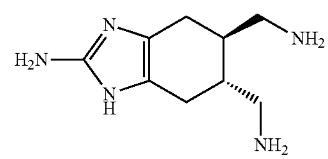

(II)(a)(±)

Example 7

Field testing of active compounds with pepper plants. Each active compound is evaluated under field conditions to determine whether it controls or enhances control of bacterial spot (caused by the bacterium *Xanthomonas euvesicatoria*) of pepper when applied alone or in tank-mixtures with a copper (Kocide 3000), an antibiotic (GWN-9350, gentamicin), or a putative plant defense activator (Prophyt). Foliar disease is rated with a 0-9 rating scale with 0=no disease, 1=at least 1 diseased leaf, 2=1-5% foliage diseased or defoliated, 3=6-10%, 4=11-15%, 5=16-25%, 6=26-50%, 7=51-75%, 8=76-99%, and 9=100% leaves diseased or plant completely defoliated, and expressed as disease progress over time using the calculated Area Under the Disease Progress Curve (AUDPC). Mean fruit per plant and mean weight of fruit per plant are also calculated. Plants treated with an active compound alone or in combination with the copper, antibiotic or putative plant defense activator is compared to untreated plants or plants treated without addition of an active compound.

The foregoing is illustrative of the present invention, and is not to be construed as limiting thereof. The invention is defined by the following claims, with equivalents thereof to be included therein.

That which is claimed is:

1. A method of removing or controlling microbial biofilm formation or microbial infection in a plant or plant part thereof, comprising applying to said plant or plant part a treatment effective amount of:
a compound of Formula (X)(I)(a):

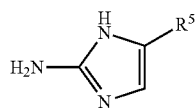

(X)(I)(a)

wherein:
R⁵ is an alkyl, alkenyl or alkynyl having an amide group substituted thereon, or an agriculturally acceptable salt thereof.

2. The method of claim 1, wherein said plant is a fruit crop plant or a vegetable crop plant.

3. The method of claim 1, wherein said compound is applied in an amount effective to treat or control a bacterial disease caused by a species selected from the group consisting of: *Xanthomonas* sp., *Pseudomonas* sp., *Agrobacterium* sp., *Xylella* sp., *Erwinia* sp., *Pectobacterium* sp., *Bacillus* sp, and *Ralstonia* sp.

4. The method of claim 1, wherein said plant is selected from the group consisting of: soybean, corn, cotton, wheat, and rice.

5. The method of claim 1, wherein said microbial biofilm formation or microbial infection is caused by a fungi.

6. The method of claim 1, wherein said compound is applied to said plant in an amount effective to treat or control a fungal disease selected from the group consisting of rots, leaf molds, blights, wilts, damping-off, spot, root rot, stem rot, mildew, brown spot, gummosis, melanose, post-bloom fruit drop, scab, alternaria, canker, flyspeck, fruit blotch, dieback, downy mildews, ear rots, anthracnose bunts, smut, rust, eyespot and pecky rice.

7. The method of claim 5, wherein said plant is selected from the group consisting of: citrus, pome fruit, tomato, soybean, grape, potato, cotton, corn, rice, and wheat.

8. A method of enhancing the effects of a microbicide comprising applying in combination with said microbicide:
a compound of Formula (X)(I)(a):

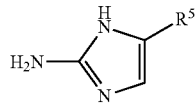

(X)(I)(a)

wherein:
R⁵ is an alkyl, alkenyl or alkynyl having an amide group substituted thereon, or an agriculturally acceptable salt thereof,
wherein said microbicide comprises copper.

9. The method of claim 8, wherein said applying step is carried out by applying said active compound and said microbicide simultaneously.

10. The method of claim 8, wherein said applying step is carried out by applying said active compound and said microbicide sequentially.

11. The method of claim 1, wherein said compound is a compound of Formula (X)(I)(a)(2):

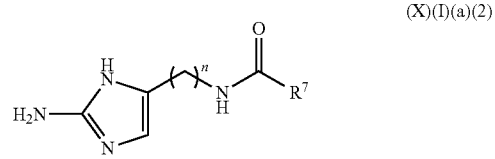

(X)(I)(a)(2)

wherein:
n is 2, 3 or 4, saturated or unsaturated; and
R⁷ is selected from the group consisting of: H, alkyl, alkenyl and alkynyl;
or an agriculturally acceptable salt thereof.

12. The method of claim 11, wherein R⁷ is an alkyl having from 5 to 20 carbon atoms.

13. The method of claim 12, wherein n is 3.

14. The method of claim 1, wherein said compound is a compound of Formula (X)(I)(a)(2)(A):

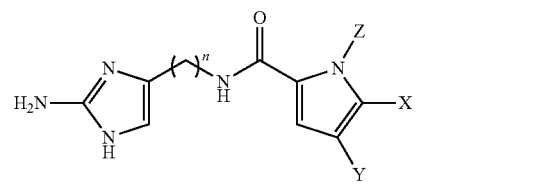

(X)(I)(a)(2)(A)

wherein:
n is 2, 3 or 4, saturated; and
X, Y and Z are each independently selected from the group consisting of: H, methyl, Br and Cl;
or an agriculturally acceptable salt thereof.

15. The method of claim 14, wherein said compound represented by Formula (X)(I)(a)(2)(A) is a compound of Formula (X)(I)(a)(2)(A)(i):

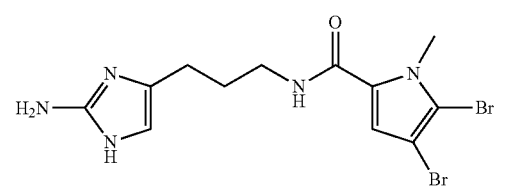

(X)(I)(a)(2)(A)(i)

or an agriculturally acceptable salt thereof.

16. The method of claim 8, wherein said compound is a compound of Formula (X)(I)(a)(2):

(X)(I)(a)(2)

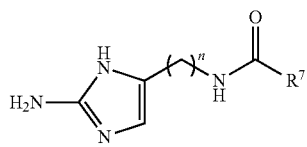

wherein:
n is 2, 3 or 4, saturated or unsaturated; and
R[7] is selected from the group consisting of: H, alkyl, alkenyl and alkynyl;
or an agriculturally acceptable salt thereof.

17. The method of claim 16, wherein R[7] is an alkyl having from 5 to 20 carbon atoms.

18. The method of claim 17, wherein n is 3.

19. The method of claim 8, wherein said compound is a compound of Formula (X)(I)(a)(2)(A):

(X)(I)(a)(2)(A)

wherein:
n is 2, 3 or 4, saturated; and
X, Y and Z are each independently selected from the group consisting of: H, methyl, Br and Cl;
or an agriculturally acceptable salt thereof.

20. The method of claim 19, wherein said compound represented by Formula (X)(I)(a)(2)(A) is a compound of Formula (X)(I)(a)(2)(A)(i):

(X)(I)(a)(2)(A)(i)

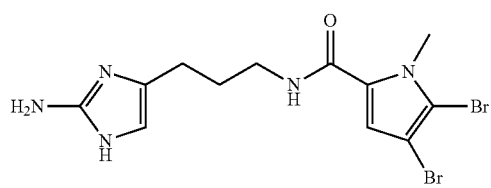

or an agriculturally acceptable salt thereof.

* * * * *

UNITED STATES PATENT AND TRADEMARK OFFICE
CERTIFICATE OF CORRECTION

PATENT NO. : 8,927,029 B2
APPLICATION NO. : 14/088926
DATED : January 6, 2015
INVENTOR(S) : Melander et al.

It is certified that error appears in the above-identified patent and that said Letters Patent is hereby corrected as shown below:

In the specification

Column 18, Line 5: Please correct the compound below:

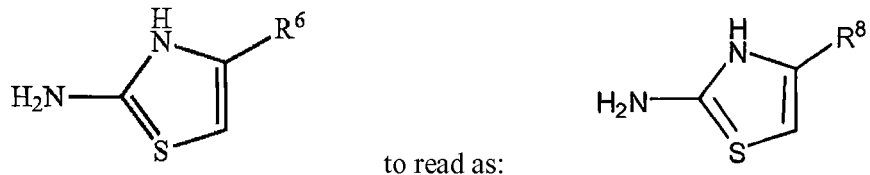

to read as:

Column 19, Line 36: Please correct "wherein $R^H$ is" to read -- wherein $R^{11}$ is --

Column 26, Line 59: Please correct the compound below:

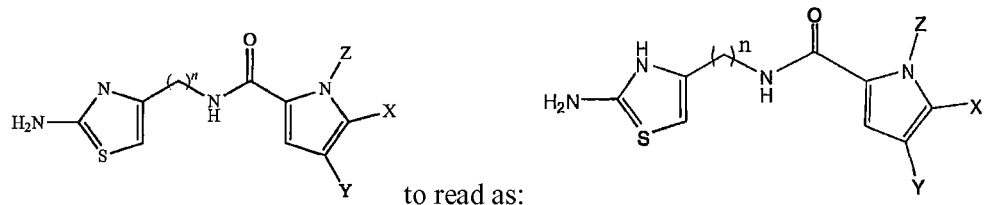

to read as:

Column 28, Line 50: Please correct "(II)(b)(vi)(trans)(+)"
to read -- (II)(b)(vi)(trans)(±) --

Column 35, Line 29: Please correct "(X)(I)(a)(2):"
to read -- (X)(I)(c)(2): --

Column 43, Line 34: Please correct "depicted as Formula"
to read -- depicted as Formula (I)(a): --

Signed and Sealed this
Seventeenth Day of May, 2016

Michelle K. Lee
*Director of the United States Patent and Trademark Office*

CERTIFICATE OF CORRECTION (continued)
U.S. Pat. No. 8,927,029 B2

In the specification

Column 46, Line 7: Please correct Formula (II) below:

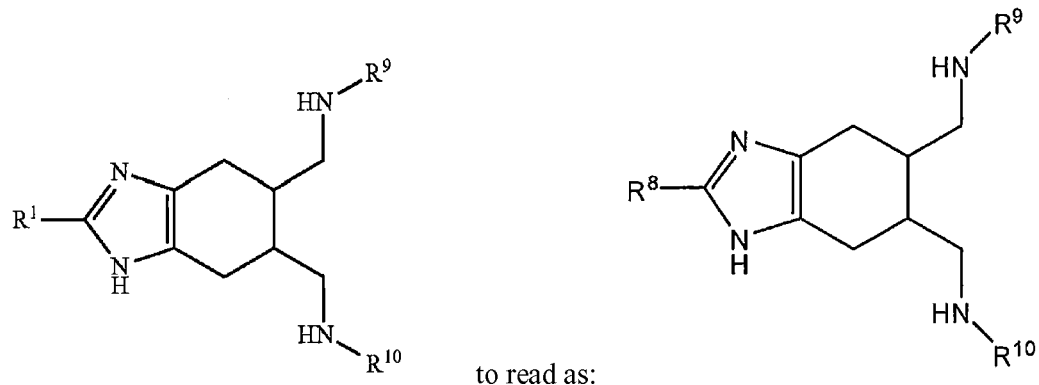

to read as:

Column 59, Line 42: Please correct "(X)(I)(a)(2):"
        to read -- (X)(I)(c)(2): --

Column 81, Line 42: Please correct "$C_{11}H_{15}N_{60}$ (MH)+"
        to read -- $C_{11}H_{15}N_6O$ $(MH)^+$ --

Column 86, Scheme 10, Lines 31-35: Please correct:

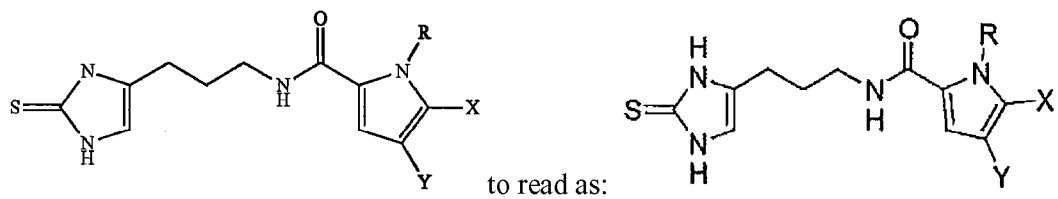

to read as:

Column 88, Line 65: Please correct "target compound II"
        to read -- target compound 11 --

Column 98, Line 55: Please correct "*Xanthomonas* XcvS"
        to read -- *Xanthomonas* Xcv5 --